United States Patent [19]

Blau et al.

[11] Patent Number: 5,008,081
[45] Date of Patent: Apr. 16, 1991

[54] METHOD AND APPARATUS FOR AUTOMATIC MELT INDEXING

[75] Inventors: David A. Blau, Cupertino; John Meadows; Thomas M. Sherlock, both of Los Altos Hills; Fred Stengel, Redwood City; Robert M. Studholme, Saratoga; Kenneth R. Wada; Christopher J. Kepner, both of San Jose, all of Calif.

[73] Assignee: KD Group, Mountain View, Calif.

[21] Appl. No.: 256,022

[22] Filed: Oct. 11, 1988

[51] Int. Cl.⁵ .............................................. G01N 35/00
[52] U.S. Cl. ....................................... 422/64; 422/63; 422/67; 436/43; 73/56
[58] Field of Search ............................ 422/63–67; 73/54, 56; 374/102, 160; 436/43

[56] References Cited

U.S. PATENT DOCUMENTS 3,758,776  9/1973  Frohne et al. ......................... 73/56
4,096,739  6/1978  Barker et al. ......................... 73/56

OTHER PUBLICATIONS

"Zymate Laboratory Automation System", brochure of the Zymark Corporation, Hopkinton, Mass.; 11/04/1986.

Primary Examiner—Robert J. Warden
Assistant Examiner—D. John Griffith, Jr.
Attorney, Agent, or Firm—Irell & Manella

[57] ABSTRACT

Computer-controlled method and apparatus for automatic melt index testing, including a housing with a base carrying a heater block having a bore therein for receiving a metal cartridge. A cartridge carousel is rotatably carried on the base, and carries a plurality of such cartridges, each cartridge having a plug at the bottom end thereof with a orifice through the plug, and each cartridge having a bore therein for receiving a sample of a test substance and for receiving a piston on top of the pellets. A lift arm grasps the cartridges, one at a time, and places each cartridge into the heater block, under the control of a microcomputer, by both lifting and rotating the transfer arm. The transfer arm includes a solenoid-operated grip for grasping the cartridges.

The test unit carries a lift mechanism with a weight mounted atop a tamping rod, and an optical sensor for determining the height of the weight relative to the lift machinism. The weight is lowered by the lifting mechanism until it bears down upon the pellets, and then the cartridge is heated until the test substance melts. The weight is then used to extrude the melted substance through the plug orifice until it has fallen a certain distance, which operation is automatically timed by the computer. The time is then used in determining the melt index value for the substance. This operation is automatically repeated for all of the cartridges in the carousel.

An automatic cut-off mechanism is used to cut off excess extrudate, and an extrudate carousel is automatically advanced to collect separate samples of the used extrudate. Optical sensors are provided to determine the motions of the components of the apparatus.

11 Claims, 59 Drawing Sheets

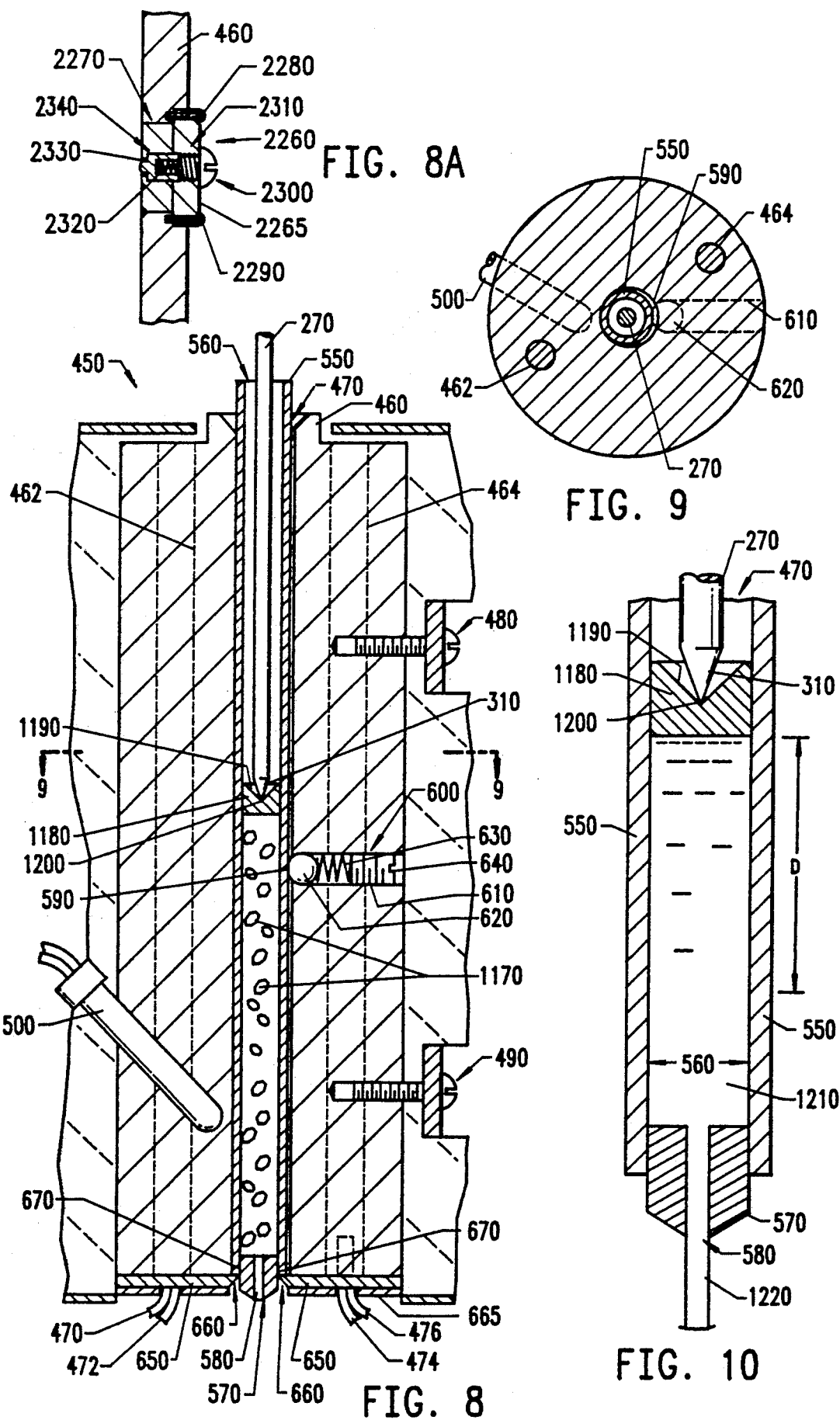

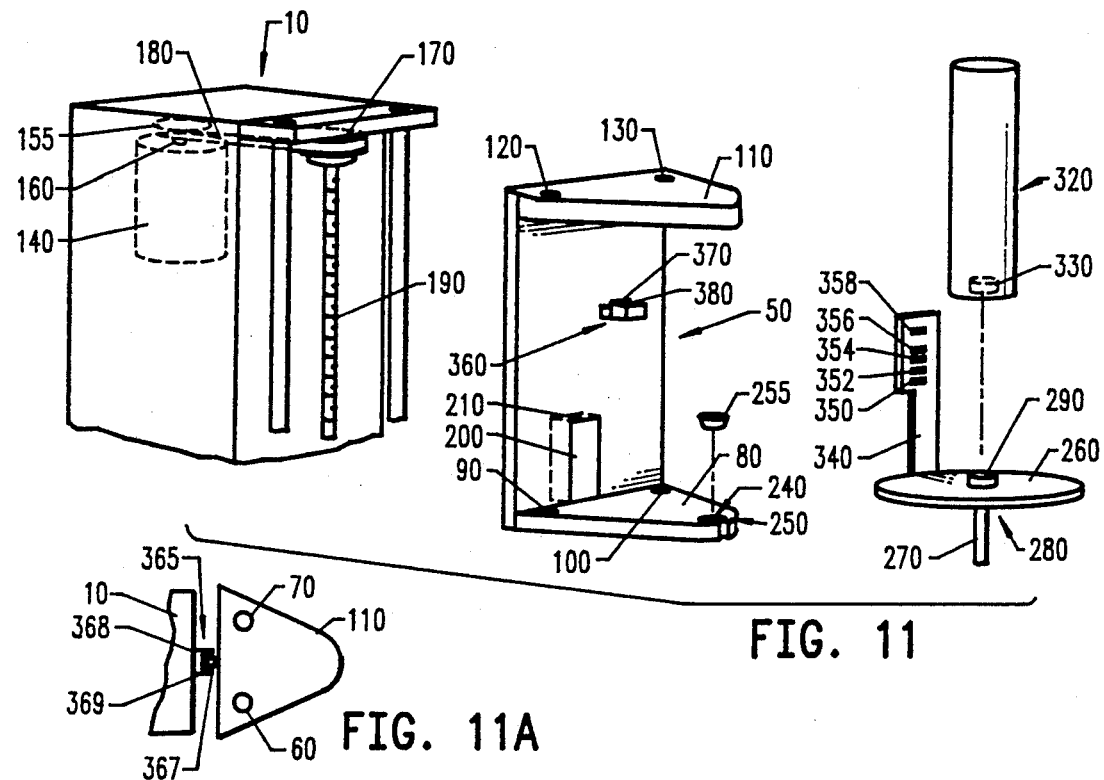
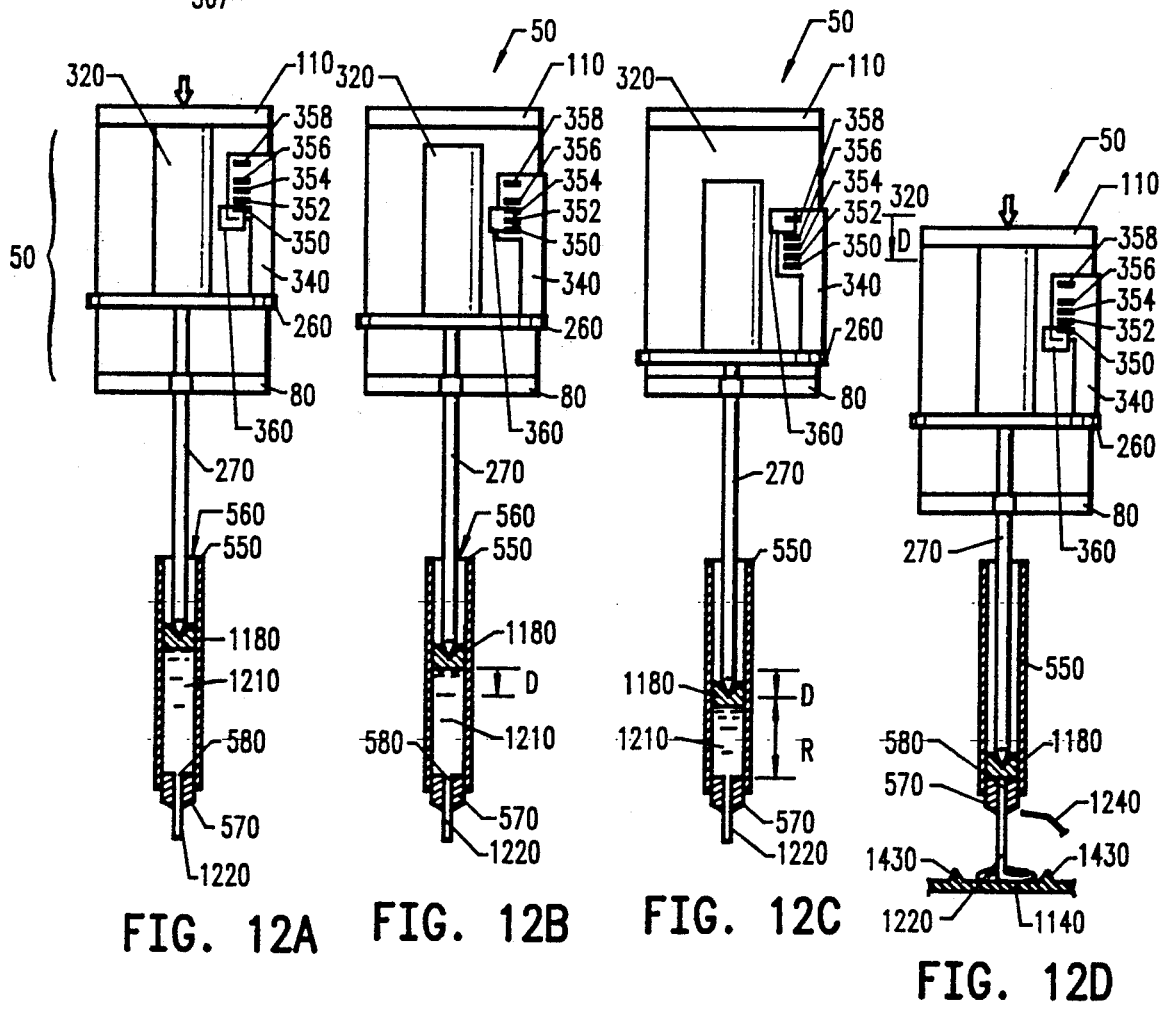
FIG. 11
FIG. 11A
FIG. 12A FIG. 12B FIG. 12C FIG. 12D

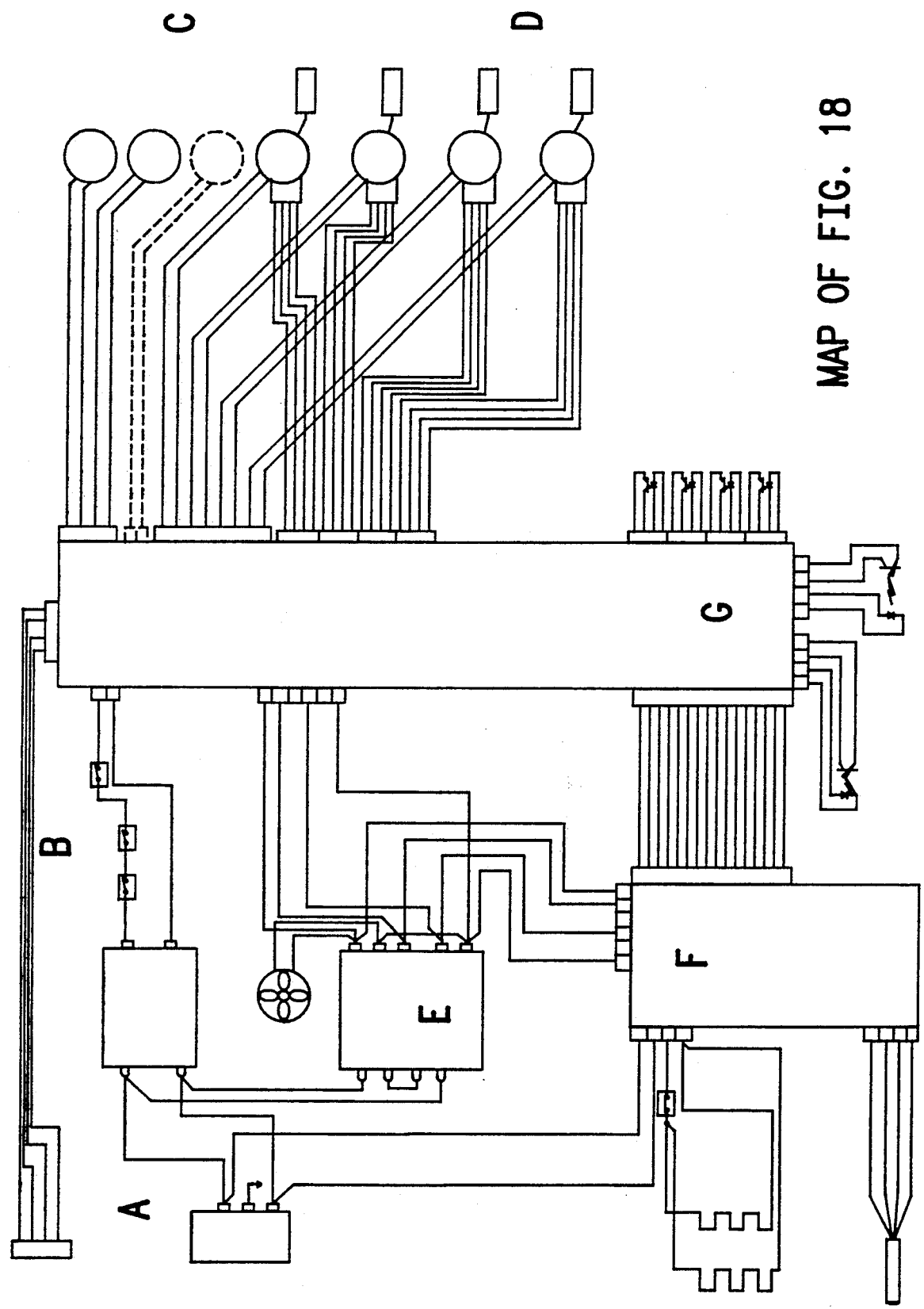
MAP OF FIG. 18

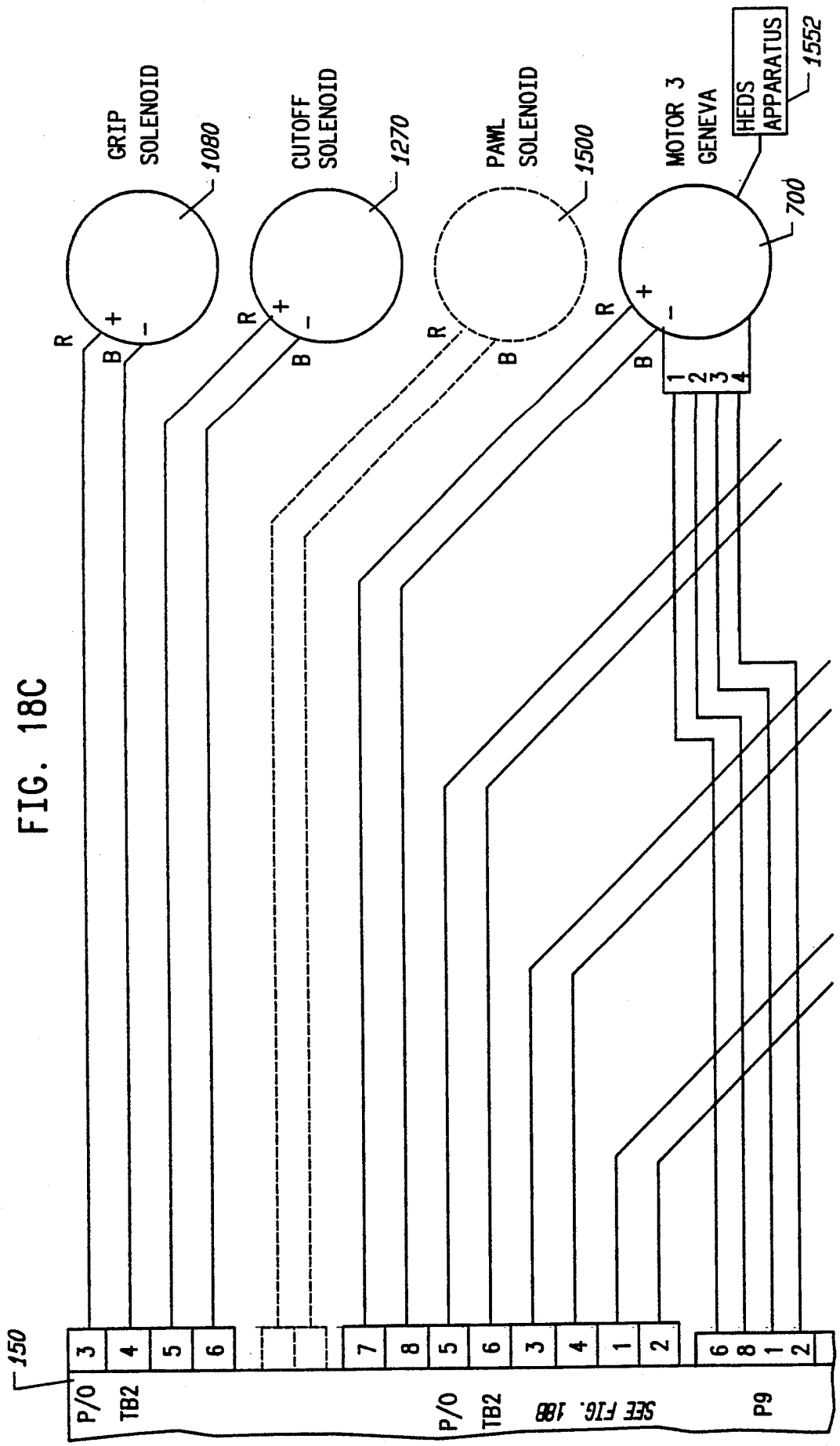

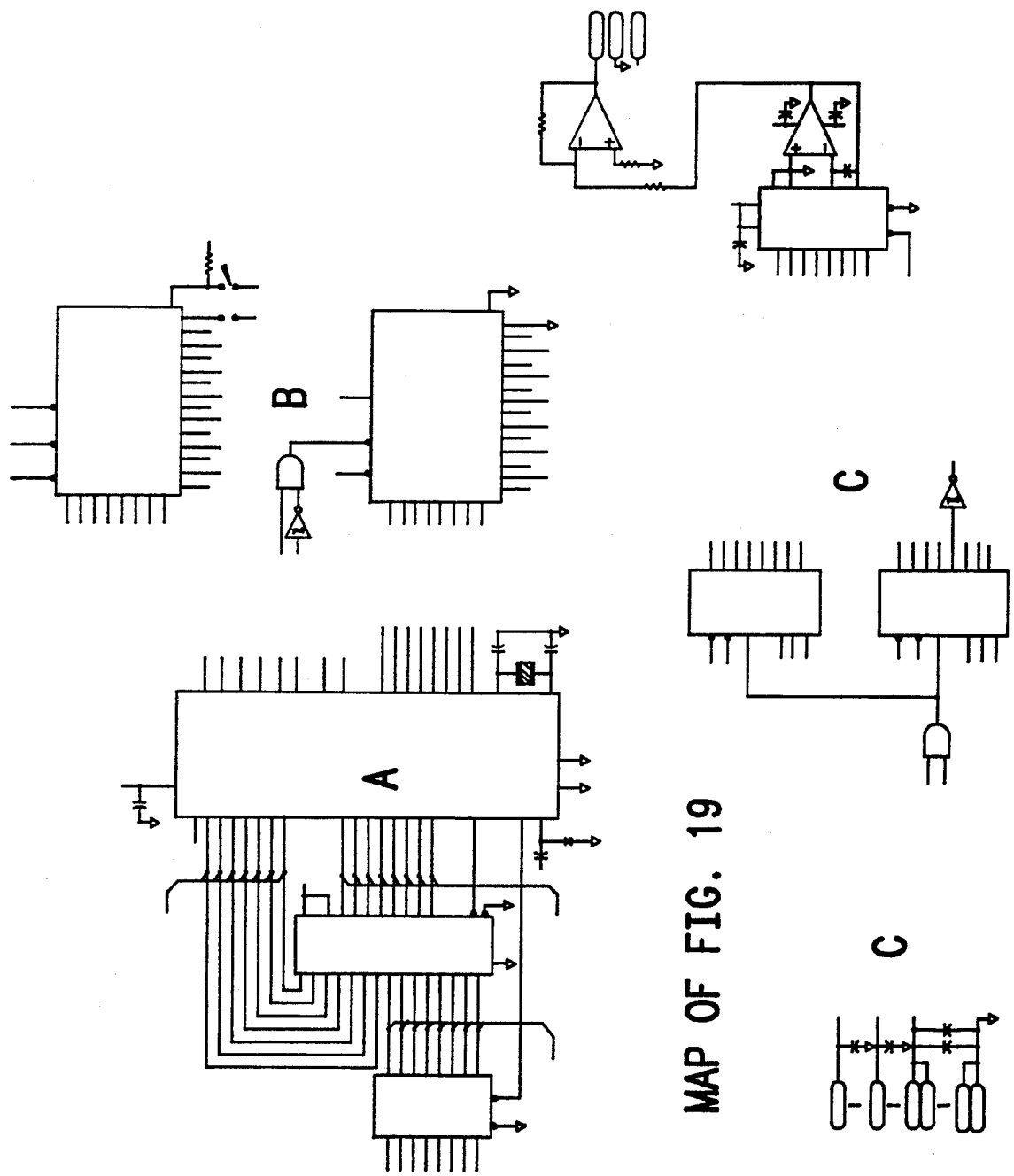
MAP OF FIG. 19

SEE FIG. 19C

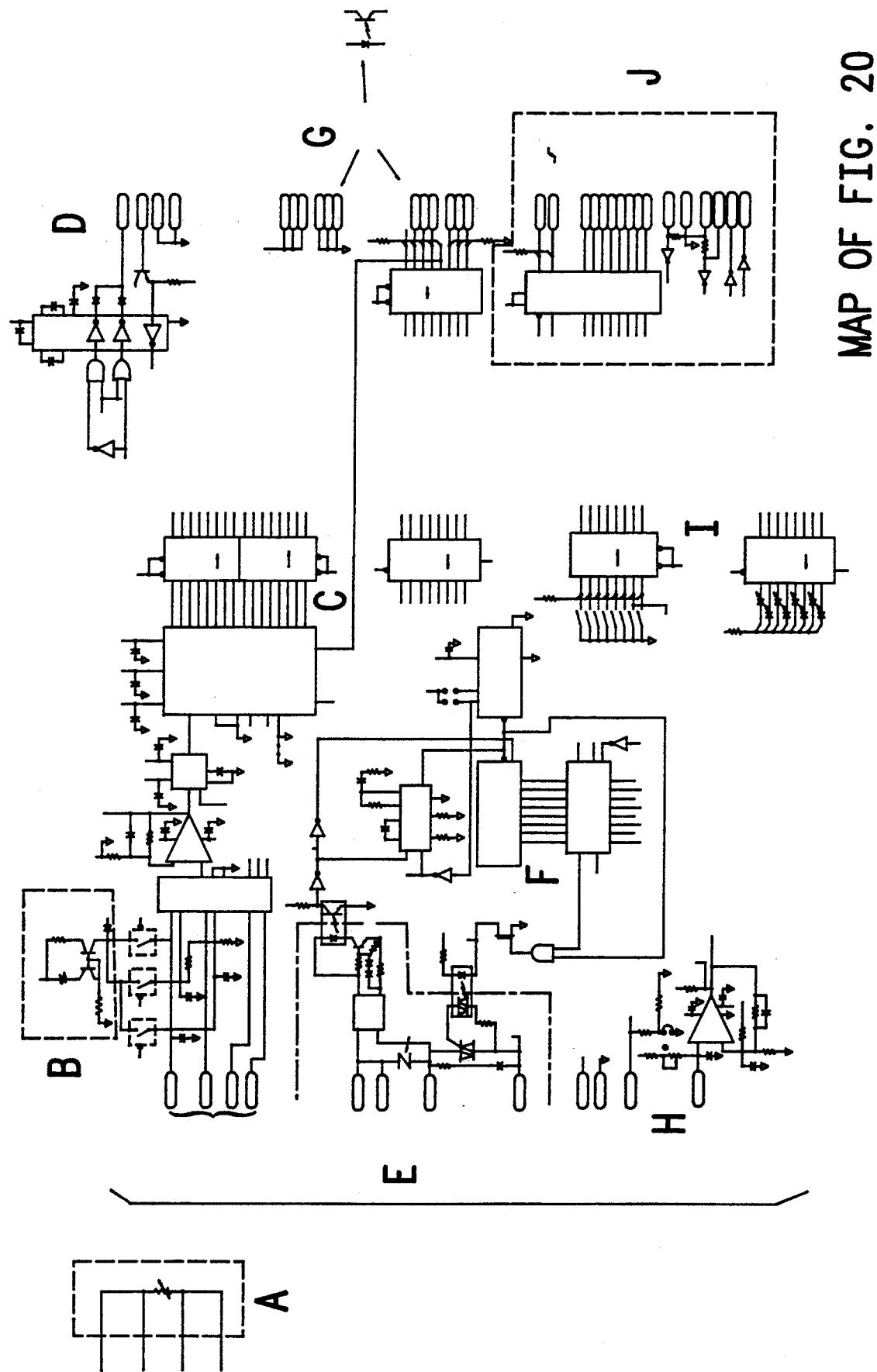

FIG. 20C
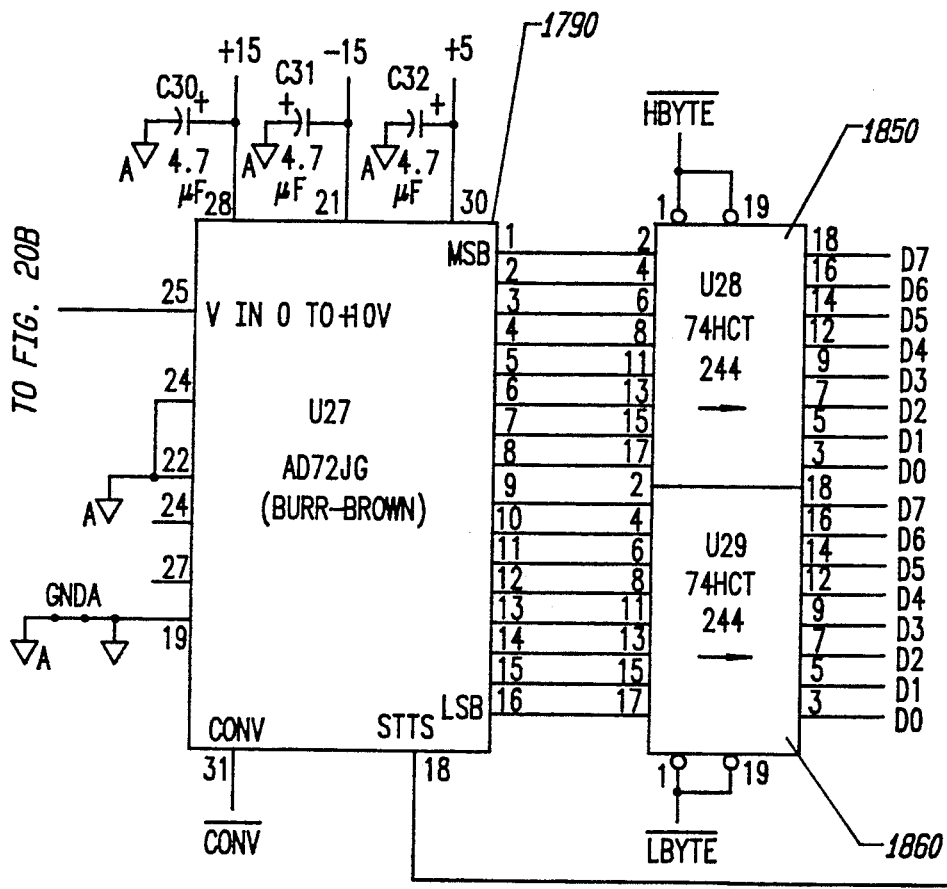
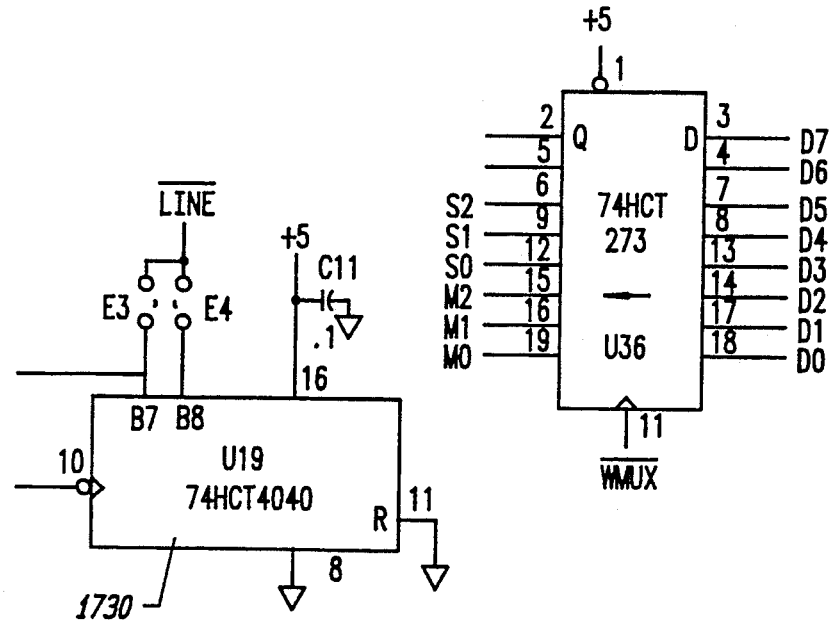
SEE FIG. 20I

FIG. 20E

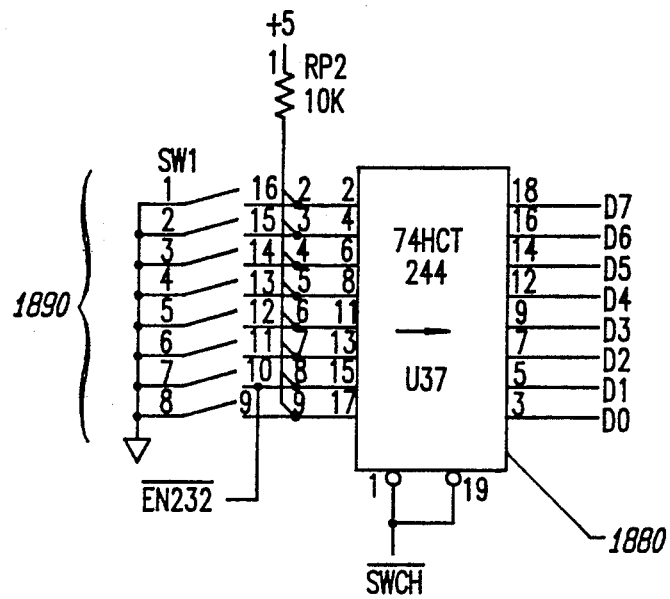
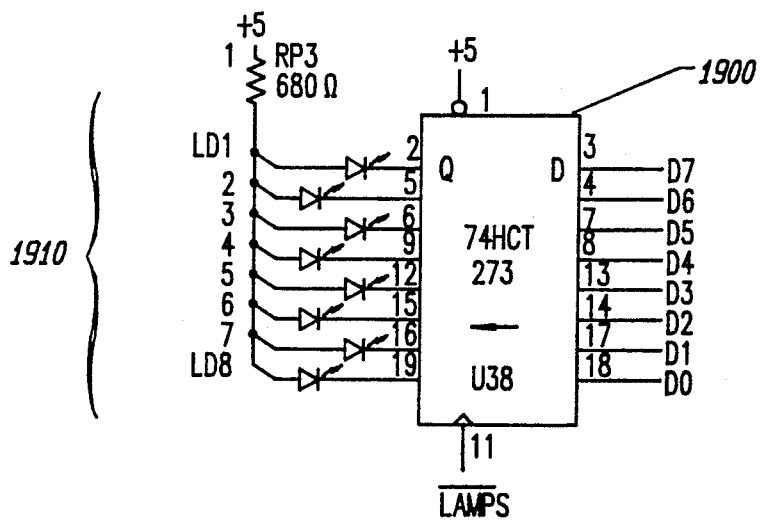
FIG. 20I

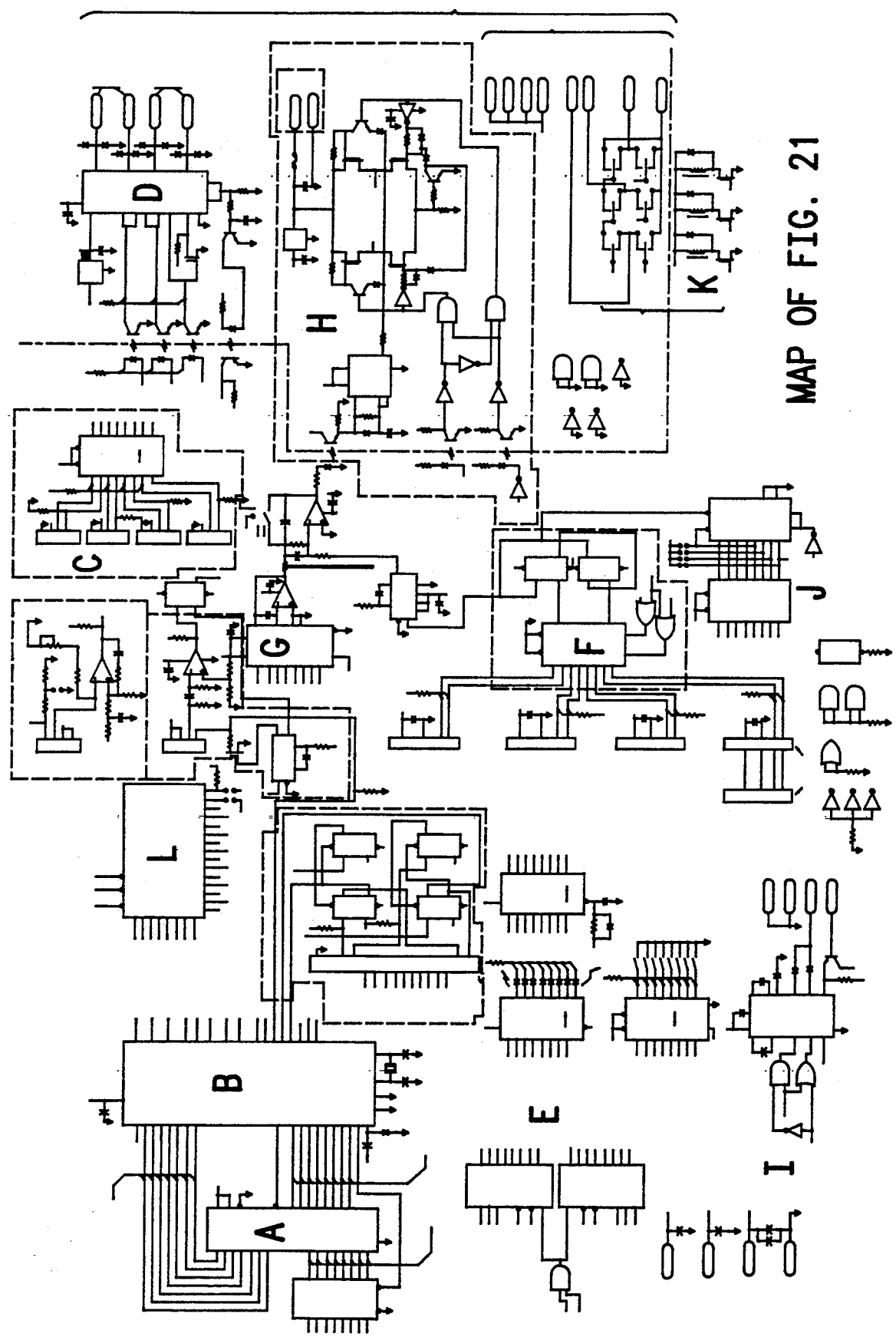
MAP OF FIG. 21

SEE FIG. 21E

```
========================================================
|   Setup For Channel 1                                 |
|            KD Group                                   |
|   2550 Wyandotte Street, Mountain View, CA 95070      |
|                                                       |
|   Operator ID: John Smith        Run Temp: 190 deg C  |
|   Project No: 21345               Weight: 2.16 kg     |
|   Job No: #X-256                  Cartridges: 5       |
|   Filename: chan1dat       Fri Sep 23,1988 16:43:47   |
|                                                       |
|   Cartridge No.    Sample ID          Density         |
|   ─────────────────────────────────────────────       |
|        1           Cartridge1          0.7000         |
|        2           Cartridge2          0.7100         |
|        3           Cartridge3          0.7200         |
|        4           Cartridge4          0.7000         |
|        5           Cartridge5          0.7200         |
|                                                       |
|                                                       |
|   Press F1 for Commands/Help                          |
========================================================
```

FIG. 27

```
┌──────────────────── Setup Help ────────────────────┐
│ This screen allows the information necessary to run a melt index │
│ to be entered.                                                    │
│                                                                   │
│   to move the highlight bar to select an item.                    │
│ Pressing ↵ will allow item to be modified.                        │
│ HOME and END will move the highlight bar to the first and last items. │
│                                                                   │
│ When an item is selected, a box is opened with the current value of the │
│ item highlighted. If this value is acceptable, pressing ↵ will    │
│ ,HOME,END,BACKSPACE                                               │
│   to move the cursor to the location to begin editing. To enter an entirely │
│ different value, simply start typing the new value. The highlighted │
│ value disappears and the new entry is displayed. When the entry is │
│ complete, press ↵. At any point in the entry process, pressing   │
│ ESC will abort the process and restore the original value.        │
│                                                                   │
│ The two lines of lab information at the top of the screen are stored │
│ by the system and do not have to entered each time.               │
│                                                                   │
│ The filename field is the name of the file where the melt index results │
│ will be stored.                                                   │
│                                                                   │
│ System date and time can be set from this screen.    Press ESC to exit help │
└───────────────────────────────────────────────────┘
```

FIG. 28

```
          Setup For Channel 1
         KD GROUP PETRON MI200
            Mountain View, CA.

Operator ID: John Smith          Run Temp: 190  deg C
Project No:  21345                 Weight: 2.16 kg
Job No:      #x-256             Cartridges: 5
Filename:    chan1dat           Mon Oct 10,1988 10:52:31

Cartridge No.      Sample ID              Density

1            Cartridge1             0.7000
      2            Cartridge2             0.7100
      3            Cartridge3             0.7200
      4            Cartridge4             0.7000
                                          0.7200

Enter Operator ID: John Sm

Press F1 for Commands/Help
```

FIG. 29

```
       Setup For Channel 1
       KD GROUP PETRON MI200
       Mountain View, CA.

Operator ID: John Smith       Run Temp: 190  deg C
Project No: 21345              Weight: 2.16 kg
Job No: #X-256                 Cartridges: 5
Filename: chan1dat             Mon Oct 10,1988 10:55:26

Cartridge No.    Select Weight         Density 1           325    g              0.7000
     2           1.00   kg             0.7100
     3           1.05   kg             0.7200
     4           1.20   kg             0.7000
     5           2.16   kg             0.7200
                 3.80   kg
                 5.00   kg
                 10.00  kg
                 12.50  kg
                 21.60  kg Press F1 for Commands/Help
```

FIG. 30

```
───── Setup For Channel 1 ─────
      KD GROUP PETRON MI200
        Mountain View, CA.

Operator ID: John Smith       Run Temp: 190   deg c
Project No: 21345              Weight: 2.16 kg
Job No: #X-256               Cartridges: 5
Filename: chan1dat           Mon Oct 10,1988 10:58:25

Cartridge No.     Sample ID           Density

1            Cartridge1          0.7000
     2            Cartridge2          0.7100
     3            Cartridge3          0.7200
     4            Cartridge4          0.7000
                       dge5           0.7200

┌─────────────────────┐
   │ Enter Density: 0.7  │
   │                     │
   └─────────────────────┘

Press F1 for Commands/Help
```

FIG. 31

═══ System Status ═══
KD Group
2550 Wyandotte Street, Mountain View, CA 95070

| Channel | # Tests In Run | # Tests Completed | Current Temp | Status |
|---|---|---|---|---|
| 1 | 5 | 3 | 190.02 | WORKING |
| 2 | 4 | 1 | 190.00 | PAUSED |
| 3 | 3 | 1 | 190.01 | ERROR |
| 4 | 24 | 24 | 190.02 | COMPLETE |
| 5 | 0 | 0 | 185.07 | IDLE |
| 6 | 0 | 0 | 100.67 | RESETING |
| 7 | 0 | 0 | 0.00 | CONNECTING |
| 8 | 0 | 0 | 0.00 | CONNECTING |

Press F1 for Commands/Help          Fri Sep 23, 1988  16:49:28

FIG. 32

```
 ┌─ Commands ─┐    ─ System Status ─
 │ Init. Communications │  KD GROUP PETRON MI200
 │ Help                 │  Mountain View, CA.
 └──────────────────────┘
```

| Channel | # Tests In Run | # Tests Completed | Current Temp | Status |
|---------|----------------|-------------------|--------------|--------|
| 1 | 5 | 3 | 190.02 | WORKING |
| 2 | 4 | 1 | 190.00 | PAUSED |
| 3 | 3 | 1 | 190.01 | ERROR |
| 4 | 24 | 24 | 190.02 | COMPLETE |
| 5 | 0 | 0 | 185.07 | IDLE |
| 6 | 0 | 0 | 100.67 | RESETING |
| 7 | 0 | 0 | 0.00 | CONNECTING |
| 8 | 0 | 0 | 0.00 | CONNECTING |

Press F1 for Commands/Help          Mon Oct 10,1988 10:08:26

FIG. 33

```
 ┌─── Commands ───┐ ──── System Status ─────────────────────────────

│ Init. Communications │
 │ Help                 │
 └──────────────────────┘

Channel   # Tests In Run   # Tests Completed   Current Temp   Status 1             5                  3              190.02      WORKING
    2             4                  1              190.00      PAUSED ──────────────────────── System Status Help ────────────────────────

This screen allows the entire system of melt index channels to be monitored.
 The current status of each channel is displayed.

To get more detailed information about an individual melt index channel,
 move the highlight bar, and then press J to
 select channel.

The Init. Communications command causes the system to determine how
 many active channels are connected. This can be used to bring another melt
 indexer on-line while a melt index is in progress.

Press ESC to exit help
```

FIG. 34

```
─────────────── Channel 1 Status ───────────────

Operator ID: John Smith                    Set Temp: 190.00
Project No: 21345                      Current Temp: 190.02
   Job No: #X-256                        Cartridges: 5

Status: WORKING                     Mon Oct 10,1988 10:10:58

Cartridge  Sample ID    Distance   Melt    Density      Result
  No.                    inches    Temp                Time    MI 1      Cartridge1     1.0     190.04   0.7000     70.01   0.32
    2      Cartridge2     1.0     190.01   0.7100     72.91   0.33
    3      Cartridge3     1.0     190.02   0.7200     70.12   0.32

Press F1 for Commands/Help
```

FIG. 35

```
═══ Commands ═══════ Channel 1 Status ═══════════════════
                                    Set Temp: 190.00
Emergency Stop                  Current Temp: 190.02
Pause After Cartridge              Cartridges: 5
Abort Cartridge
Abort Carousel                  Mon Oct 10,1988 10:46:31
Expand Error
Help
                Distance    Melt                   Result
                 inches     Temp    Density   Time     MI 1  Cartridge1   1.0    190.04   0.7000   70.01   0.32
    2  Cartridge2   1.0    190.01   0.7100   72.91   0.33
    3  Cartridge3   1.0    190.02   0.7200   70.12   0.32

Press F1 for Commands/Help
```

FIG. 36

METHOD AND APPARATUS FOR AUTOMATIC MELT INDEXING

BACKGROUND OF THE INVENTION

This invention relates to method and apparatus for determining melt index values for substances such as polymers, and in particular to a new method and apparatus for automatically determining such melt index values. In the present art, in order to conduct quality control on thermoplastics, the melt index value for the thermoplastic must be determined by a cumbersome and complicated manual process involving melting an amount of the substance, extruding it through an orifice, and determining the melt index for the extrudate. Such a manual process is set forth, for instance, in the American Society for Testing and Materials (ASTM) Designation D1238-85 entitled "Standard Test Method for Flow Rates of Thermoplastics by Extrusion Plastometer," which is incorporated herein by reference.

Where many thermoplastics must be tested, the present method and apparatus are inadequate, because they are slow, expensive and labor-intensive. Accordingly, a need has arisen for a fast, reliable automatic melt indexing method and apparatus.

Another disadvantage of the method and apparatus presently in use is that there is danger to the operator of coming into contact with heating units and molten thermoplastics. It is therefore an object of this invention to provide a melt index testing method and apparatus which minimize the risk of injury to workers.

When an operator of manual melt indexing apparatus conducts a test, several operations must be performed, including setting up a cylindrical cartridge with the test substance, melting the substance to form a molten resin, beginning the extrusion process by placing a weight so that it bears down on the resin, timing the extrusion rate through a given distance by using a stop watch or other timer, cutting off the extrudate with a screwdriver or blade, removing the used extrudate, etc. Another form of the test involves extruding the resin for a predetermined amount of time, and then weighing the extrudate to determine the melt index. Either of these involves many actions and chances for error on the part of the operator, and thus imprecision is a common problem in the field.

Accordingly, it is an object of this invention to provide a method and apparatus for automatic melt index testing, requiring little labor and providing high reliability, and in particular to provide such a method and apparatus which yield precise and highly repeatable results.

It is another object of the invention to provide such a method and apparatus which can be used for automatically testing a large number of thermoplastics without intervention by the operator.

SUMMARY OF THE INVENTION

The present invention comprises method and apparatus for automatic melt indexing, including a heater block with a central bore for receiving cartridges, one at a time, containing pellets of a substance to be tested. The apparatus is computer controlled. Each cartridge includes a plug at its lower end having an orifice therethrough. A rotatable carousel of cartridges is positioned adjacent the heater block, with the carousel carrying numerous such cartridges. A transfer arm is provided for grasping the cartridges and transferring them to the heater block. Each cartridge includes a piston on top of the pellets of the substance to be tested.

A lift mechanism is positioned above the heater block, and carries a weight on top of a tamping rod. Once the cartridge of pellets is in place, the tamping rod is lowered to compact the pellets. The lift mechanism is then raised, and the cartridge is heated by contact with the heating block, which is preheated to the desired temperature by means of heating elements carried therein. The cartridge is heated for a predetermined period of time or until the desired temperature is reached. Then the lift mechanism is used to force some of the now-molten substance through the orifice of the plug, and then, by allowing the weight to bear upon the molten substance, to cause the molten substance to extrude through the orifice until the piston has traveled through a given, predetermined distance.

The lift mechanism includes a flag with windows coupled to an optical sensor for determining the distance through which the lift mechanism has passed, thus determining the length of the cartridge from which the thermoplastic has been extruded. The computer automatically determines the amount of time taken for the piston to travel through the predetermined distance. This value is then used to determine the melt index value for the thermoplastic in question.

The cartridge carousel is automatically rotated by a motor controlled by the computer, and utilizes a Geneva mechanism for rotating the carousel in an indexed fashion. An optical sensor is provided to indicate a "home" position for the carousel. Similarly, optical sensors are provided on the lift mechanism and the transfer arm to indicate their home positions.

Another optical sensor is provided on a clamping mechanism of the transfer arm to indicate whether a cartridge has been clamped.

An extrudate carousel is positioned beneath the cartridge, and is operated automatically by a computercontrolled solenoid. The extrudate carousel includes ratchet teeth around its periphery, and a pawl controlled by the solenoid drives the teeth.

A cut-off mechanism with an upwardly angled blade is positioned near the bottom of the plug of the cartridge in the heater block, such that when a given test is performed, the cutting mechanism activates a solenoid thereof to cause the cutting blade to cut off the remaining extrudate. This extrudate then falls into the extrudate carousel, and the pawl is activated to turn the extrudate carousel to a new position.

Once a test is performed in a given cartridge, it is replaced into the cartridge carousel, and a new cartridge is automatically placed into the heater block. When the computer detects that no more cartridges are present in the cartridge carousel, or that it has conducted a predetermined number of tests (chosen by the operator of the equipment), it stops the automatic testing. The cartridge carousel may then be replaced with another cartridge carousel of thermoplastic pellets or other substances to be tested.

BRIEF DESCRIPTION OF THE DRAWINGS

FIG. 8 is a sectional view taken along line 8—8 of FIG. 4.

FIG. 8A is a sectional view of an alternative embodiment of a locking mechanism of the invention.

FIG. 9 is a sectional view taken along line 9—9 of FIG. 8.

FIG. 10 is an enlarged sectional view of a portion of FIG. 8 showing the conducting of a melt index test.

FIGS. 11 and 11A show an exploded view showing details of the upper portion of the apparatus of FIG. 2.

FIGS. 12A-12D show a sequence of positions for the apparatus of FIG. 2 during the conducting of a melt index text.

FIG. 18 and 18A-18G show a wiring diagram, in block form, for the apparatus of the invention.

FIGS. 19, 19A-19C, 20, 20A-20J, 21, 21A-21L are schematic diagrams for the apparatus of the invention.

FIGS. 25-37 are exemplary screens from a particular embodiment of software code relating to the invention.

DESCRIPTION OF THE PREFERRED EMBODIMENTS

Figures 1, 2, 3:
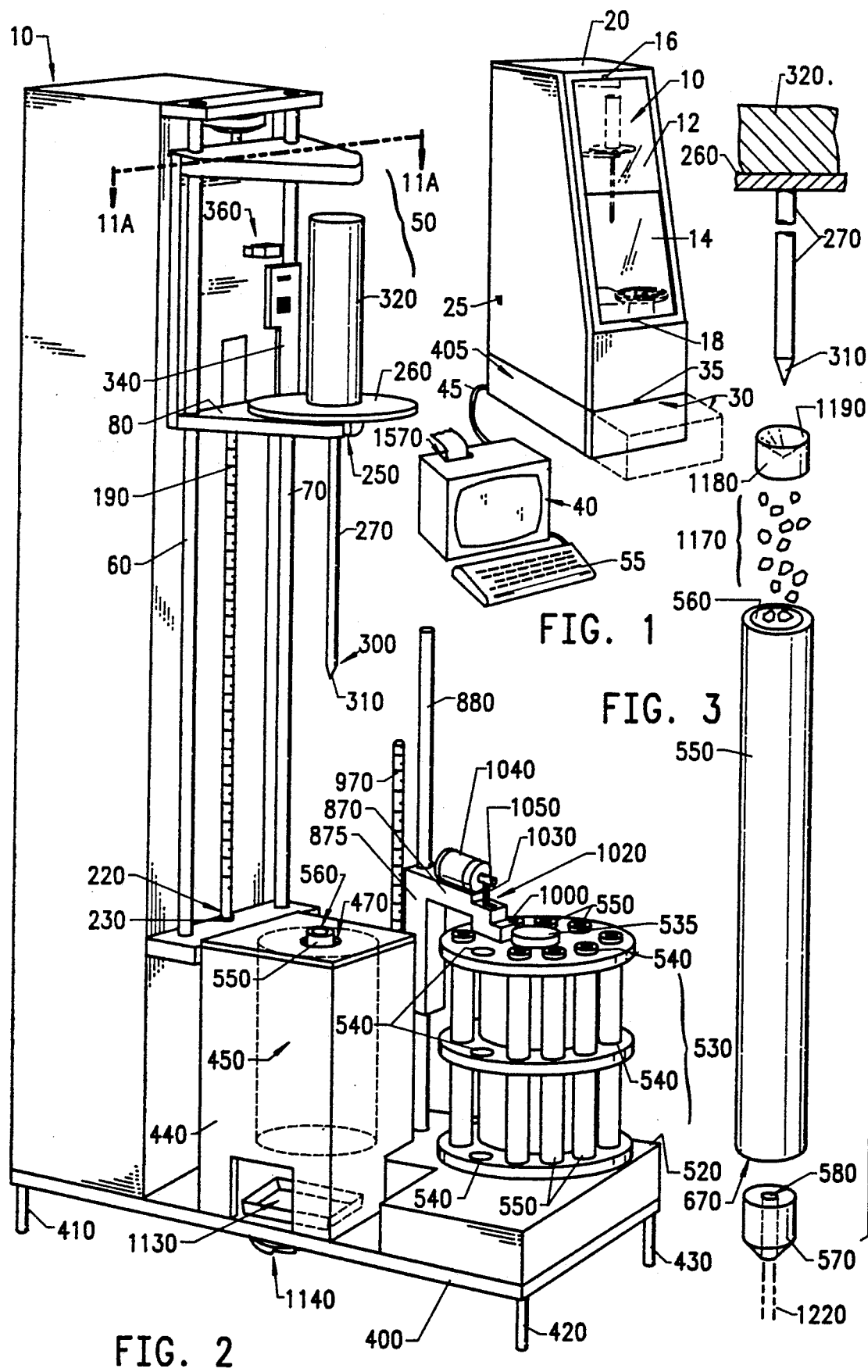
FIG. 1 is a perspective view showing a melt indexer system according to the present invention.
FIG. 2 is a perspective view of an automatic melt indexer unit according to the invention.
FIG. 3 is an exploded view showing a cartridge utilized in the invention.

FIGS. 1 and 2 show a melt indexer unit 10 according to the present invention, which, as shown in FIG. 1, is preferably positioned within a housing or cabinet 20 having a drawer 30, which is shown in both its closed position and (in dotted fashion) in its open position. A microcomputer 40 (such as an IBM AT personal computer) or other processor is electrically coupled to the unit 10 by conventional means such as a cable 45. The housing 20 includes windows 12 and 14 which can be opened and closed by sliding them up and down.

Both the microprocessor 40 and the unit 10 are powered by a conventional A.C. power source (not separately shown), and the unit 10 is switched on by a power switch 25. The microprocessor 40 is used for controlling the steps of the method of the present invention automatically, as described below.

The unit 10 includes a lift mechanism 50 slidably carried on two vertical bars 60 and 70. Referring to FIG. 11, the lift mechanism 50 includes a lower platform 80 having bores 90 and 100 therethrough and an upper platform 110 having bores 120 and 130 therethrough. Bore 120 is vertically aligned with bore 90 and bore 130 is vertically aligned with bore 100, for receiving the bars 60 and 70, respectively.

Carried within the unit 10 is a lift motor 140, as shown in FIG. 11 and in the wiring diagram of FIG. 18. The lift motor 140 is controlled by a motor control unit 150, in a manner to be described in detail below. The lift motor 140 has an output pulley 155 connected to a shaft 160, and rotatably mounted on the unit 10 is a lift pulley 170, which is coupled to the pulley 155 by means of a belt 180. Attached to the pulley 170 is a threaded shaft 190.

The lift mechanism 50 carries a lift coupler 200 having a threaded bore 210, which threadedly receives the shaft 190. The shaft 190 is rotatably supported at its lower end 220 by a bearing 230. The coupling of the lift mechanism 50 and the threaded shaft 190 is such that, when the pulley 170 rotates in one direction (such as clockwise as viewed from above), the mechanism 50 is raised, and when the pulley 170 rotates in the other direction, the mechanism 50 is lowered.

The lower platform 80 of the mechanism 50 includes a bore 240 and a slot 250. A weight tray 260 is rigidly attached to a tamping rod 270, having an upper end 280 with a knob 290, and a lower end 300 with a point 310. A weight 320 is carried on the tray 260, and has a countersink 330 for receiving the knob 290. The tray 260 is placed upon the platform 80 by passing the tamping rod 270 through the slot 250, and then resting the tray 260 on top of the platform 80, with the tamping rod 270 extending through the bore 240. The bore 240 has a diameter which is somewhat larger than the diameter of the rod 270, so that there is little frictional resistance to vertical motion of the rod 270 relative to the bore 240.

In an alternative embodiment, not separately shown, the slot 250 is omitted, and the tamping rod 270 is passed through the bore 240 from above. Whether or not a slot is included, it is preferable that the bore 240 have a countersunk shape, i.e. is broader at its top and bottom than at its center as shown in FIG. 11, to minimize frictional contact between the bore 240 and the rod 270. A bushing or bearing 255 may be provided as shown in FIG. 11, having a central bore through which the tamping rod 270 is placed.

A flag 340 having windows 350, 352, 354, 356 and 358 is mounted on the weight tray 260. A photosensor unit 360 is mounted on the mechanism 50, and includes legs 370 and 380. The flag 340 is configured such that the windows 350-358 pass between the legs 370 and 380. The photosensor unit 360 (which may be referred to as a drop sensor) is coupled to motor control unit circuitry 390 as shown in FIG. 21, at the top thereof. The drop sensor 360 is utilized to detect the height of the tray 260, and hence the height of the tamping rod 270, by detecting when windows 350-358 are aligned with the legs 370 and 380. The drop sensor 360 may be a conventional photosensing apparatus.

As shown in FIG. 11A, the unit 10 includes a photosensor unit 365 having legs 368 and 369, and the lift mechanism 50 carries a flag 367 which is positioned between the legs 368 and 369 when the mechanism 50 is in its home position depicted in FIG. 11. The unit 365 is coupled to the motor control unit 150, as shown in FIGS. 18 and 21, and may be a conventional optical interruption detector.

The melt indexer unit 10 includes a base 400 supported by legs such as legs 410, 420 and 430. The base 400 may alternatively be supported by a flange or other means carried by the housing 20. In either case, the base 400 is positioned such that it is situated above a drawer enclosure 405 shown in FIG. 1, where the enclosure 405 carries the drawer 30.

A heater housing 440 is mounted on the base 400 and carries a heating unit 450, which includes a heater block 460 (preferably formed from copper for good heat transfer characteristics), which carries heater elements 462 and 464 coupled to a source of electricity by means of wires 470 and 472, and 474 and 476, respectively. The heater elements 462 and 464 may have a standard resistance heater design.

The heater block 460 includes a vertical bore 470 which is substantially coaxial with the tamping rod 270 when the weight tray 260 is mounted on the lower platform 80, as shown in FIGS. 1, 8 and 12A–12D. The heater block 460 is fixed within the heating unit 450 by means of bolts 480 and 490. A thermometer 500 is carried within the heater block 460, and is preferably a conventional platinum resistance thermometer, which has a resistance which depends upon temperature. As shown in the wiring diagram of FIG. 18, the thermometer 500 is electrically coupled to a temperature control unit 510, which energizes heaters 462 and 464 to a predetermined temperature, as detected by the thermometer 500. The predetermined temperature may be varied, depending upon the application desired by the operator of the melt indexer unit 10. Typically, the thermometer 500 will be calibrated such that the various resistances are known to correspond with particular temperatures.

Figures 4, 5, 6, 7:
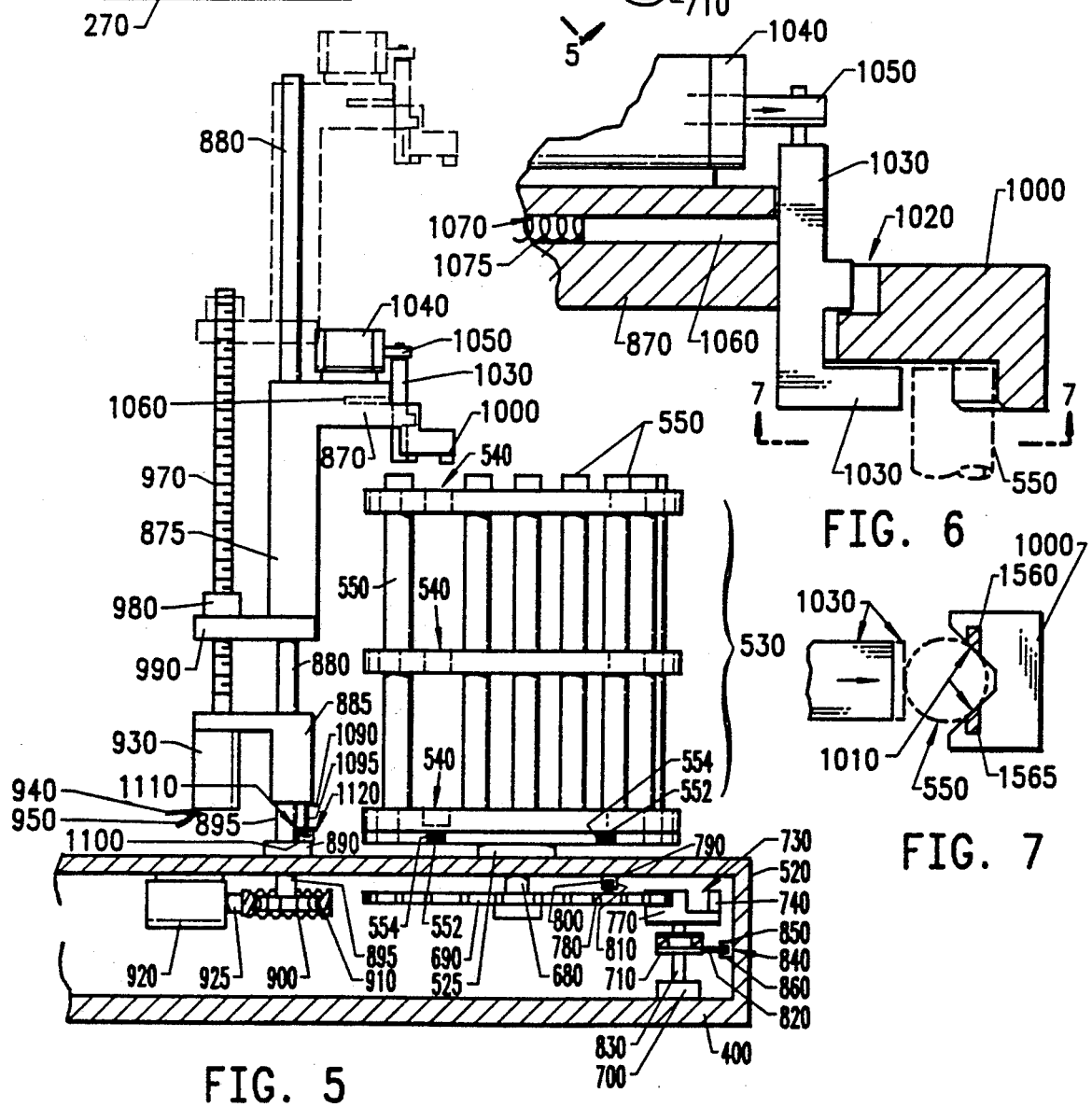
FIG. 4 shows the driving mechanism for a carousel used in connection with the invention.
FIG. 5 is an elevation, partly in section, taken along line 5—5 of FIG. 4.
FIG. 6 is a sectional view taken along line 6—6 of FIG. 4.
FIG. 7 is a view taken along line 7—7 of FIG. 6.

The base 400 also carries a carousel platform 520 upon which a carousel 530 is rotatably mounted, as shown in FIGS. 2 and 5. The carousel 530 includes a plurality of bores 540 for receiving cartridges 550. The carousels 30 is mounted on a central shaft 535, which is connected to the shaft 680, and is supported on the carousel platform 520 by a bearing 525. The carousel 530 may be removed from the shaft 535 and replaced, such that a carousel full of cartridges 550 may easily be replaced by another such carousel. The carousel 530 and shaft 535 are configured such that one does not rotate relative to the other, such as by providing the shaft 535 with an asymmetrical cross section or by utilizing a key on the shaft 535 or on the carousel (not separately shown). The cartridge 550 may be of metal or some other material with a relatively high melting point and relatively high heat conductivity.

In an alternative embodiment as shown in FIG. 5, the carousel 530 may be placed on a carousel support 540, which is itself coupled to the shaft 680. The carousel 535 may be provided with pins 552 on a bottom surface thereof, and the platform 554 is provided with recesses 554 to match the configuration of the pins 552, so that the carousel may be placed on the platform at only one angle. This makes the relationship between the home position for the carousel 530 and the first cartridge 550 to be tested unambiguous.

Each cartridge 550 includes a central bore 560, and is adapted to fit within the bore 470 in a substantially coaxial fashion, as shown in FIG. 8. Carried at the bottom of each cartridge 550 is a plug 570 having a central orifice 580 which is substantially coaxial with the cartridge 550. The heater block 460 carries an adjustable spring-loaded locking mechanism 600 comprising a lateral bore 610, a ball 620, a spring 630, and a means for adjusting the force or tension of the mechanism 600 such as a threaded adjustment screw 640. Thus, when a cartridge 550 is inserted into the bore 470, the ball 620 is slightly displaced to the right as viewed in FIGS. 8 and 9, and when the cartridge 550 is inserted all the way into the bore 470, it is held in place by the locking mechanism 600.

An alternative embodiment to the locking mechanism 600 is the mechanism 2260 shown in FIG. 8A. This includes a plate 2265 mounted in a bore 2270, and held in place to the block 460 by fasteners such as bolts 2280 and 2290. A screw 2300 is threaded into a threaded bore 2310 in the plate 2265, and urges a spring 2320 towards the left, which in turn urges a plunger 2330 towards the left and into contact with the cartridge 550. The plunger 2330 is slidably carried in an unthreaded bore 2340 of the plate 2265, and includes a flat end for good contact with the cartridge 550.

Preferably, a plate such as steel plate 650 is affixed to the bottom of the heater block 460, and has an annular flange 660 surrounding the bore 470. The plate 650 preferably has a heater block insulator 665 attached to an underside thereof. The cartridge 550 is configured such that its lower end 670 abuts the flange 660 when the cartridge 550 is inserted all the way through the bore 470, for a positive positioning of the cartridge.

In either of the embodiments of FIGS. 2 and 5, the carousel 530 is coupled to a shaft 680, which is in turn coupled in a fixed manner to a wheel 690, called a star wheel. The coupling is such that, when the wheel 690 rotates, the shaft 680 and thence the carousel 530 are also rotated, in the same direction. A star wheel motor 700 drives a pulley 710, which is coupled via a belt 720 to a rotator 730. Coupled to the rotator 730 is a vertical pin 740. The star wheel and its related components comprise a standard Geneva mechanism.

As shown in FIG. 4, the star wheel 690 has alternating arcuate slots 750 and longitudinal slots 760. The rotator 730 includes a cam 770, and is configured such that, as the rotator is rotated by the star wheel motor 700 via the pulley 720, the cam 770 and the pin 740 alternately fit into the slots 750 and 760, respectively. As can be seen from FIG. 4, one rotation of the rotator 730 causes the star wheel 690 to rotate by exactly the distance between two arcuate slots 750. This angular distance is the same as the angular distance between bores 540 in which the cartridges 550 rest.

The star wheel 690 carries a flag 780, and mounted on the platform 520 is a conventional photosensor unit 790, as shown in FIGS. 4 and 5. The unit 790 may be identical to the unit 360, and, as shown in FIGS. 18 and 21, is coupled to the motor control unit 150. The unit 790 includes legs 800 and 810, and detects when the flag 780 passes between these legs. In the preferred embodiment only a single flag 780 is utilized on the star wheel 690, such that the unit 790 detects a single rotational position for the star wheel 690, which shall be referred to as the "home" position.

A flag 820 is also carried on the pulley 710, as shown in FIG. 5, or may alternatively be carried on a shaft 830 of the star wheel motor 700. Another conventional photosensor unit 840 having legs 850 and 860 is mounted on the platform 520, and detects when the flag 820 passes there between. The unit 840, which may be referred to as the Geneva index photosensor unit, is (as shown in FIGS. 18 and 21) coupled to the motor control unit 150. The Geneva index photosensor unit 840 detects each time the rotator 730 makes a single rotation, and thus can be used to count the number of rotations (and hence the number of arcuate slots 750 or cartridges 550) the star wheel 690 has moved from its home position.

The unit 10 includes a transfer arm 870 rigidly attached to a support 875, with the support 875 being slidably mounted on a shaft 880. The shaft 880 is mounted on a support 885. The support 885 is rigidly mounted on a shaft 895, which is rotatably carried by the carousel platform 520 at a bearing 890. Attached to the lower end of the shaft 895 is a gear 900.

An angle control motor 920 is carried by the platform 520, and drives a shaft 925 with a worm 910, which is coupled to the gear 900 such that the gear 900 is rotated as the motor 920 rotates the worm 910. When gear 900 is rotated, shaft 895 is thereby also rotated, which rotates support 885.

A transfer arm height control motor 930 is connected to the support 885, and is powered by means of wires 940 and 950. As shown in FIGS. 18 and 21, motors 140, 700, 920 and 930 are all connected via buffering and logic circuitry 960 to the motor control unit 150.

The motor 930 drives a threaded shaft 970, which engages an internally threaded bushing 980. The bushing 980 is attached to an arm 990, which is in turn attached to the support 875. As the shaft 970 is rotated by the motor 930, the coupling with the bushing 980 causes the transfer arm 870 to raise and lower accordingly, as indicated in dotted fashion in FIG. 5.

The transfer arm 870 includes a rigidly mounted gripper foot 1000 having a cartridge-receiving recess 1010, as shown in FIGS. 2, 5, 6 and 7. The transfer arm 870 includes a slot 1020 (shown in FIGS. 2 and 6) in which a cartridge grip 1030 is slidably positioned.

Figure 22:
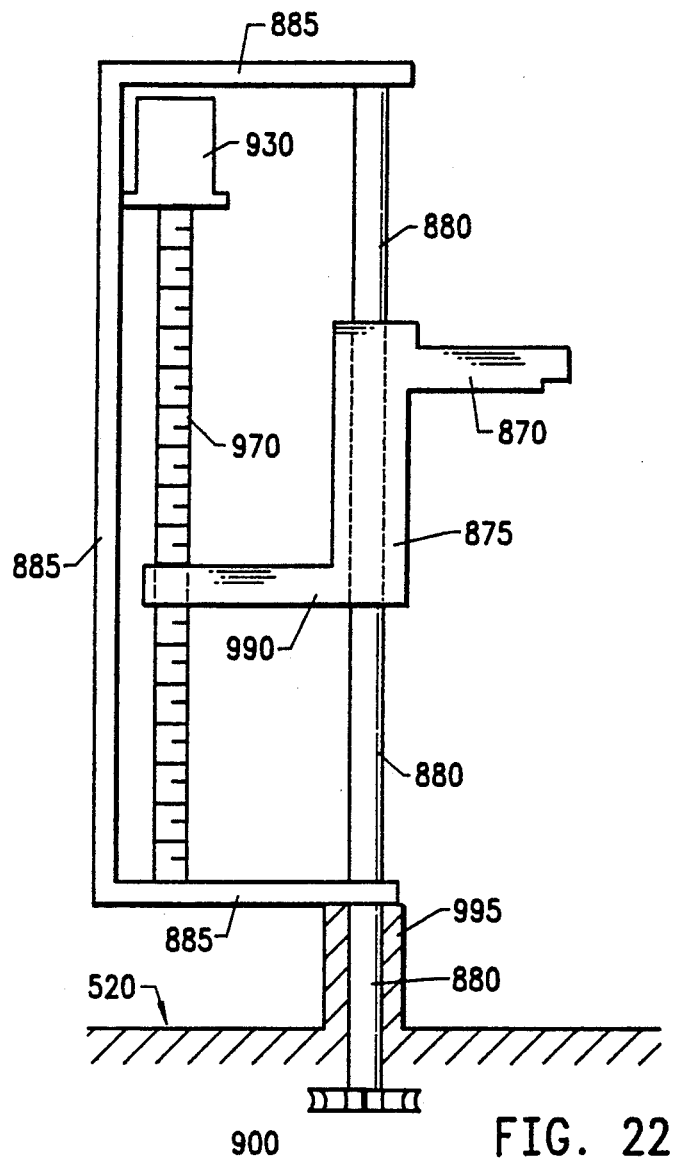
FIG. 22 shows an alternative embodiment of the transfer arm mechanism shown in FIG. 5.

In the alternative embodiment of FIG. 22, where analogous parts are numbered the same as in FIG. 5, the transfer arm 870 is carried by the support 875, which is in turn threadedly carried by the threaded rod 975 by means of the arm 990, which is internally threaded where it is supported by the rod 970. The motor 930 is in this case mounted at the top of the rod 970, and rotates it as in the embodiment of FIG. 5. The motor 930 and rod 970 are carried by the support 885, which extends around the rod 970 and transfer arm 870 and is nonrotatably connected to the top of the shaft 880. The shaft 880 extends through a support 995 which may be integral with the platform 520. Thus, rotation of the gear 900 rotates the support 885 and the structures supported thereby.

A grip solenoid 1040 is carried on the transfer arm 870, and includes a ram 1050 which is connected to the cartridge grip 1030, and controls its sliding motion. The grip 1030 includes a guide rod 1060 disposed in a bore 1070 of the transfer arm 870, for stabilizing the sliding motion of the cartridge grip 1030. As shown in FIGS. 18 and 21, the grip solenoid 1040 is electrically coupled to the motor control unit 150. A spring 1075 is disposed within the bore 1070, and urges the rod to the right as viewed in FIG. 6. When the solenoid 1040 is energized, the rod 1060 moves to the left so that the grip foot 1000 and the grip 1030 may receive a cartridge 550. When the solenoid 1040 is de-energized, the grip 1060 moves back to the right, due to force from the spring 1075.

The support 885 carries on an underside 1090 thereof a flag 1095. Mounted on the bearing 890 is a photosensor unit 1100 having legs 1110 and 1120. The unit 1100 is of conventional design, and may be identical to the units 360, 365, 790 and 840. The sensors 360, 365, 790, 840 and 1100 may be the GE H21A3 units produced by General Electric.

The bearing 890 is nonrotatably attached to the carousel platform 520, so that, as the motor 920 rotates the worm 910, the shaft 895 and the support 885 are rotated, thus moving flag 1095 into and out of alignment between the legs 1110 and 1120 of the photosensor unit 1100. Thus, there is one position for the support 885 and hence also for the transfer arm 870, wherein the flag 1095 is between the legs 1110 and 1120, which may be referred to as the transfer arm home position, as shown in FIGS. 4 and 5.

Stops 1122 and 1124 (see FIG. 4) may be mounted on the platform or otherwise carried by the unit 10 near the transfer arm 870 for limiting its angular range of movement. Thus, for instance, stop 1122 defines the counterclockwise-most rotation of the arm 870 (the "home" position), and the stop 1124 defines the clockwisemost rotation. These stops may be adjustable, such as by providing them with cam-shaped cross sections, and providing bolts 1126 and 1128 for tightening the stops 1122 and 1124, respectively, in any one of a variety of positions.

Figure 14:
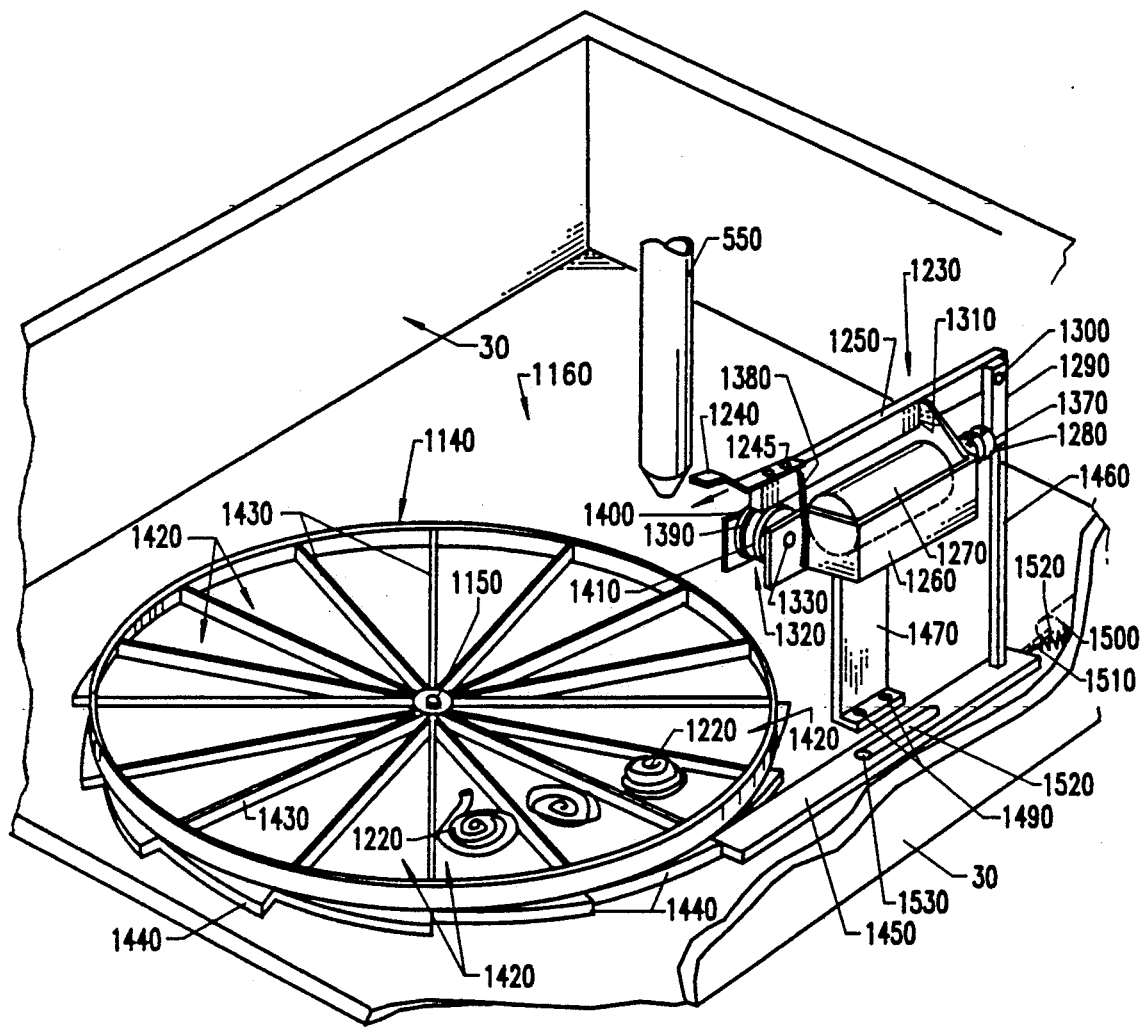
FIG. 14 is a perspective view of a cutting mechanism and carousel used in conjunction with the apparatus of FIG. 2.

The base 400 includes an aperture 1130, below which is positioned an extrudate carousel 1140, as shown in FIG. 2 and depicted in detail in FIG. 14. The extrudate carousel 1140 is preferably rotatably mounted on a pin 1150, as shown in FIG. 14, which is carried on a bottom surface 1160 of the drawer 30, as shown in FIGS. 2 and 14.

The following is a description of a single typical melt indexing test, after which the method for automatic multiple melt index testing will be described. The test is preferably in compliance with the above-mentioned ASTM Designation D1238-85.

In order to test a particular polymer or other substance, pellets or particles 1170 of the substance are loaded into a cartridge 550, as shown in FIG. 3, and the cartridge 550 is placed into the bore 470 of the heater block 460. A piston 1180 is placed on top of the particles 1170, and, as shown in FIGS. 3 and 8, has an outer diameter which closely matches an inner diameter of the cartridge 550. The piston includes a concave conical depression 1190 having a point 1200 for accommodating the point 310 of the tamping rod 270.

The particles 1170 are tamped down in a "cold tamp" by causing the lift motor 140 to rotate the threaded shaft 190 such that the lift mechanism 50 lowers until the point 310 contacts the depression 1190 of the piston 1180, as shown in FIG. 8. The lift mechanism 50 is lowered past the point where point 310 makes contact with the depression 1190 such that the lower platform 80 moves away from the weight tray 260 (taking the configuration shown in the upper portion of FIG. 12A), thus causing weight 320 to bear upon the particles 1170 and to be forced downwards by the upper platform 110, thereby compacting the pellets 1170 tightly.

The lift mechanism 50 is then raised, removing the weight from the particles 1170. The heating elements 462 and 464 are preferably preheated, i.e. are energized at the time of first powering up the equipment. The heating elements 462 and 464 are energized to the extent necessary to maintain the temperature within the heater block 460 at a desired predetermined level, as detected by the platinum resistance thermometer 500 (with the desired temperature being chosen by the operator). The resistance heaters 462 and 464 may be energized either manually by throwing a switch (not separately shown), or by means of a processor command, where the command is either given automatically by the microprocessor 40 or is entered on a keyboard 55 by the operator of the unit 10. In the preferred embodiment, however, the heater elements 462 and 464 are on whenever the unit 10 is provided with power.

When the temperature has reached the predetermined level, this is detected by the temperature control unit 510 (shown in FIG. 18), and the temperature is automatically maintained constant by the microprocessor 40, acting in conjunction with the thermometer 500. Alternatively, a predetermined length of time may be waited to allow the temperature to reach the desired level.

The particles 1170 are now in a state of molten resin 1210, as shown in FIGS. 10 and 12A–12D. The lift mechanism is then lowered by means of the lift motor 140 until the upper platform 110 contacts the weight 320, as shown in FIG. 12A, thereby forcibly driving the resin 1210 through the orifice 580, in the form of an extrudate 1220. This is carried out until the melt indexing test is actually to begin. For the test presently described (which is Procedure B in the ASTM D1238 publication mentioned above) the extrudate 1220 is forced through the orifice 580 until the piston 1180 moves by a given amount, such as distance D shown in FIGS. 12B and 12C. The time for the piston 1180 to move distance D (which, it will be understood, depends upon the chosen mass for the weight 320) is then determined, which yields the melt index value for the resin 1210, determined by the following formula:

Flow rate = $(427 \times L \times d)/t$, where L is the length of the piston travel in centimeters, d is the density of the resin at the test temperature in g/cm$^3$, and t equals the time in seconds of piston travel for length L.

At the end of a melt index test, the cartridge 550 is cleared of resin 1210 by forcing the piston 1180 downward to meet the plug 570, as shown in FIG. 12D. This is accomplished by lowering the lift mechanism 50 until the upper platform 110 contacts the weight 320, and continuing to drive the lift mechanism 50 downwards such that the tamping rod 270 forces the piston 1180 to drive the extrudate 1220 out through the orifice 580. Once this is done, the extrudate 1220 is cut off so that, when the cartridge 550 is removed from the bore 470 of the heater block 460, melted resin 1210 or extrudate 1220 does not stick to the plug 570 or the cartridge 550, which can cause injury to the operator or damage to equipment.

A cutting mechanism 1230 is provided for this purpose, and is mounted within the heater housing 440. As discussed in further detail below, the mechanism 1230 may be carried either by the drawer 30 or by the housing 440. The mechanism 1230 includes a cutter blade 1240 carried on a rod 1250, to which it is rigidly attached by means of rivets or pins 1245. The mechanism 1230 includes frame 1260 on which a cutter solenoid 1270 is mounted, as shown in FIG. 14, and the solenoid 1270 includes a ram 1280 having an arm 1290 to which the rod 1250 is attached, such as by means of rivet 1300. The rod 1250 rests at one end in a slidable fashion on a support 1310 of the frame 1260, and rests at its other end on a roller 1320, which is rotatably mounted by means of an axle 1330 upon the frame 1260.

As shown in FIGS. 18 and 21, the cutter (or cutoff) solenoid 1270 is electrically connected to the motor control unit 150. When the solenoid 1270 is energized, it draws the ram 1280 inward, which causes the rod 1250 to travel towards the left from the point of view of FIGS. 14 and 15, thereby causing the cutter blade 1240 to cut the extrudate 1220. The plug 570 includes a beveled or frustoconical surface 1340. When the blade 1240 contacts the surface 1340, as the rod 1250 moves to the left (see FIG. 16), it is forced downward until it reaches the orifice 580, at which point it begins to cut through the extrudate 1220. The blade 1240 should be somewhat flexible for this purpose, or the rod 1250 may be given sufficient vertical play to accommodate this downward motion.

Figure 16:
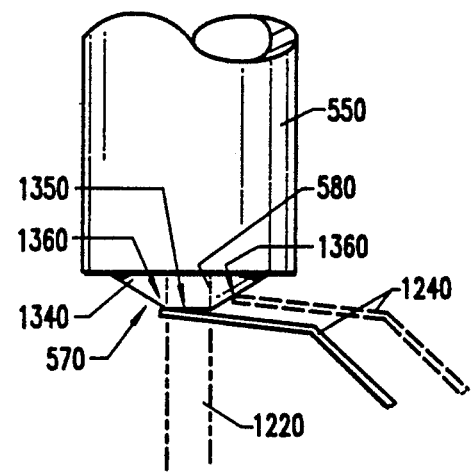
FIG. 16 is an enlarged view of a portion of FIG. 15, showing the operation of the cutting mechanism.
Figure 17A:
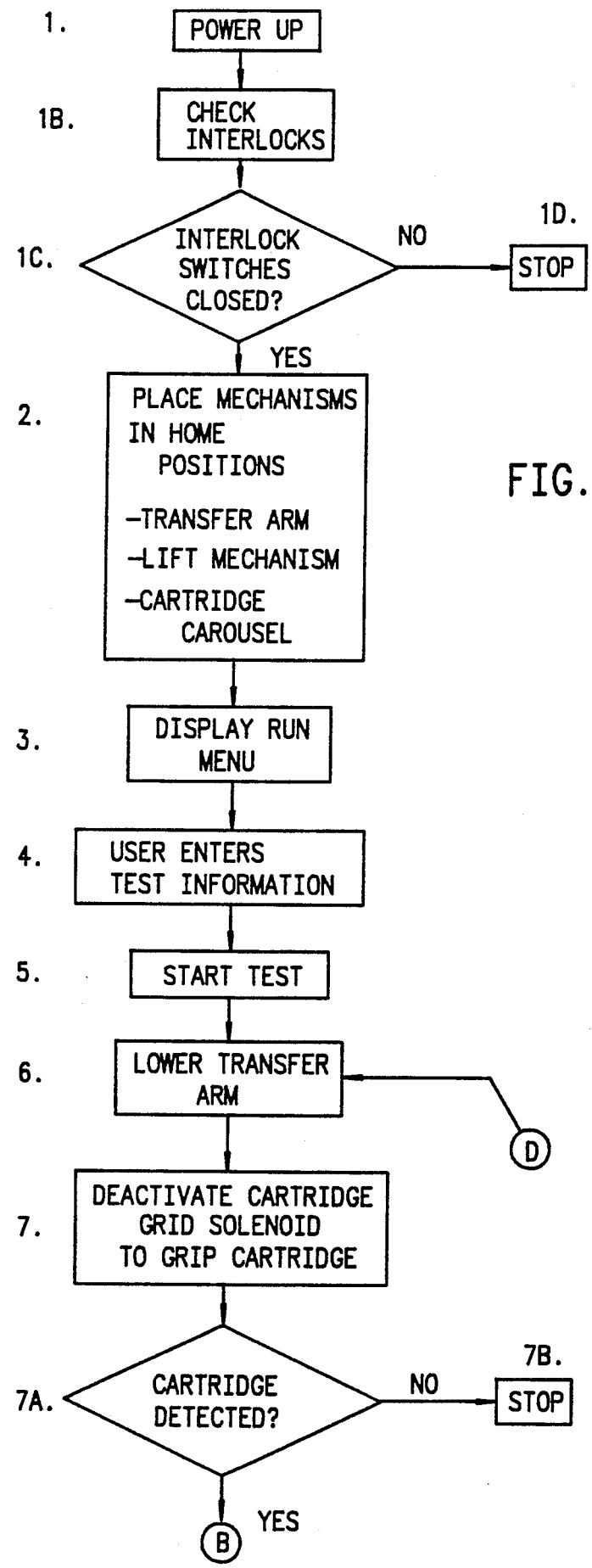
FIGS. 17A-17D show a flow diagram showing the steps in the method of the invention.
Figure 17B:
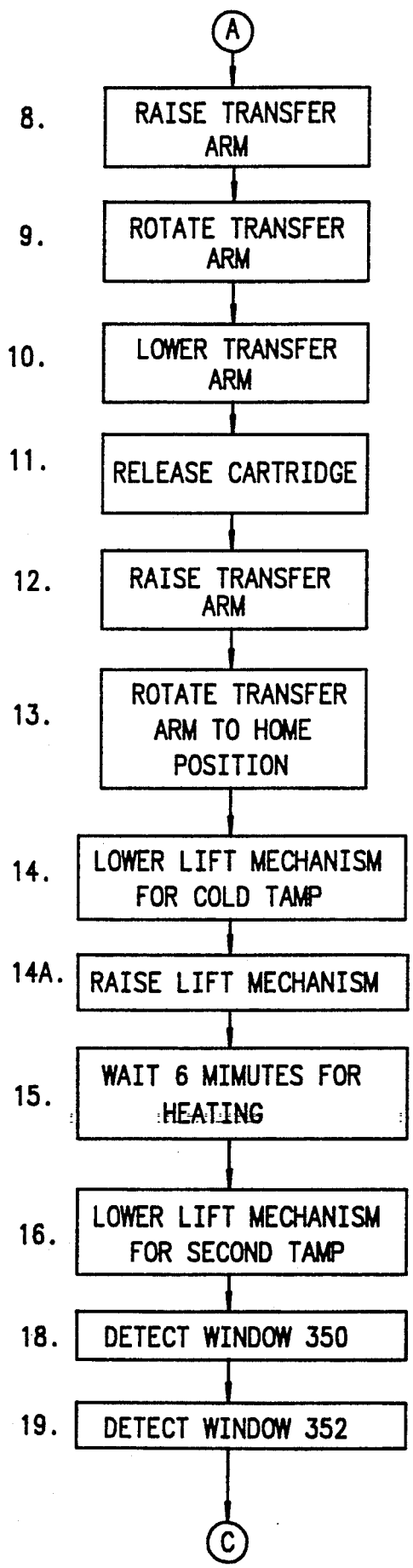
Figure 17C:
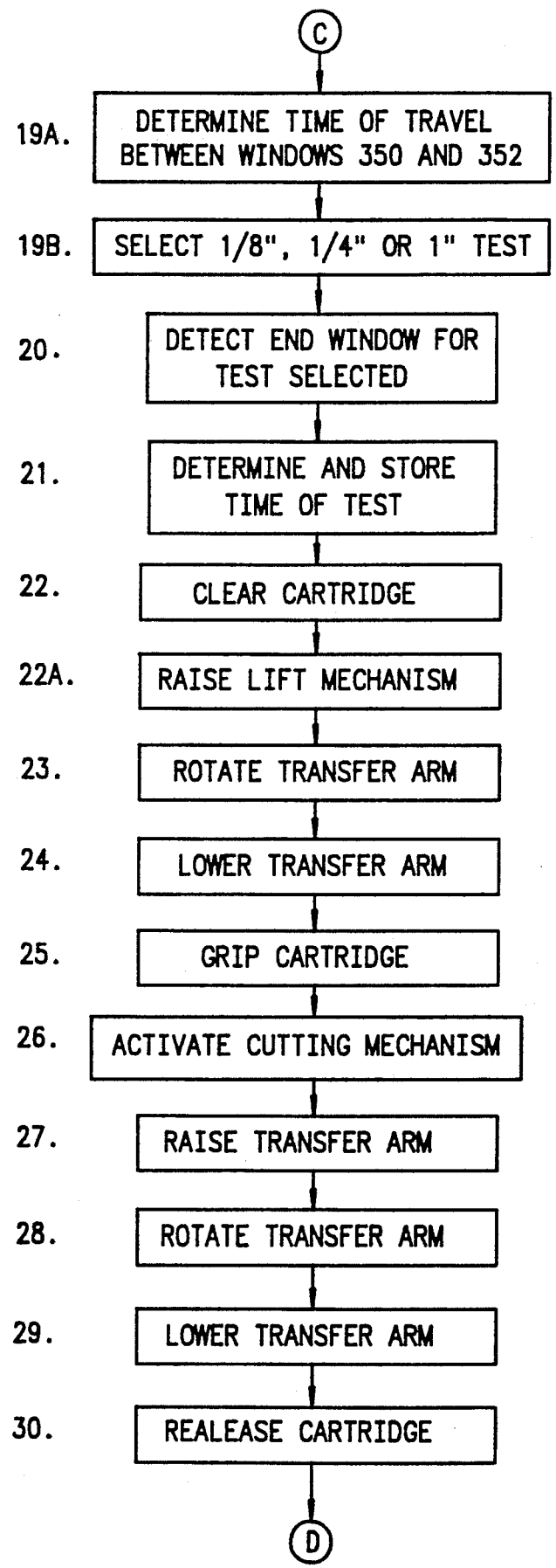
Figure 17D:
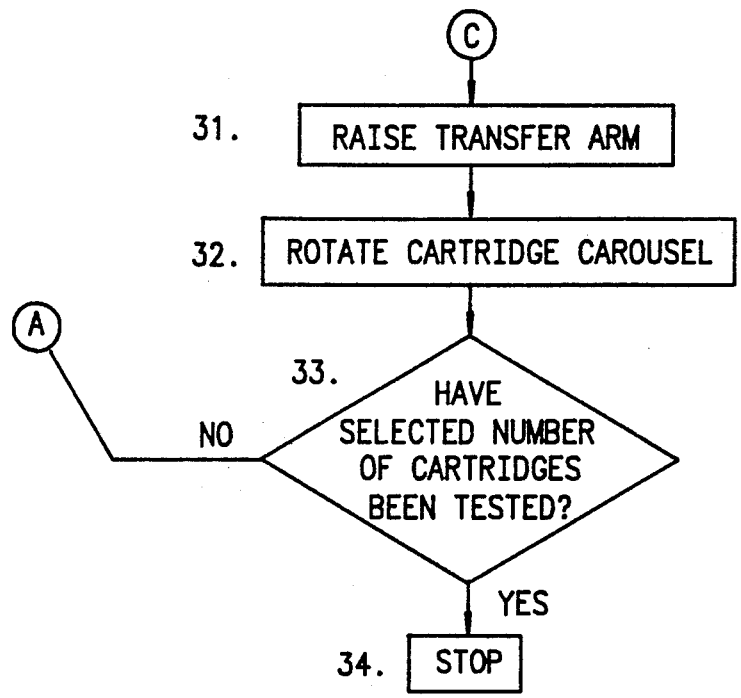
Figure 18A:
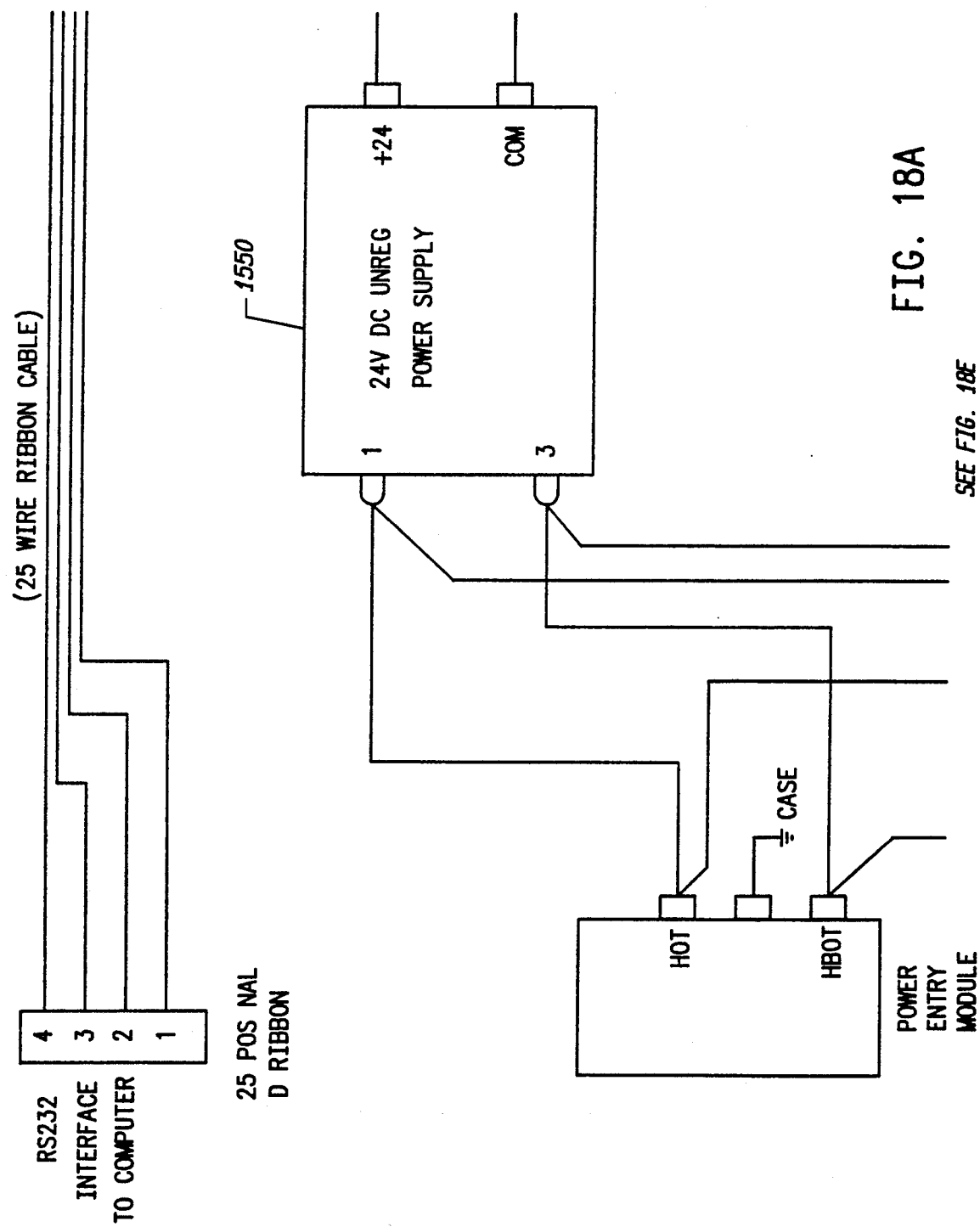
Figure 18B:
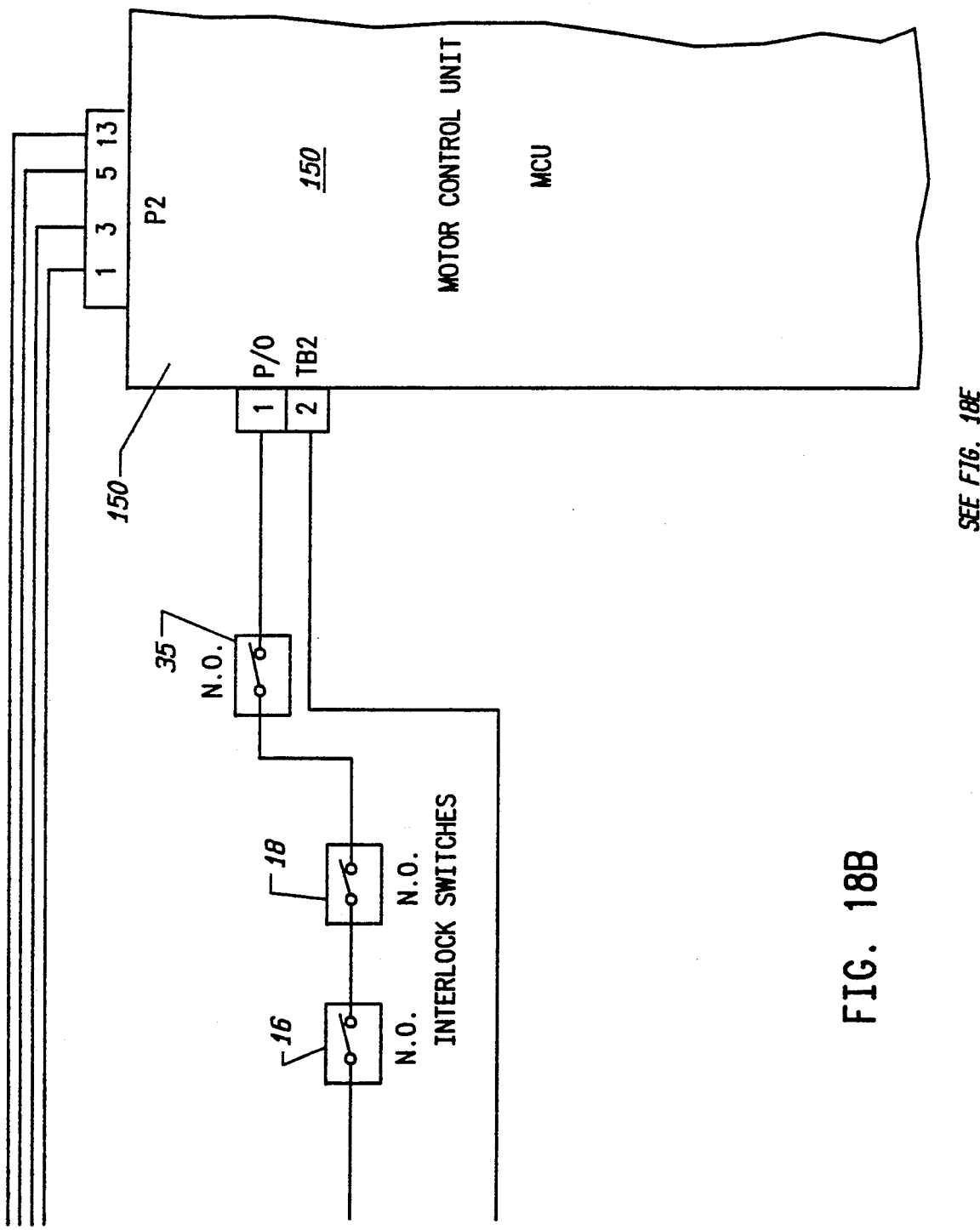
Figure 18D:
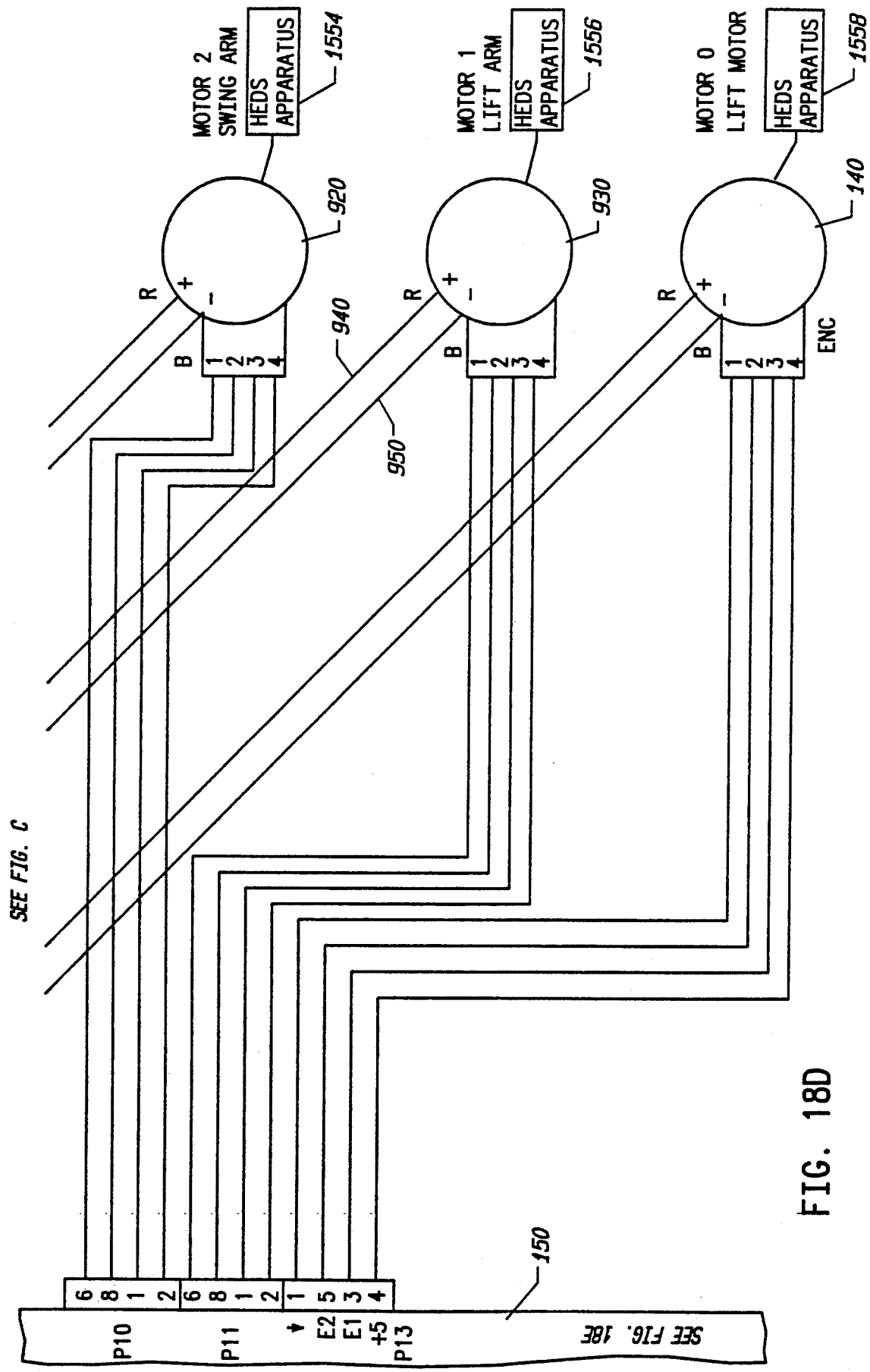
Figure 18E:
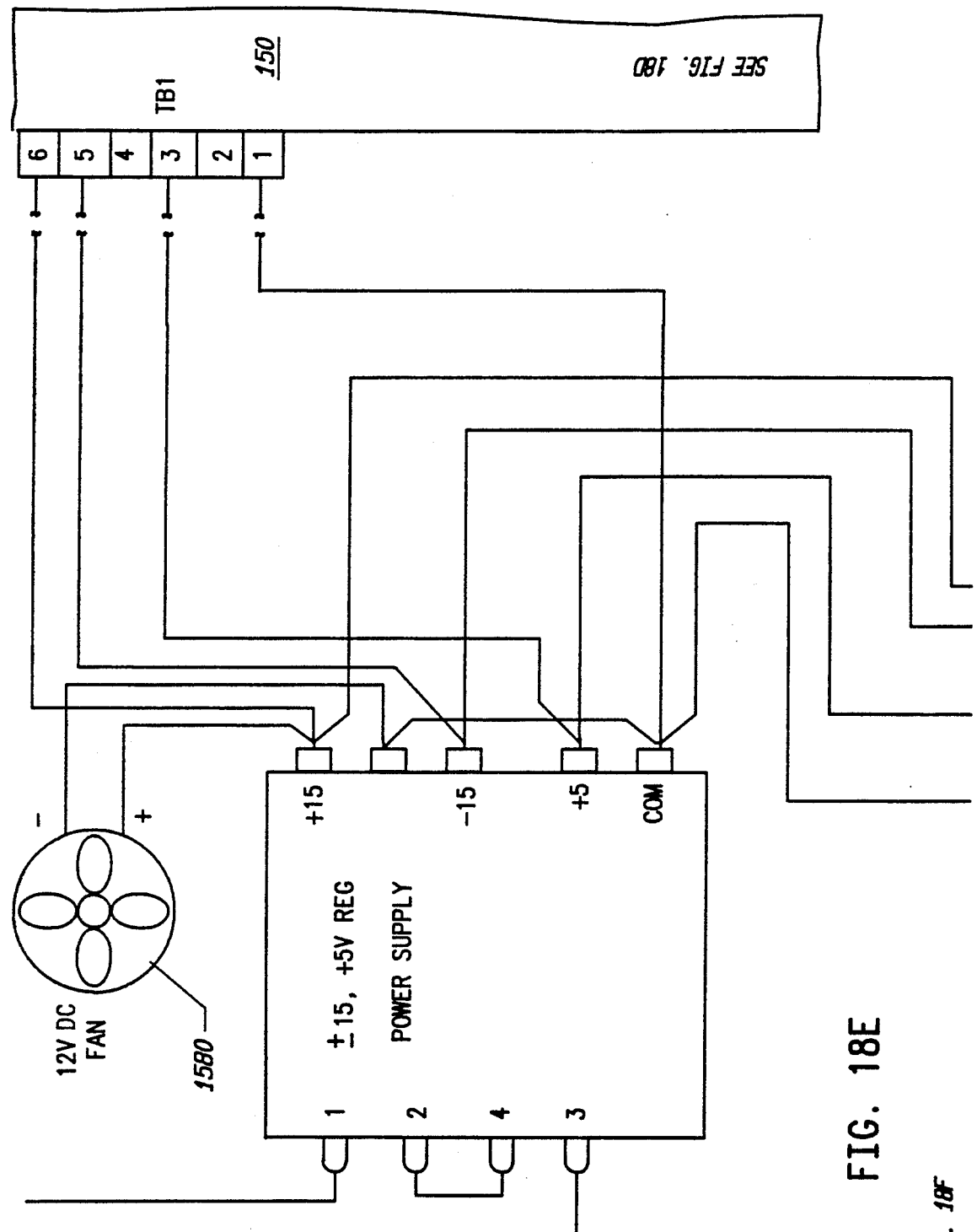
Figure 18F:
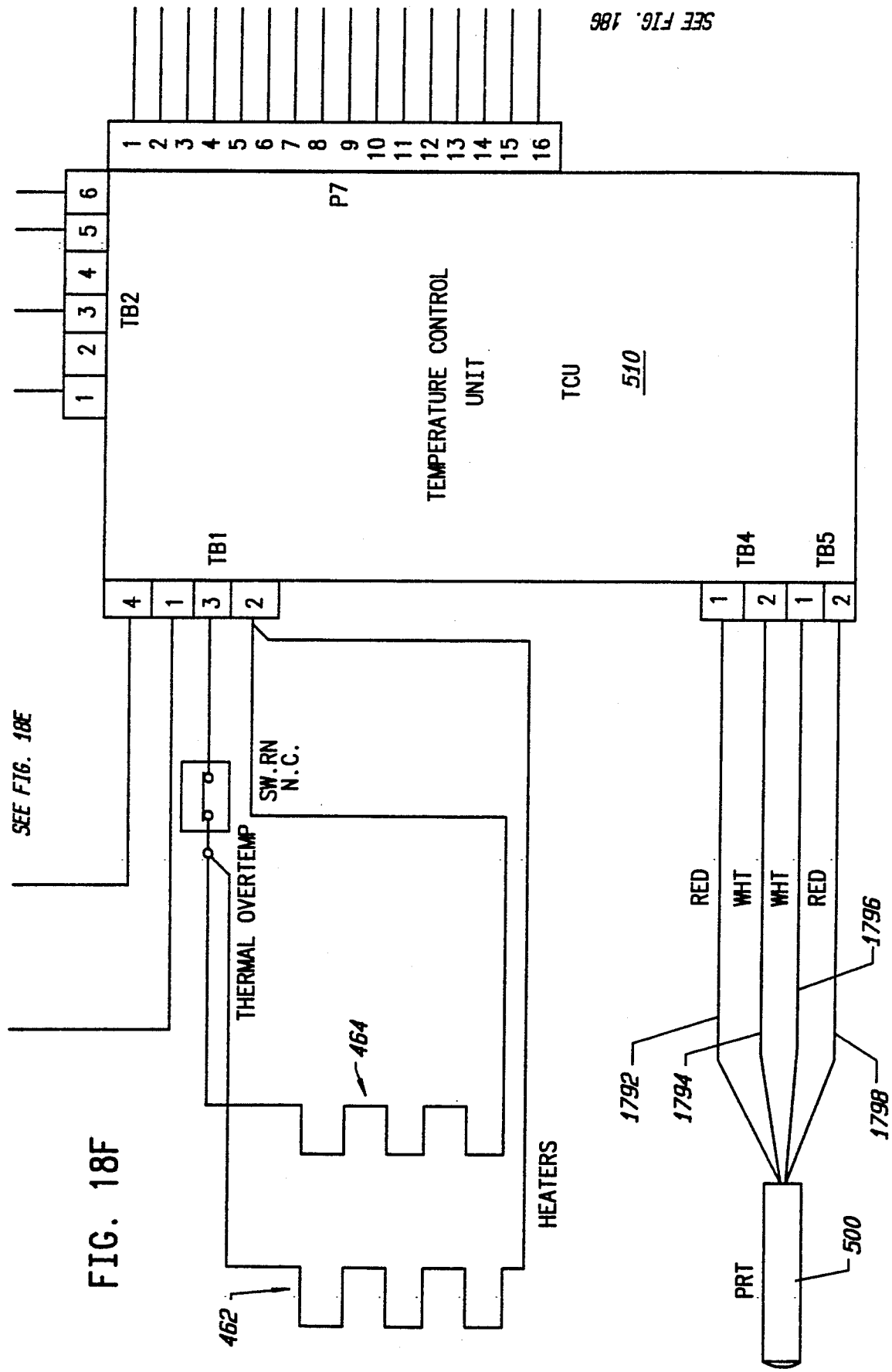
Figure 18G:
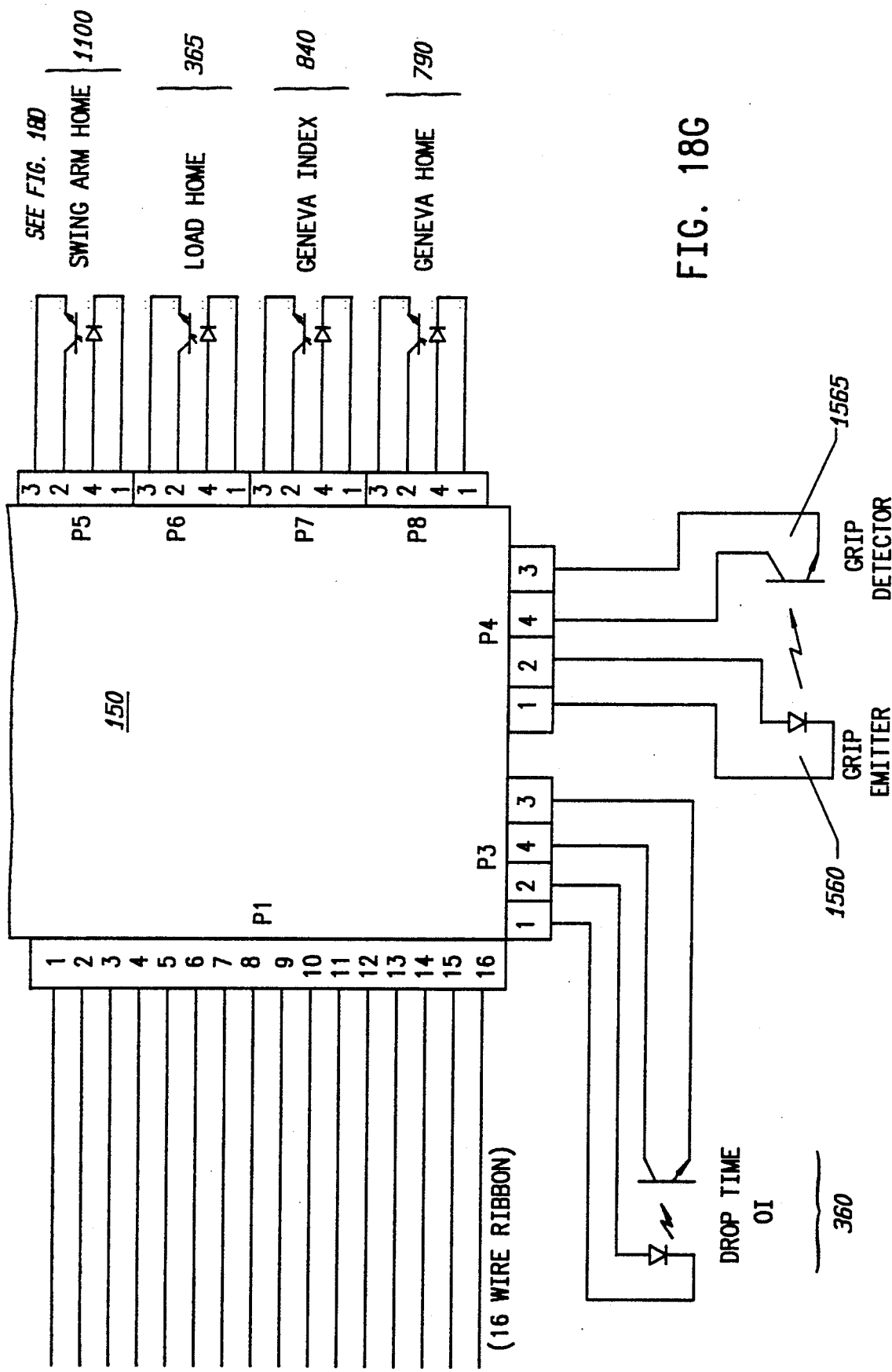

The blade 1240 is preferably angled slightly upwards, as shown in FIG. 16, such that the blade 1240 is not quite parallel--but instead is at a slight angle of one to several degrees--relative to the edge 1350 defining the orifice 580 of the plug 570. The blade 1240 preferably includes a point 1360. It will be appreciated from FIG. 16 that, if the cutter blade 1240 were parallel to the plane defined by the edge 1350, then, rather than cutting the extrudate 1220, the blade 1240 might both cut the extrudate and smear it along the blade and along the surface of the plug 570. This is avoided by providing a sharp, thin shape to the point 1360, and by the upward angling of the blade.

Once the ram 1250 has traveled a sufficient distance such that the blade 1240 has traversed the diameter of the orifice 580, the solenoid 1270 is deenergized. A spring 1370 is provided to drive the arm 1280 outwards, relative to the cutter solenoid 1270, when the solenoid is de-energized, as shown in FIG. 14.

Figure 15:
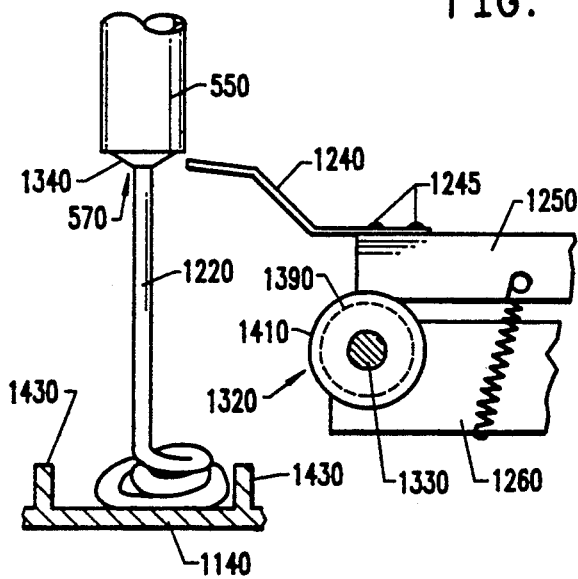
FIG. 15 is a side view of the mechanism shown in FIG. 14.

Another spring 1380 is attached to the rod 1250 and the frame 1260, as shown in FIG. 15, in order to keep the rod 1250 in contact with the roller 1320. As shown in FIGS. 14 and 15, the rod 1250 preferably rests upon a recessed portion 1390 of the roller 1320, with the recessed portion 1390 being defined by flanges 1400 and 1410, in order to inhibit lateral movement of the rod 1250 relative to the frame 1260.

As shown in FIG. 14 and 15, when the extrudate carousel 1140 is mounted on the pin 1150, it is directly below the cartridge 550 carried in the heater block 460, such that the extrudate 1220 falls onto the carousel 1140 as the extrudate flows out of the orifice 580. The carousel 1140 is preferably divided into segments 1420 by means of dividers 1430. The carousel 1140 is provided with ratchet teeth 1440 around its periphery, with one ratchet tooth 1220 corresponding to each segment 1420. A pawl 1450 is provided for rotating the carousel 1140 by pushing the teeth 1440.

Figure 24:
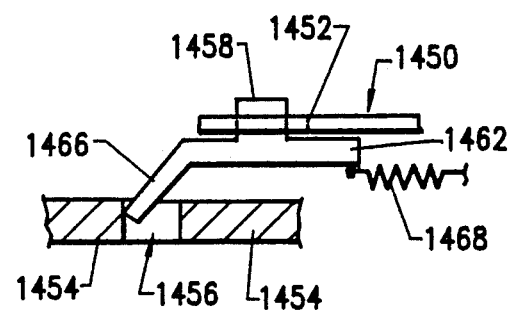
FIGS. 23 and 24 show an alternative embodiment to a portion of the apparatus shown in FIG. 14.
Figure 23:
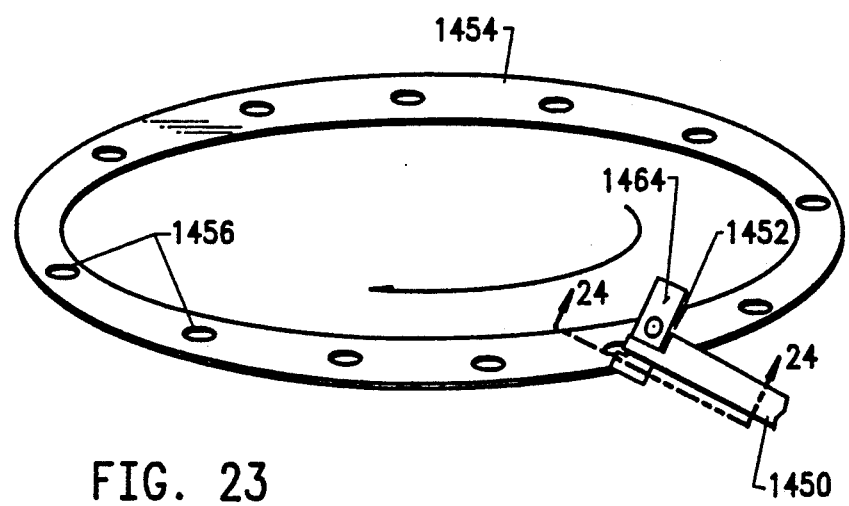

In one alternative embodiment as shown in FIGS. 23 and 24, the pawl 1450 includes an elbow 1452. The extrudate carousel 1140 is mounted on a carousel wheel 1454 having recesses or holes 1456 which perform the same function as the teeth 1440 in FIG. 14. The pawl 1450 is as before driven by a solenoid, and engages a knob 1458 carried on a pivot 1462 which is pivotally mounted at pivot point 1464. The pivot 1462 includes a flexible finger 1462 which is angled downwardly to engage the holes 1456. When the pawl 1450 is moved to the left, the pivot is pulled left by an attached spring 1468, and the finger 1466 is thereby drawn out of a given hole 1456, and rides up on top of the wheel 1454, until it engages the next hole to the counterclockwise direction, at which point it flexes down into the hole. When the pawl moves to the rigth, the stiffness of the finger 1466 in its longitudinal direction allows it to push the hole clockwise, thus advancing the wheel 1454 (and thereby the extrudate carousel 1140) clockwise by one segment 1420.

In the embodiment of FIG. 14, where the frame 1230 is mounted on the drawer 30, the pawl 1450 is attached by means of a rod 1460 to the ram 1370 to the ram 1280 of the solenoid 1270, such that when the solenoid 1270 is energized, the ratchet 1450 contacts a tooth 1440, forcing the extrudate carousel 1140 to rotate through an angle determined by the length of the ratchet tooth 1440. This repositions the carousel 1140 such that a new segment 1420 is positioned beneath the cartridge 550. In the embodiment shown in FIG. 14, the cutter mechanism 1230 is mounted on the drawer 30 by attaching the frame 1260 to a mount 1470 attached at its foot 1480 by means of rivets or bolts 1490 to the drawer 30.

In an alternative embodiment, the 1260 is carried by the heater housing 440. In this configuration, the pawl 1450 is not connected to the ram 1280, and thus the mount 1470 and the rod 1460 are omitted. In this case, the pawl 1450 is driven by its own solenoid 1500, indicated in dotted fashion in FIG. 14. The solenoid 1500 includes a ram 1510 and a return spring 1520. The solenoid 1500 may be driven at the same time as the solenoid 1270, or slightly thereafter, to ensure that the extrudate 1220 has had sufficient time to fall into the segment 1420, which is directly below the cartridge 550, before the extrudate carousel 1140 is rotated. The solenoid 1500 is coupled to and controlled by the motor control unit 150, as shown in FIG. 18.

The pawl 1450 is provided with a slot 1520, which is positioned over a pin 1530 for limiting its travel towards the right, as shown in FIG. 14. Thus, when the solenoid 1270 (or the solenoid 1500) is energized, the extrudate carousel 1140 is rotated one ratchet tooth 1440 in a clockwise direction, and then the pawl 1450 is withdrawn until the pin 1530 meets the end of the slot 1520.

The following is a description of the method for carrying out a series of automatic melt index tests by the apparatus shown in FIGS. 1 and 2, following which is a discussion of the user actions to be taken in connection with an IBM AT personal computer and the specific embodiment of the invention reflected in the software code attached hereto as Appendix A. The steps described below appear in the flow chart of FIG. 17, and are reflected in the timing diagram of FIG. 13. The code appearing in Appendix A is protected under U.S. copyright law, as indicated by the copyright notices on the two parts thereof (the TCU code and the MCU code), and should not be reproduced without these copyright notices.

First, the operator of the unit 10 loads each of the cartridges 550 with particles or pellets 1170 of a given substance, or he may load the carousels with particles of different substances. The cartridges 550 are then placed in the bores 540, so that they are carried by the carousel 530, as shown in FIGS. 2 and 5. The carousel 530 may carry twelve cartridges 550 (as shown in FIG. 2), or fifteen cartridges (as shown in FIG. 4), or other desired numbers of cartridges. In the preferred embodiment, twenty-four cartridges are carried on the carousel 530. Once the carousel 530 is loaded with cartridges, it is placed on the shaft 535. An advantage of being able to place and remove the carousel 530 when fully loaded is that a carousel carrying hot cartridges may easily be removed without burning the operator. Also, where many tests must be conducted, the operator may load one carousel while tests are being performed on cartridges carried in another, so that the unit 10 is not sitting idle while cartridges are being loaded.

As shown in FIG. 17 (box 1), the operator first powers up the microprocessor 40 and also turns on the unit 10 by means of the switch 25 shown in FIG. 1. The motor control unit 150 includes a microprocessor 1980 (see FIG. 21) with a program stored in a memory 2120, which conducts an automatic check to determine whether windows 12 and 14 of the housing or cabinet 20 are closed, as indicated in boxes 1B-1D of FIG. 17. For this purpose, switches 16 and 18 are provided, and are carried by the housing 20. The window 12 and the window 14 may be slid downwardly and upwardly, respectively, in order to open them. The switches 16 and 18 are normally open, but are closed when the windows 12 and 14 are closed, thus completing the circuit. If any of these interlock switches is open, the microprocessor 1980 sends an appropriate message (such as an error signal) to the processor 40.

Another interlock switch 35 is carried on the housing 20, and is also a normally open switch which closes when the drawer 30 is closed. The switches 16, 18 and 35 are connected in series, as shown in FIG. 18, and a power supply 1550 is connected to the motor control unit 150 via the interlock switches 16, 18 and 35. Thus, all three switches 16 18 and 35 must be closed (and hence, the windows 10 and 14 and the drawer 30 must all be closed) before power can be supplied to the motor control unit 150.

Referring to FIG. 17, in box 1B, the program causes these interlocks to be checked, i.e., the computer checks whether there is a closed circuit between the power supply 1550 and the motor control unit 150. Then the lift mechanism 50, the transfer arm 870, and the carousel 530 are automatically brought to their "home" positions, as indicated in box 2. Thus, the transfer arm 870 is raised to its top position, shown in dotted fashion in FIG. 5, and is rotated until the flag 1095 is positioned between the legs 1110 and 1120, thus positioning the transfer arm above a cartridge 550. Likewise, the carousel 530 is rotated by means of the motor 700 until the flag 820 is positioned between the legs 850 and 860 and the flag 780 is positioned between the legs 800 and 810. Finally, the lift mechanism 50 is raised until it is at its highest position, as shown in FIG. 2.

In order to determine the position of the lift mechanism 50, the motor 140 is provided with an optical encoder such as the HEDS-5500 optical encoder available from Hewlett Packard. Such an encoder is shown as encoders 1552, 1554, 1556 and 1558 coupled to motors 700, 920, 930 and, 140 respectively. (Although in the preferred embodiment an angle control motor 920 is used, in an alternative embodiment the motor 920 could be replaced by a solenoid, and the worm 910 could be a toothed ram engaging the gear 900.)

Each encoder 1552, 1554, 1556 and 1558 is coupled to the microprocessor 40, and provides motion detection for the shaft 160, and, in particular, detects when the associated motor stops turning due to the motor mechanism reaching its most extreme position. Thus, detector 1558 determines when the motor 140 has reached its highest position, thereby resisting any further rotation of the shaft 160 and the pulley 155. Once this occurs, the motor 140 is shut off. This provides a backup means—in addition to the flag—for determining the home position. The encoder 1558 is coupled in a conventional fashion to the motor 140.

Once the transfer arm, the lift mechanism, and the carousel are placed in their home positions by the computer as described above, the operator enters information relating to the mass of the weight 320, the density of the substance to be tested, the desired temperature of the test, and the number of cartridges 550 to be tested. Other information may also be entered, such as an operator identification number and a job identification number. This is indicated in box 4 of FIG. 17. The operator then enters a command (see box 5 of FIG. 17) via the keyboard 55 to the computer 40 to commence the automatic melt index testing.

The computer lowers the transfer arm 870 until it is at its lowest point (box 6 of FIG. 17), which is determined by the HEDS-5500 optical mechanism. The apparatus is configured such that, when the transfer arm 870 is at its lowest point, the cartridge grip 1030 and grip foot 1000 will be on either side of a cartridge 550, as shown in FIG. 6. The solenoid 140 is then de-energized to allow the spring 1075 to thrust the cartridge grip 1030 to the right (as viewed in FIG. 6; see FIG. 17, box 7), thus gripping the cartridge 550.

As shown in FIG. 7, the grip foot 1000 carries a photoemitter 1560, which may be the Richmond IRL 81A emitter, and also carries a detector 1565, which may be the Richmond LPT 80A. The emitter 1560 and detector 1565 are coupled to the motor control unit 150, as shown in FIGS. 18 and 21. If no cartridge 550 is present, the detector 1565 will receive the emission from the emitter 1560, and this will be indicated to the microprocessor 40. If this is the case, the computer is programmed to halt the test (see boxes 7A and 7B of FIG. 17). Alternatively, the computer may be programmed to cause the star wheel motor 700 to rotate the carousel to the next cartridge 550, and may repeat this for a predetermined number of times or until a cartridge is detected.

Once a cartridge 550 is gripped by the transfer arm 870, the transfer arm is then again raised to its highest position, as shown in FIG. 5 and in box 8 of FIG. 17, by control of the height control motor 930. The angle control motor 920 then rotates the worm 910 so as to cause the gear 900 and hence the transfer arm 870 to rotate in a clockwise direction, as viewed from above (FIG. 17, box 9). A stop (not separately shown) is preferably provided to limit the travel of the transfer arm 870 in its clockwise direction, such that the cartridge 550 is positioned directly above the bore 470. Another optical sensing unit (not separately shown) may be coupled to the motor 920, to de-energize the motor 920 when the stop is contacted by the lift arm 870.

The lift arm 870 is then lowered again to its lowest position (FIG. 17, box 10), or until the cartridge 550 contacts the flange 660 shown in FIG. 8, thereby automatically shutting off the motor 930. The solenoid 1040 is then deactivated to withdraw the cartridge grip 1030, thereby releasing the cartridge 550. The lift arm 870 is then raised to its highest position, and rotated counterclockwise to its "home" position shown in FIG. 5 and as indicated in FIG. 17, boxes 12 and 13.

Figure 13:
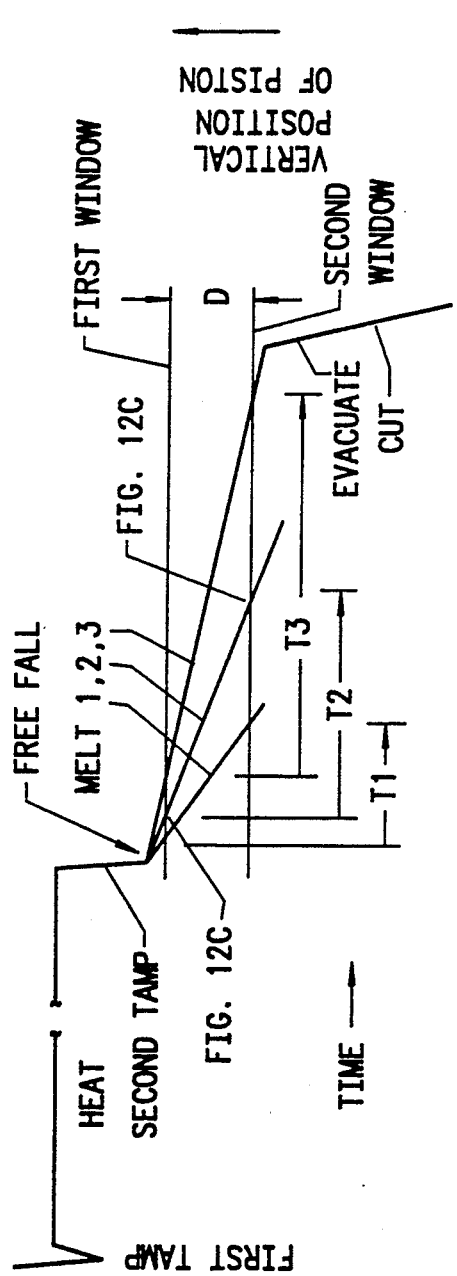
FIG. 13 is a timing diagram for a melt index test.

The lift mechanism 50 is then lowered until the tamping rod contacts the piston 1180, as shown in FIG. 8 and FIG. 17, box 14, and the particles 1170 are compacted in a cold tamp as described above and as shown on the left side of FIG. 13. The lift mechanism 50 is then raised (FIG. 17, box 14A), and a predetermined period of time (preferably 6 minutes) is waited while the the cartridge 550 heats up (FIG. 17, box 15). This is represented in FIG. 13 by the portion marked "HEAT,." The outer diameter of the cartridge 550 should match the inner diameter of the bore 470 closely to maximize the surface area of contact, for efficient heat transfer. The spring-loaded locking mechanism 600 ensures tight contact between the cartridge 550 and the bore 470 to assist in conductive heat transfer.

After the temperature has reached the desired level, the particles 1170 will have melted into a resin 1210. Another tamp is then performed, as described above, by lowering the lift mechanism 50 such that the upper platform 110 forces the weight 320 down, causing the resin 1210 to extrude through the orifice 580, as depicted in FIG. 12A, in the portion of FIG. 13 marked "SECOND TAMP," and in FIG. 17, box 6. At this point, the lift mechanism 50 is in the position shown in FIG. 12A, where the first window 350 is detected by the sensing unit 360.

The lift mechanism 50 is then stopped, as shown in FIG. 12B, to remove any further pressure from the upper platform 110 upon the weight 320. The weight 320 presses down upon the piston 1180 via the tamping rod 270, and hence slowly forces resin 1210 as extrudate 1220 through the orifice 580, as represented in the portion of FIG. 13 marked "FREE FALL" and in FIG. 17, box 17. The computer determines the amount of time taken for the weight 320 to move through the distance between windows 350 and 352 (FIG. 17, boxes 18–19A), as determined by the photosensing unit 360. The unit 360 may be configured to detect either the leading or the trailing edges of the windows 350 and 352. In the preferred embodiment, the distance between windows 350 and 352 is one-tenth inch.

Once the amount of time for the one-tenth inch travel between windows 350 and 352 is determined, the computer then executes a command to conduct a melt indexing test through one of several predetermined distances, provided in the ATDM D1238-85 guideline discussed above (FIG. 17, box 20). If a long period of time is required for the one-tenth inch travel, then a one-eighth inch test will be conducted. For a shorter period of time, a onequarter inch test will be conducted, and, for a very short period of time, a one-inch test will be conducted. Window 354 is utilized for the one-quarter inch test, window 356 is utilized for the one-quarter inch test, and window 358 is utilized for the one-inch test. The test will be described below relative to the one-inch test, but is equally applicable to the one-quarter and one-eighth inch tests.

The computer then recommences its timer, and determined the amount of time the flag 340 takes to travel past the photosensing unit 360 from the window 352 to the window 358 (FIG. 17, boxes 20 and 21). This time is indicated by "T3" in FIG. 13. Since there are two intermediate windows 354 and 356, the computer, in this particular test, is programmed to ignore the first two windows detected by the unit 360, and determines the amount of time to reach the window 358. The one inch distance corresponds to the distance D shown in FIGS. 12B and 12C.

It will be understood that in FIG. 13, the designation FIRST WINDOW refers to window 352, and the designation SECOND WINDOW refers to window 354, 356 or 358, depending on which of these corresponds to the test being conducted. Thus, the computer skips the appropriate number of windows (zero, one, or two), depending upon the test which is selected ($\frac{1}{8}$", $\frac{1}{4}$", or 1"), in determining the total test time.

The distance R shown in FIG. 12C represents the remaining height of resin 1210 when the test is completed, and according to the ASTM D1238-85 standard, this distance should be 0.89 inch. However, other distances are usable, and the apparatus can be configured accordingly.

Once the time taken for the piston 1180 to travel through the distance D (i.e., one inch) is determined, the test is complete, and the lift mechanism 50 is lowered, forcing the weight 320 to drive the tamping rod 370 downwardly, thereby forcing any remaining resin 1210 through the orifice 580 as extrudate 1220, thus cleaning out the cartridge 550 (FIG. 17, box 22). This is indicated by the designation "EVACUATE" in FIG. 13. The lift mechanism 50 is then returned to its home position (FIG. 17, box 22A).

The transfer arm is then rotated, and is lowered to the cartridge 550, and the solenoid 1040 is deenergized to grip the cartridge 550 (FIG. 17, boxes 23-25). The cutter mechanism 1230 is then energized to cut off the remaining extrudate 1220 (indicated in FIG. 13 by the designation "CUT" and in FIG. 17, box 26), with the transfer arm 870 holding the cartridge 550 in place while the extrudate cutoff is carried out. This ensures that, as the point 360 of the blade 1240 contacts the surface 1340 of the plug 570, the cartridge 550 is not forced upwards, which would interfere with a clean extrudate cutoff. The pawl 1450 then rotates the carousel 1140 to the next segment 1420.

The transfer arm 870 is then rotated back to its "home" position, and then lowered so that the cartridge 550 is replaced in the bore 540 of the carousel 530, and the solenoid 1040 is energized, causing the cartridge 550 to be released (FIG. 17, boxes 27-30). The transfer arm 870 is then once again raised (FIG. 17 box 31), and the star wheel motor 700 rotates the carousel 530 to the next cartridge 550 (FIG. 17, box 32). The transfer arm is then once again lowered (FIG. 17, box 31), and the test cycle is repeated for a predetermined number of times, determined by the number entered by the operator as described above (FIG. 17, boxes 33 and 34).

The melt index test results for each of the cartridges 550, i.e. for each of the substances therein, are stored in the computer 40, and may be printed out automatically or upon command by a printer 1570, as shown in FIG. 1.

A fan 1580 (shown in FIG. 18) is preferably provided for keeping the interior of the housing 20 cool. The housing 20 is provided with ventilation means (not separately shown), such as one or more vents, to provide for circulation of air. The heater housing 1440 assists in preventing the fan 1580 from cooling the heater block 460, which would result in inefficiencies.

Once the tests on the substances are completed for a given carousel, the carousel is removed, and another carousel may be put in its place for the next set of automatic tests. The extrudate carousel 1140 is also removed, and a new extrudate carousel is placed over the shaft 1150 in the drawer 30. The extrudate 1220 in the used extrudate carousel can easily be correlated with the printed or displayed results of the melt index testing for the cartridges 550, such as by marking the segments 1420 (either before testing or afterwards) with at least one number to indicate which extrudate was tested first, and thus serves as a useful tool for quality control and error analysis.

Operator Interface

The following are the steps which an operator takes in utilizing the method and apparatus of the invention in connection with the particular software code embodied in Appendix A hereto, as used on an IBM AT personal computer.

Once the operator has loaded the cartridge carousel with the desired number of pre-packed cartridges, placed the carousel 530 onto the shaft 535, placed an appropriate weight 320 onto the weight tray 260, and determined that the extrudate drawer 30 and the windows 12 and 14 are tightly closed, he then enters certain information into the computer 40. As described below, the computer interface with the operator comprises four main screens, namely a melt indexer menu, a set-up screen, a system status screen, and a channel status screen.

Figure 26:
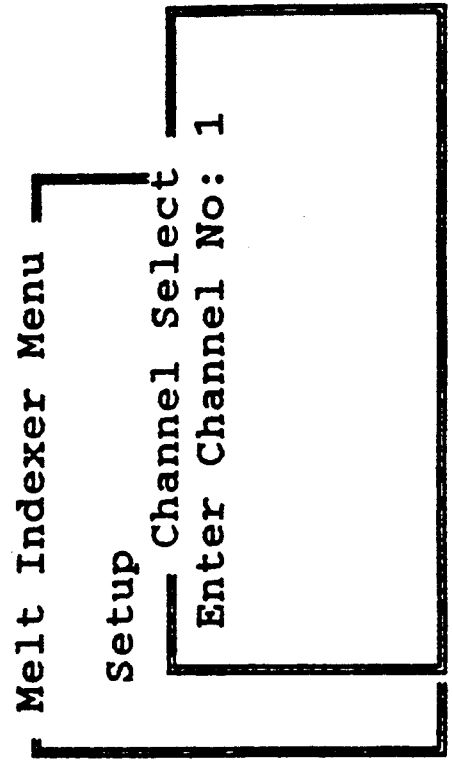
Figure 25:
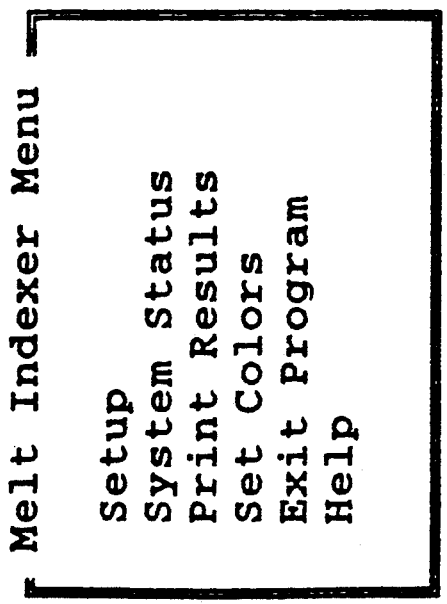

When the melt indexer menu of FIG. 25 appears, the set-up, system status or other menu may be chosen. The operator may choose the channel select menu of FIG. 26, and is prompted to choose a channel number relating to a particular unit 10 which is set up for a test. The channel number is entered by pressing a number between 1 and 8, with the channel number relating to a particular test carousel 530 to be run, as decided by the operator. Once the channel number is pressed, a screen such as that shown in FIG. 26 will be displayed. The top two lines are variable for user entry of institutional information such as company name, laboratory name, address and other information. This information can be edited by moving the cursor up to the appropriate spot as it appears on the menu.

The operator chooses the set-up menu by pressing an "S" on the keyboard 55, or by moving the cursor line up and down with cursor keys or the space bar, and pressing the enter key when the "set-up" is highlighted. At this point, the set-up menu will come up, appearing as in FIG. 27. The set-up help screen of FIG. 28 may be selected by pressing F1, as indicated in FIG. 27.

Typically, the operator will then enter his identification information, such as his name or number, as shown in FIG. 29. Once he presses the enter key, the cursor will move to the project number, and up to 10 characters may be entered. The job number also accommodates up to 10 characters. The file name should be entered for storage of the results of the test run to disk, for later retrieval from the computer for updating or printing out.

The run temperature for the melt indexer test should also be selected, and in the present embodiment may be anywhere from 100° to 300° C. The mass of the weight 320 is also selected (see FIG. 30), and in this case is expressed in grams. Next, the user selects the number of cartridges in a run, which in the preferred embodiment may be between 1 and 24. Finally, the user of the apparatus enters the density of the test substance in each of the cartridges beginning with the first cartridge, as shown in the set-up menu of FIG. 31. To exit this menu, the operator presses the escape key to return to the main menu.

To start the run, check system status, or to abort or pause a run, the operator presses "Y" to get to the system status menu shown in FIG. 32, or presses the enter key when the cursor is over the system status line in the melt indexer menu of FIG. 25. The system status screen of FIG. 32 allows the operator to view up to 8 channels connected to the computer, thus allowing up to 8 simultaneous units such as unit 10 to be operated in parallel from a single computer. This screen displays the total number of tests in the run, the number of tests which have been completed, the current temperature of the particular channel, and the status of that channel. The status of a particular channel is indicated to be "off line" if nothing is connected or if the power for that channel is turned off; "idle" if the channel is powered up but a test is not currently being run; "working" if a current test run is in progress, "paused" if the operator has paused a given channel for any reason; "complete" if a run is completed and is ready for the next run to be setup; and "error" if some error has arisen in the processing of the test,.

If the operator presses the F1 key while the screen of FIG. 32 is up, the screen of FIG. 33 comes up, and the operator may access the system status help screen of FIG. 34 by placing the cursor adjacent the command desired (in this case, "Help"), and pressing the enter key.

To view the full status of a given channel, i.e. a given unit 10, the computer,s cursor is used to highlight that particular channel, and the operator presses the enter key, at which time the channel status screen for that channel will appear, as shown in FIG. 35. This display shows the name or number of the operator who set up the channel, the project and job numbers, the predetermined temperature, the current temperature, and the number of cartridges in the run. This is followed then by a chart showing the numbers of the individual cartridges, the sample identification information, the distance for the melt index test for each cartridge sample, the beginning melt temperature for each test, the total time for the test (i.e., T1, T2 or T3 as shown in FIG. 13), and the resulting melt index values as calculated by the computer.

If the status line in the screen of FIG. 35 is "idle," the operator presses the command key F1 on the keyboard 55, and is then prompted to run the test. The channel status screen is updated approximately every minute by the computer 40. Once the run is complete, the user may press the escape key to return to the main menu in order to print the results. Printing the results is accomplished by placing the cursor so as to highlight the "Print Results" line in the melt indexer menu of FIG. 22, at which time the F1 command key is activated, and is pressed to print out the results.

Figure 37:
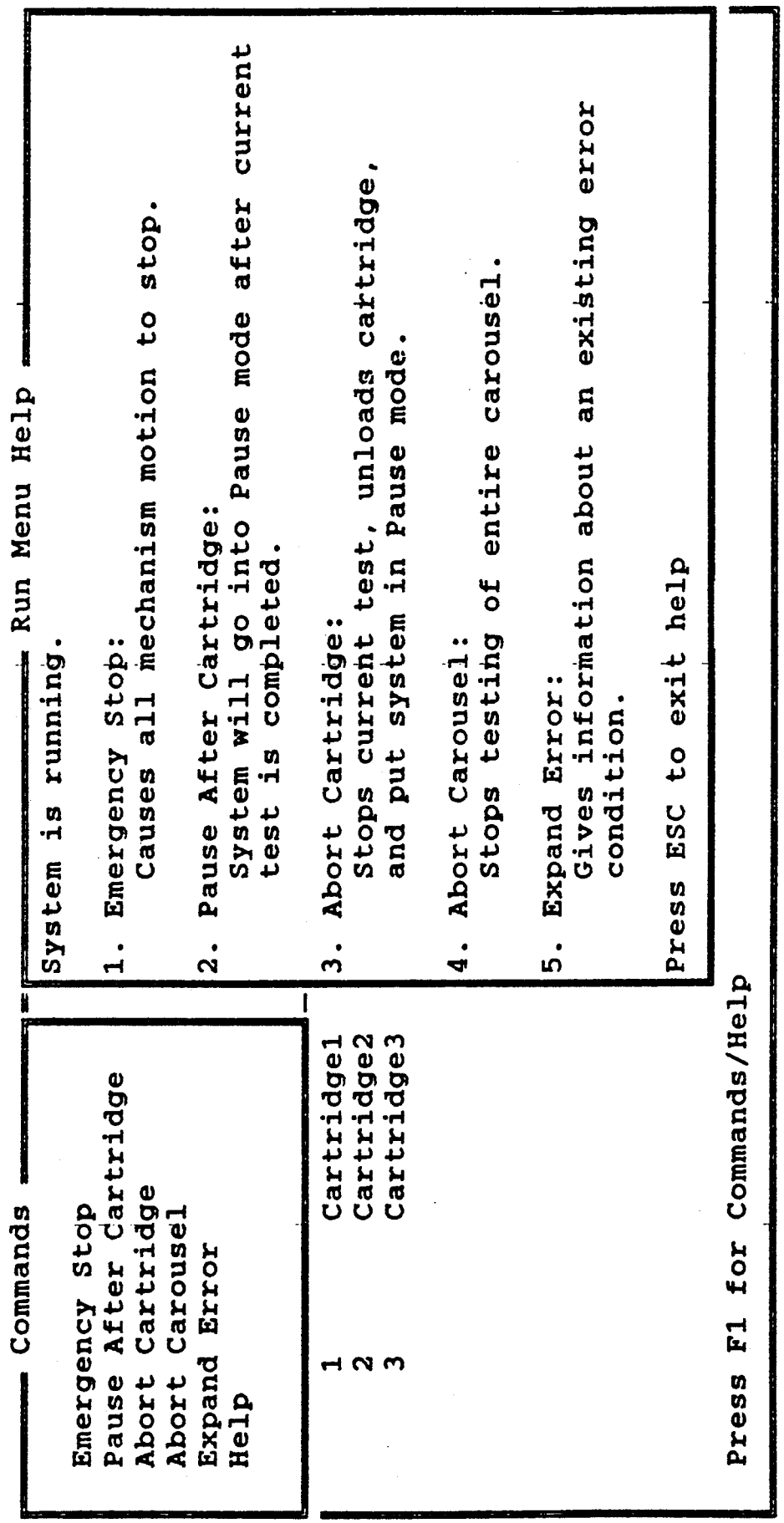

A press of F1 while the screen of FIG. 35 is up, at which point the user may also access the screen of FIG. 37. As seen from the screens of FIGS. 25-37, the use of the system of this particular embodiment is largely self-explanatory.

Schematic Diagrams

The following is a general description of the temperature control unit (TCU) 510, after which the schematic diagrams of the TCU—represented in FIGS. 19 and 20—will be described in detail. Following that is a discussion in detail of the circuitry for the motor control unit (MCU) 150, which is shown in FIG. 21.

The melt indexer temperature control unit (TCU) is a microprocessor-based adaptive proportional integral derivative (PID) loop used for controlling the melt temperature in a melt indexer. The microprocessor used in the TCU is an 8-bit generic 8032 microcontroller based on a 12 MHz clock. The adaptive PID loop algorithm closes the TCU using a DIN, 100 Ohm platinum resistance sensor which drives a 120 V A.C., 5A trial, using a linearized phase proportioned signal, which drives a resistance wound heater.

The TCU uses a 16-bit adaptive PID algorithm for controlling the heater output. The PID gains are a direct function of the process and set point variables. The algorithm uses a finite sampling technique for reading the 16-bit A/D converter, doing computations and updating the heater output signal.

Through a switching network and using multiplexers, the TCU utilizes a ratiometric technique for deriving the current resistance value from a four-wire platinum resistance thermometer (PRT). First, the microprocessor will switch in a reference current through a known resistor. Then, a voltage (VR2) reading is taken at the node connecting the current source to the resistor. Next, a reading of the voltage (VR1) on the opposite end of the resistor is taken. After VR1 and VR2 are measured and stored, the microprocessor will switch the same current source throughout the PRT. The voltage at the node between the element and source (VP2) is read and stored. Next, the voltage on the opposite end of the element (VP1) is read and stored. The unknown resistance (PRT resistance) is computed using the following formula:

$$R_T = R_F * (VP2 - VP1)/VR2 - VR1)$$

where:
$R_T$ = PRT resistance
$R_F$ = Reference resistance

After the PRT resistance is determined, the TCO compares the PRT value to a setpoint value stored in memory. A 16-bit error signal is generated from this comparison and a proportional plus integral plus derivative (PID) compensation is computed on the error signal. The resultant output is truncated to 8 bits precision and is sent to a phase proportioned trial drive.

The PID gains are a function of the controlled and setpoint variables (thereby making them adaptive). The adaptation techniques switches in two different PID gains dependent on the current value of the controlled variable. The gain switching techniques uses a parameter called the resistance crossing point (RC), and the following inequality:

If $R_T < R_C$ then $K_P = K_{P1}$; $T_{iC} = T_{iC1}$; and $T_D = T_{D1}$.
If $R_T > R_C$ then $K_P = K_{P2}$; $T_{iC} = T_{iC2}$; and $T_D = T_{D2}$.

where:
$K_P$ = proportional gain
$T_{iC}$ = integrator time constant
$T_D$ = derivative time constant.

The resistance crossing point is determined by the following formula:

$$R_C = R_{SP} - R_{OFF}$$

where:
$R_{SP}$ = setpoint resistance value
$R_{OFF}$ = empirically determined offset, used for overshoot minimization.

Other features incorporated into the TCU includes a bused RS-232 interface, and an accurate optically interrupted drop timer measurement. There is also a local 8-bit interface designed for controlling external digital devices, or for communications to another controller.

The temperature control unit 510 shown in FIG. 18 is carried on a circuit board within the cabinet 20. The temperature control unit (TCU) 510 shown in FIG. 18 is represented schematically by FIGS. 19 and 20 together. As shown in FIG. 19, the TCU 510 includes a microprocessor 1590 coupled to a read-only memory (ROM) 1600 for storing program commands, and a data latch 1610 for the ROM 1600. A random-access memory (RAM) 1620 is also used, as is a memory 1630, in which is stored look up tables for linearization of tamping data; i.e., the memory 1630 includes the calibration data for the platinum resistance thermometer 500.

Figure 19A:
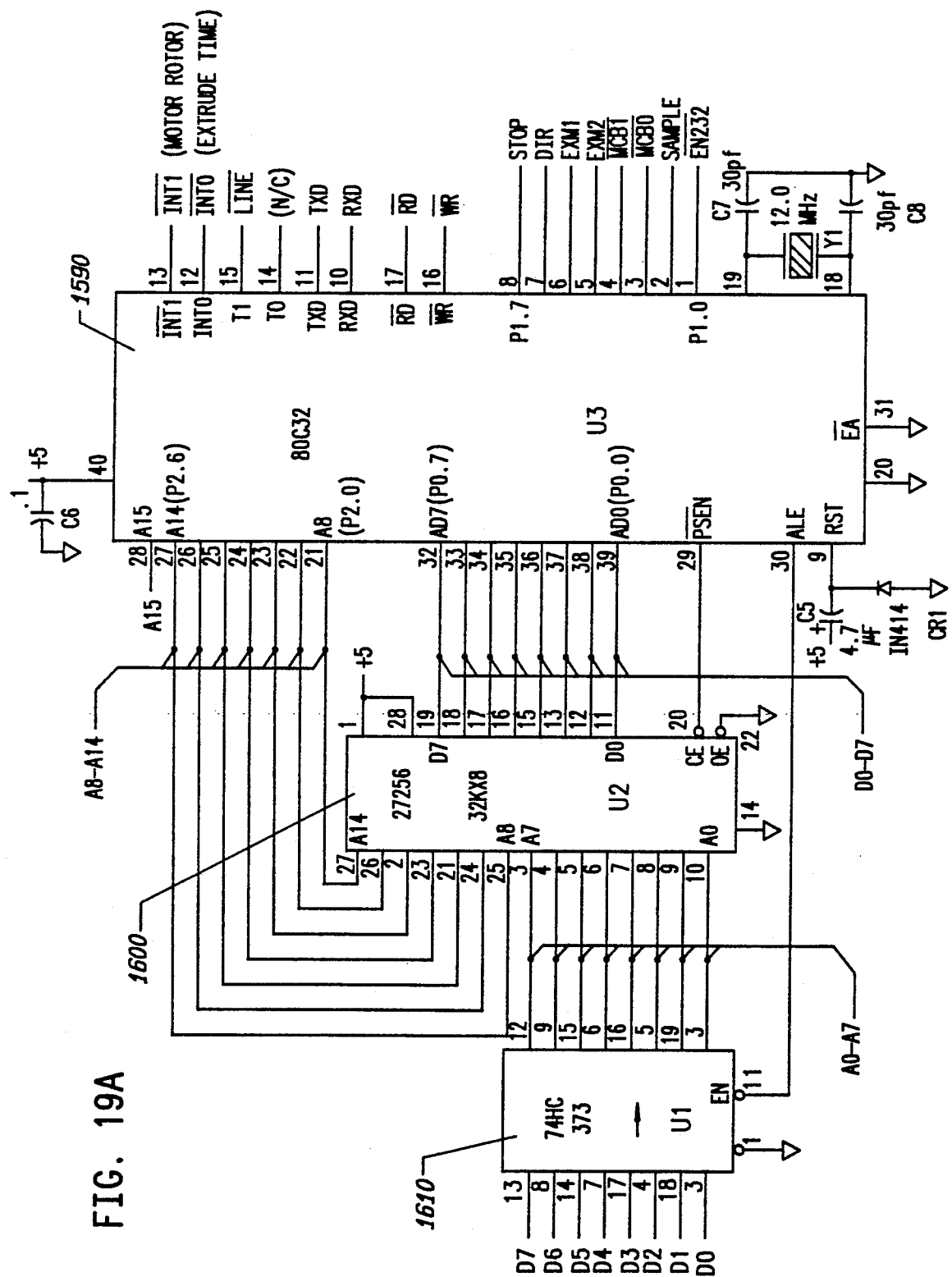
Figure 19B:
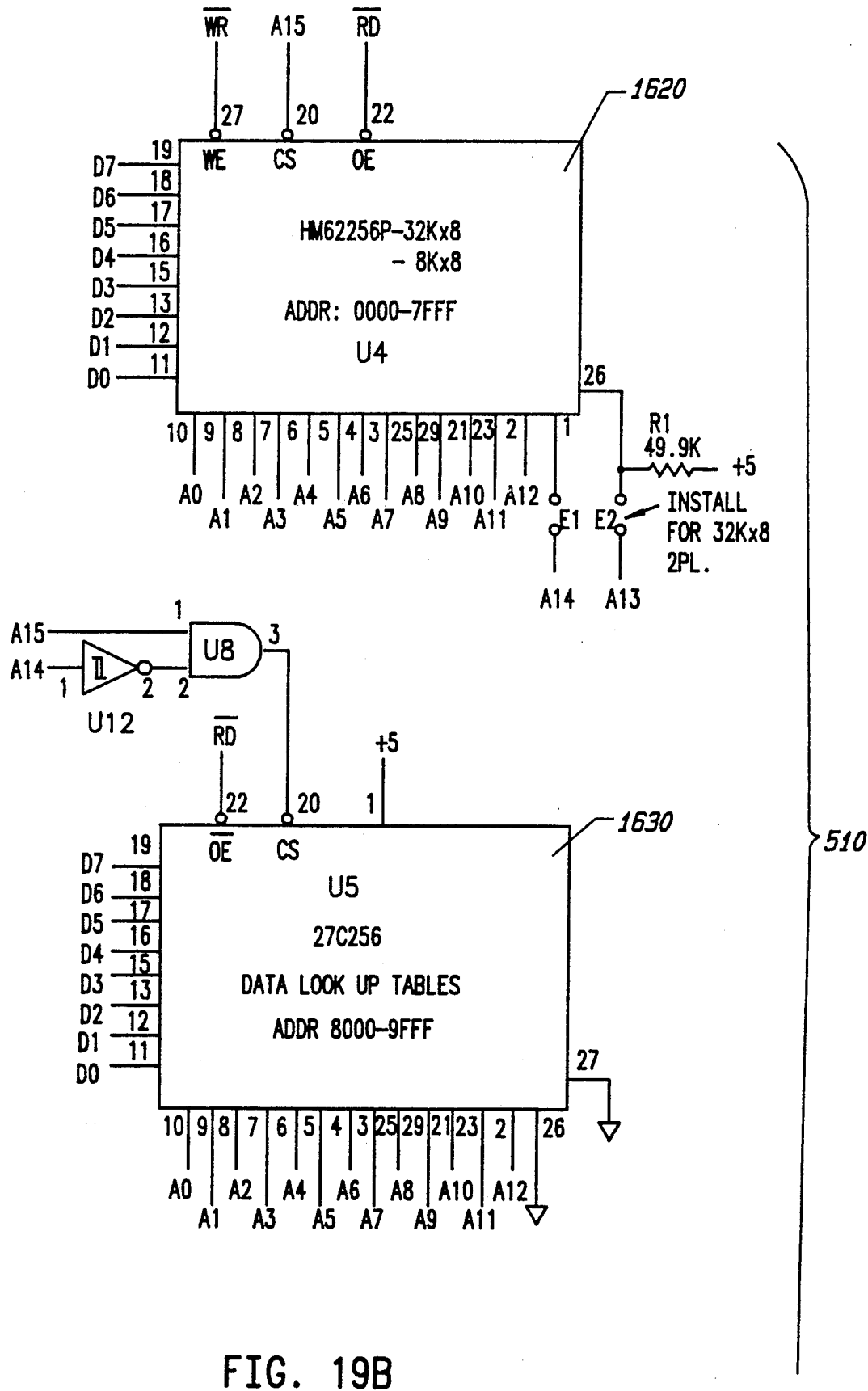
Figure 19C:
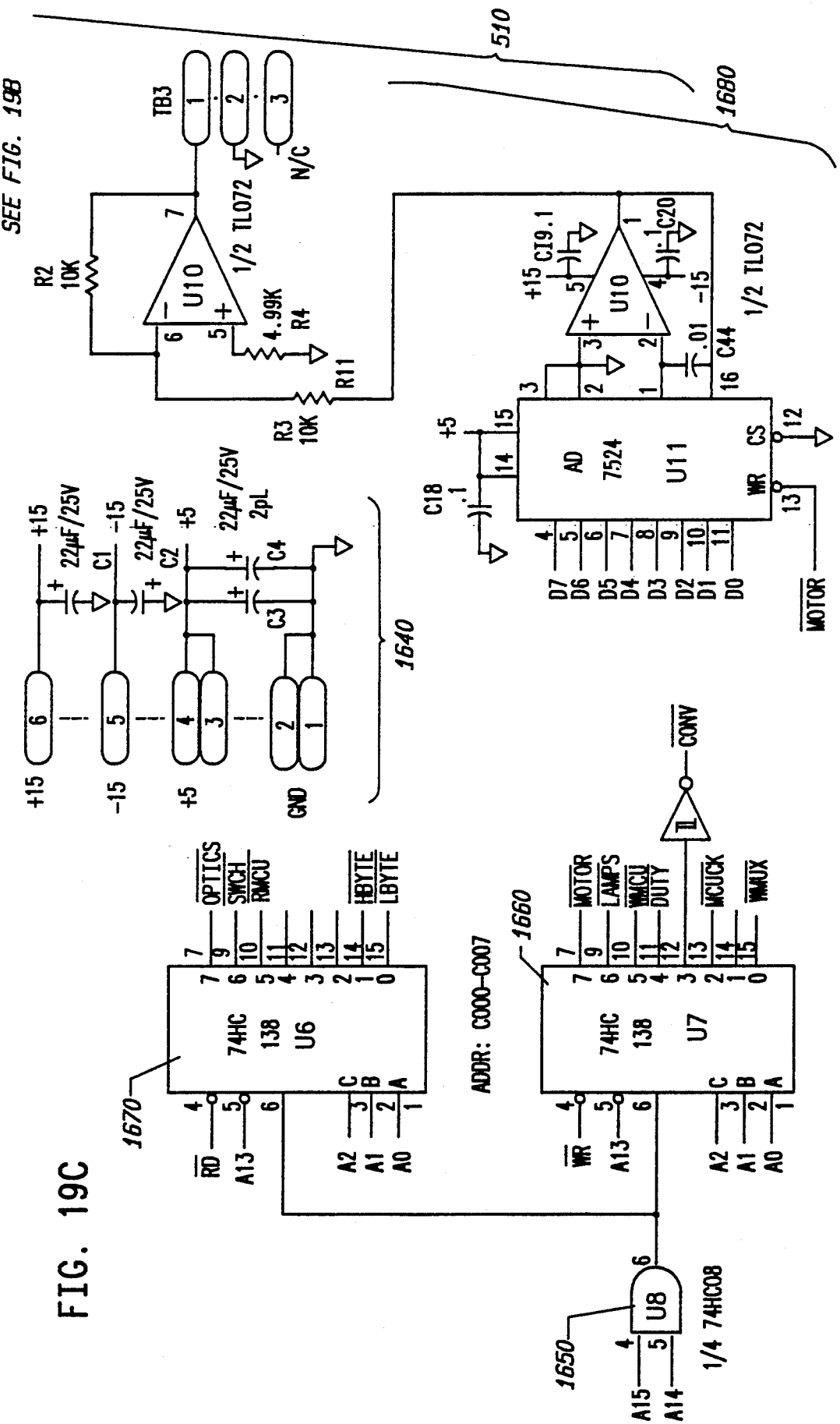

The power supply input 1640 is shown at the lower left of FIG. 19. The TCU 510 also includes address decoding support chips 1650, 1660 and 1670, coupled as indicated in FIG. 19, and analog output debugging circuitry 1680, which is utilized for printing out information by using the microcomputer 40.

FIG. 20 shows the remainder of the TCU 510. This includes an interprocessor communication circuit 1690, which is used for communication between the motor control unit (MCU) 150 and the TCU 510. In the present embodiment, in order for an operator utilizing the microprocessor 40 to communicate with the TCU 510, information must first be sent through the MCU 150.

A comparator 1700, including a data latch (not separately shown) receives a signal from the microprocessor 1590 (shown in FIG. 19) relating to the desired temperature for a given test. The comparator 1700 then determines the amount of power necessary to reach the desired temperature, and effectively synchronizes the powering of the heater elements 462 and 464 with line frequency. For this purpose, a phase-locked loop chip 1710 is used, as are counters 1720 and 1730. Empirical data relating to the platinum resistance thermometer 500 are stored in memory 1600 (shown in FIG. 19).

The comparator 1700 compares the current temperature with the desired temperature. The PLL chip 1710 divides the line signal into 256 parts per cycle, and feeds the output into the counter 1720. The comparator determines the amount of power being input and the amount of power necessary to reach the desired temperature. When the amount of power input is low, the chip 1740 is driven high, thus causing an emission from a light-emitting diode 1750. This activates an optical switch 1760, with 1750 and 1760 together comprising an optical coupler. The signal from the switch 1760 is sent to a power switch 1770, from which the signal is sent to the heating units 462 and 464, as indicated in FIG. 20. It would be noted that there is an isolation boundary 1780 between the power circuitry and the remainder of the circuitry.

Figure 20A:
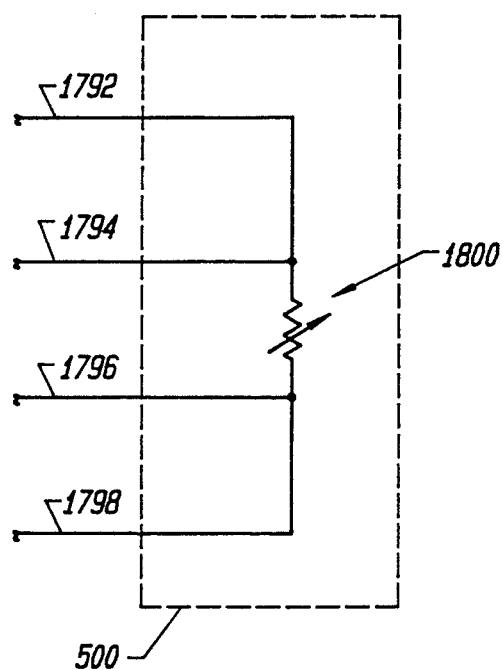
Figure 20B:
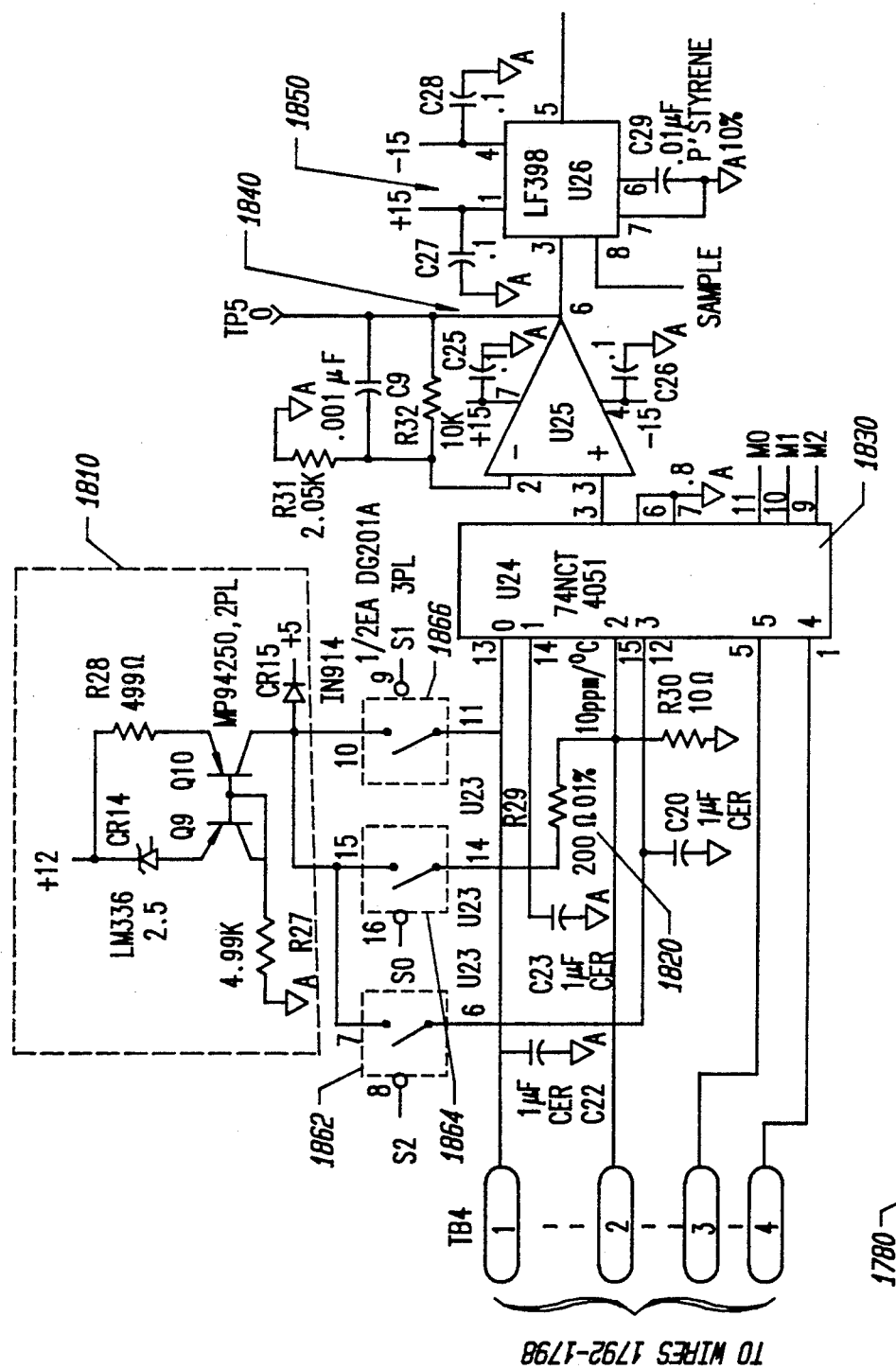
Figure 20D:
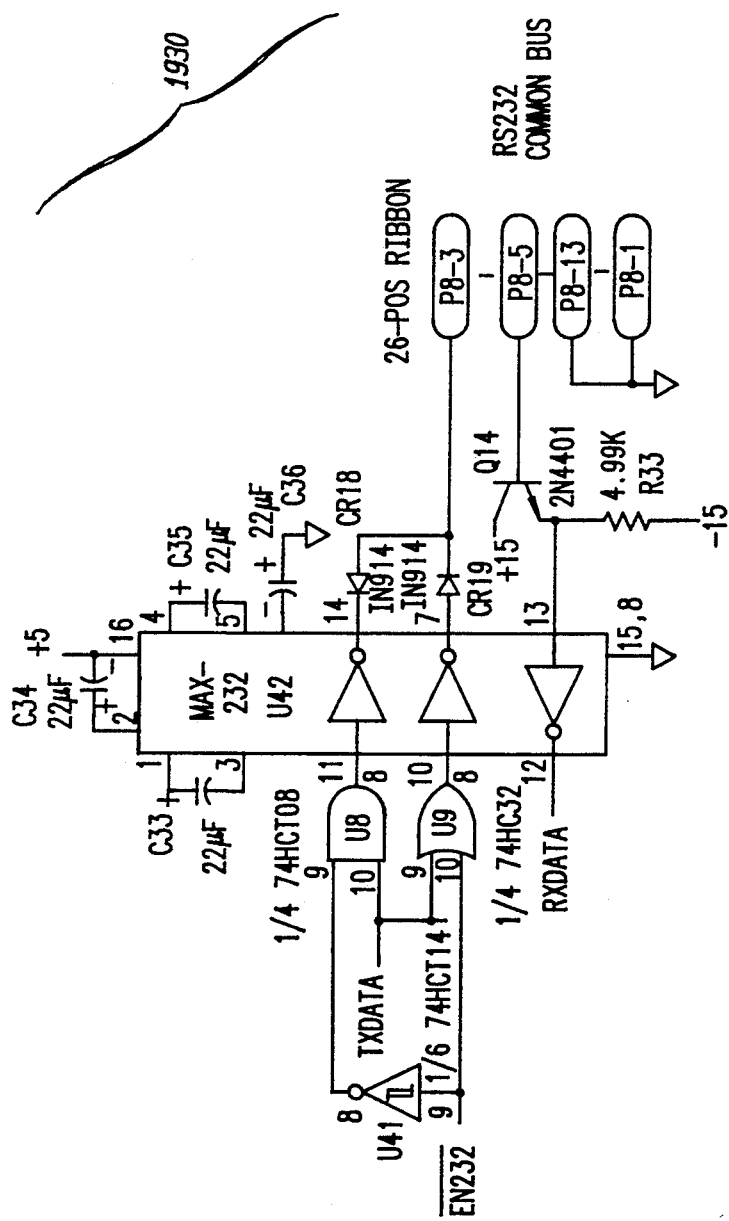
Figure 20E:
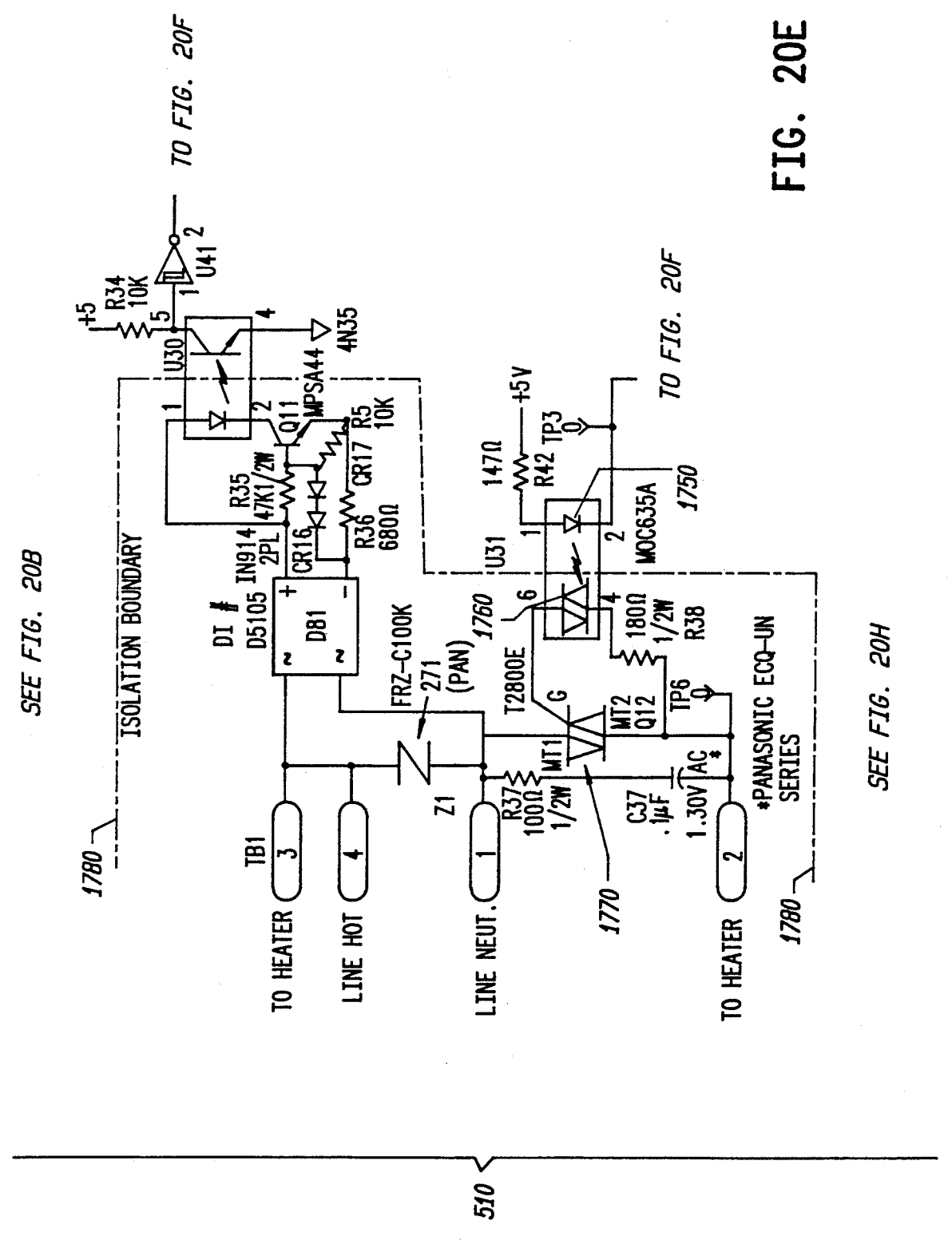
Figure 20F:
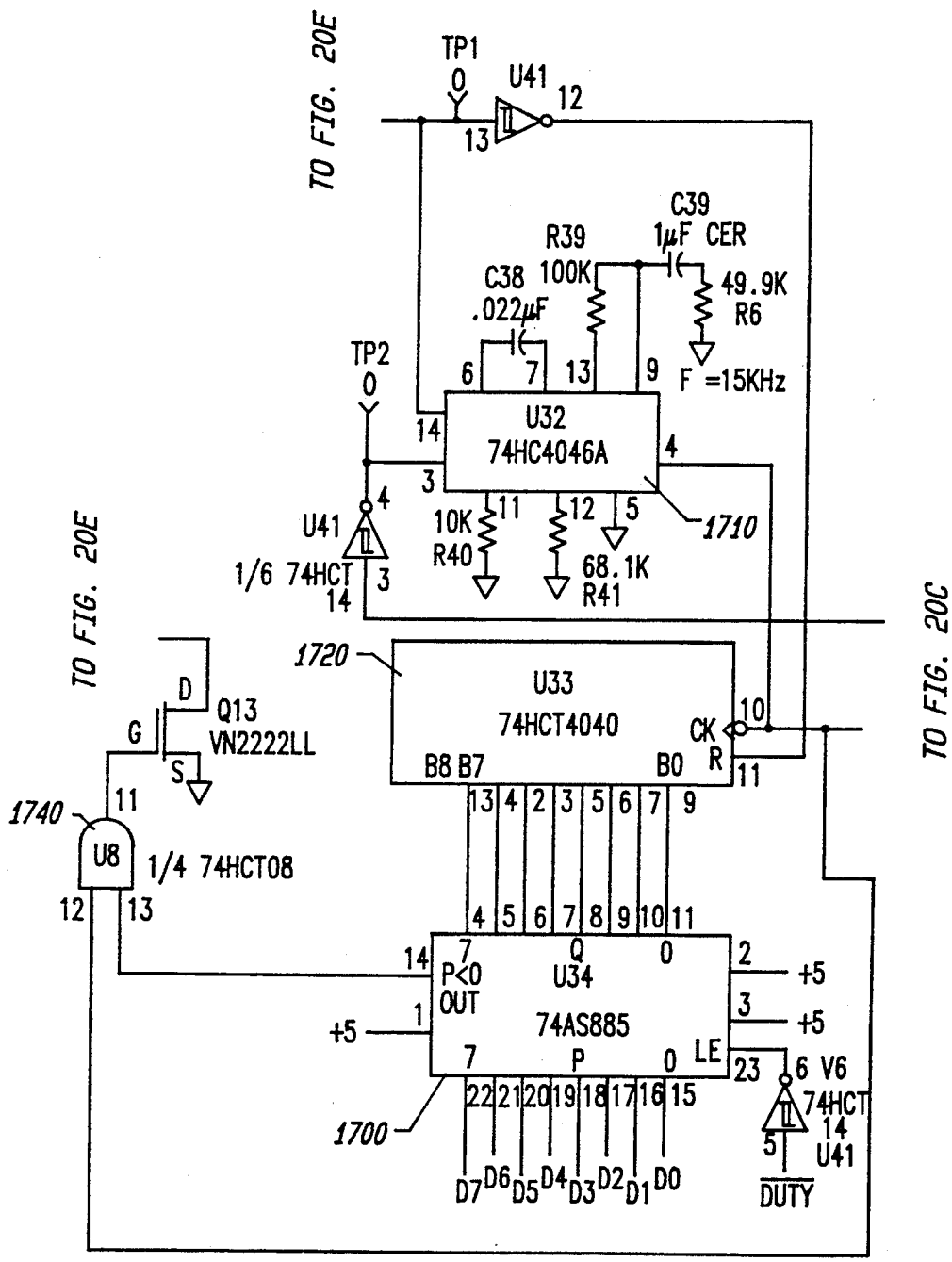
Figure 20G:
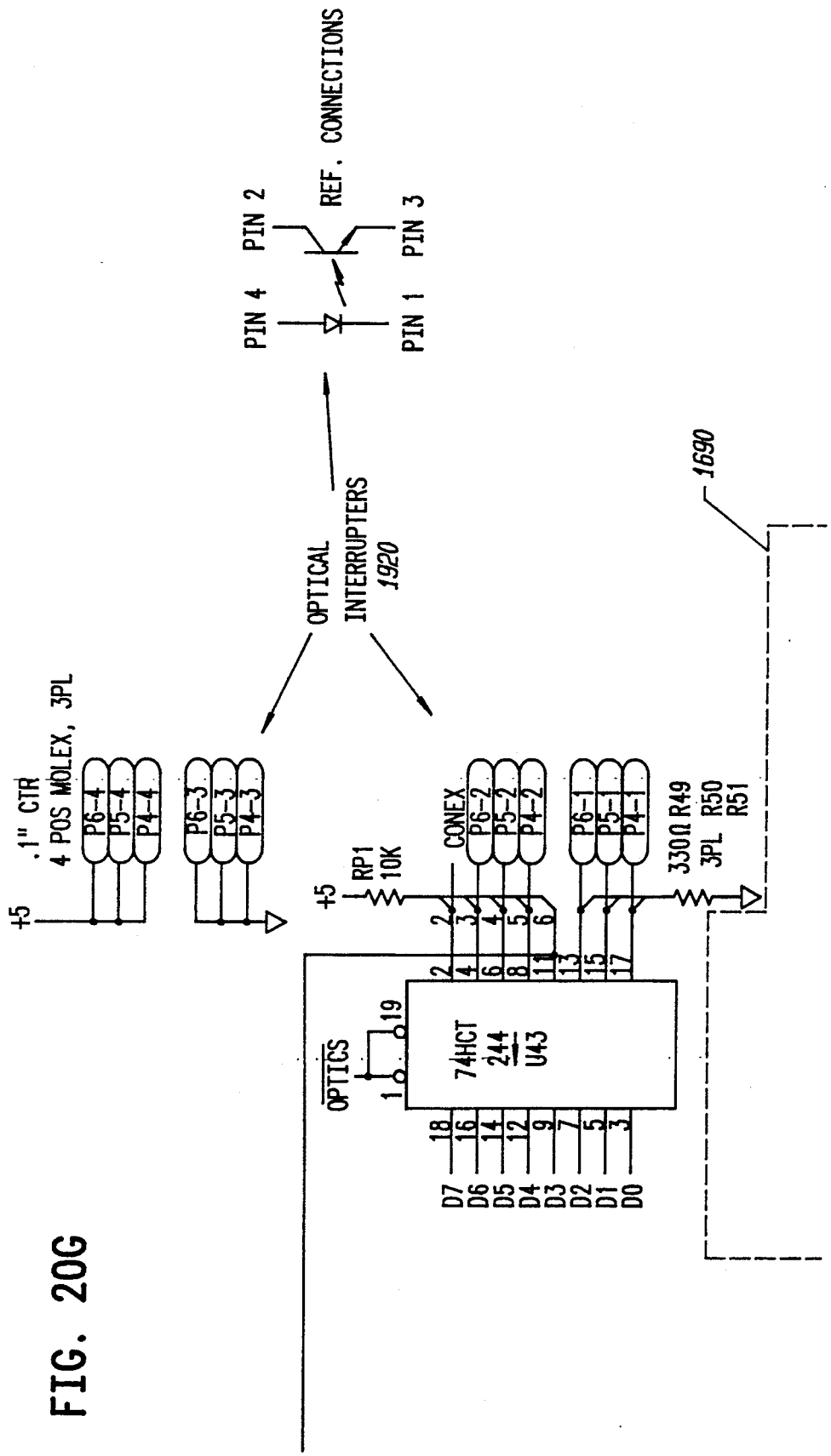
Figure 20H:
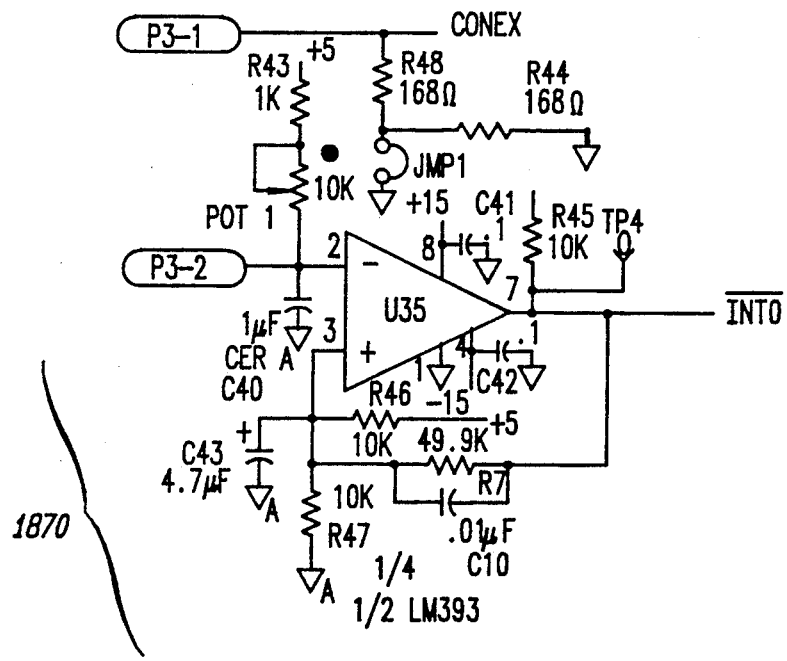
Figure 20J:
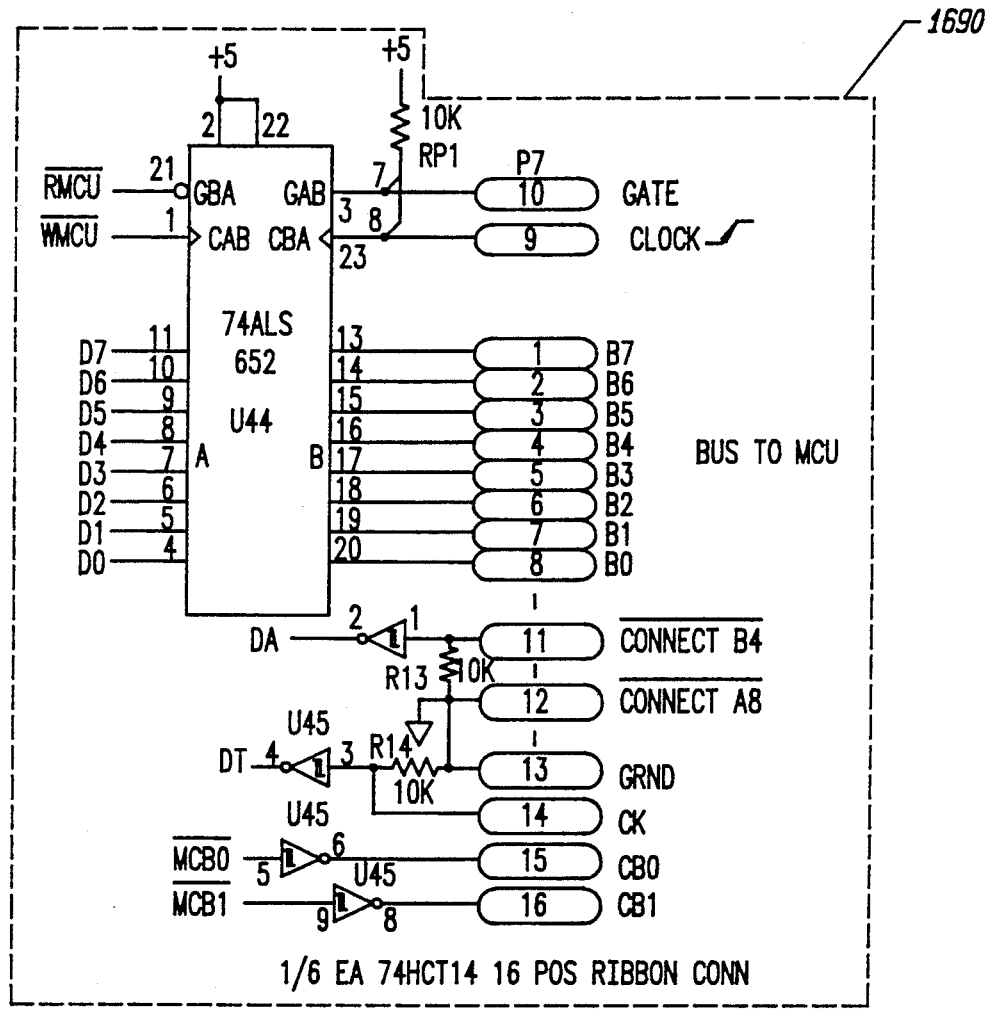
Figure 21A:
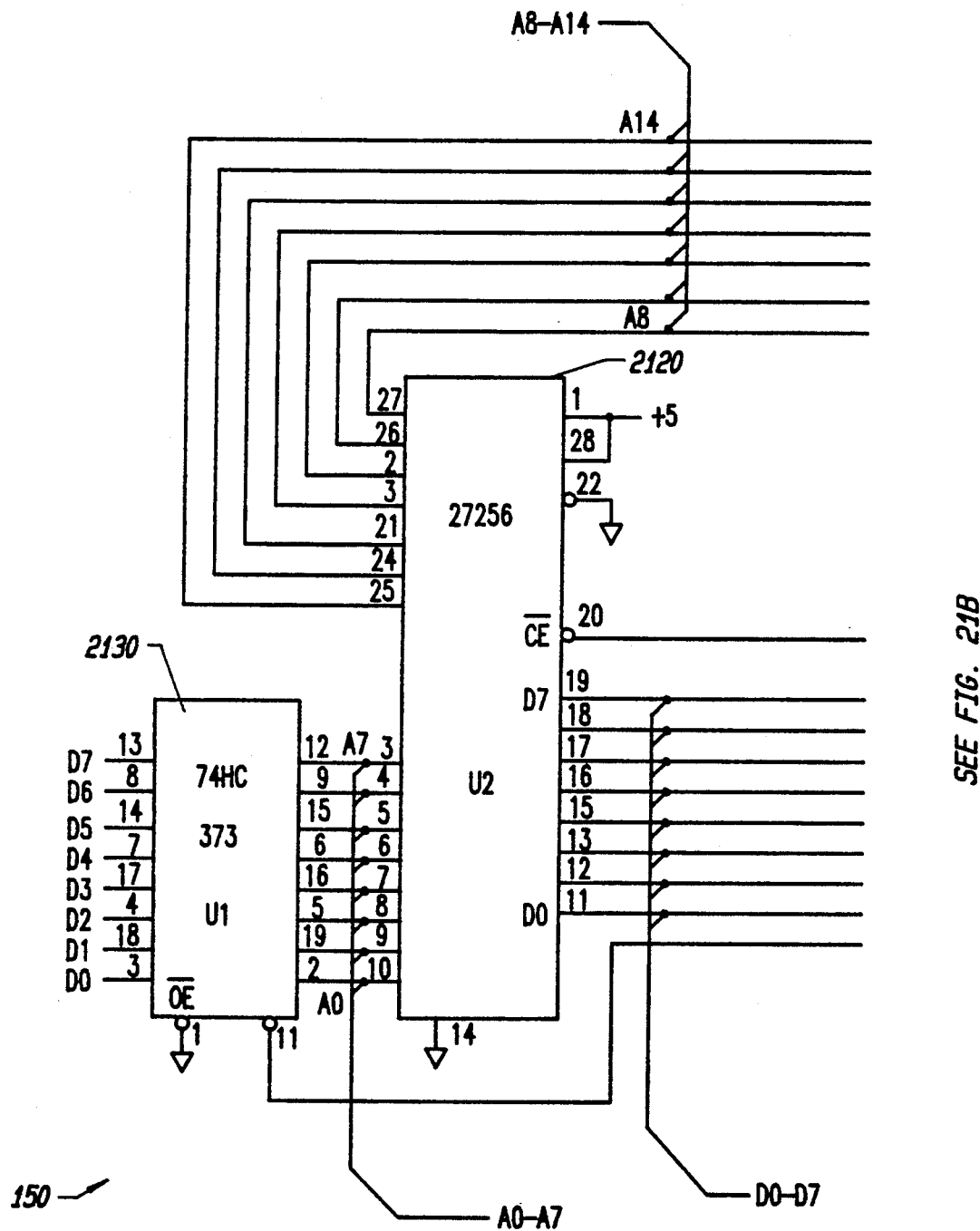
Figure 21B:
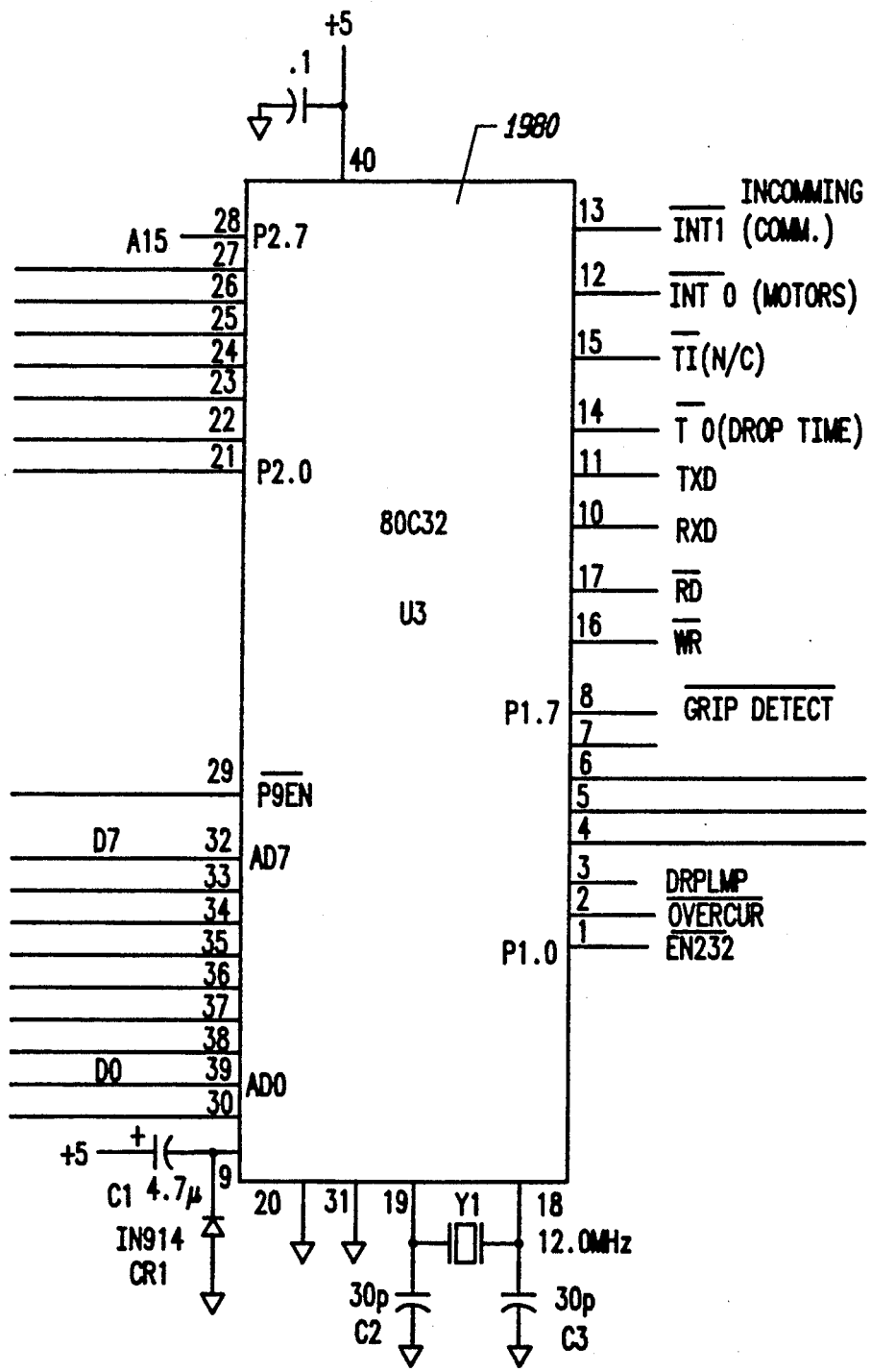
Figure 21C:
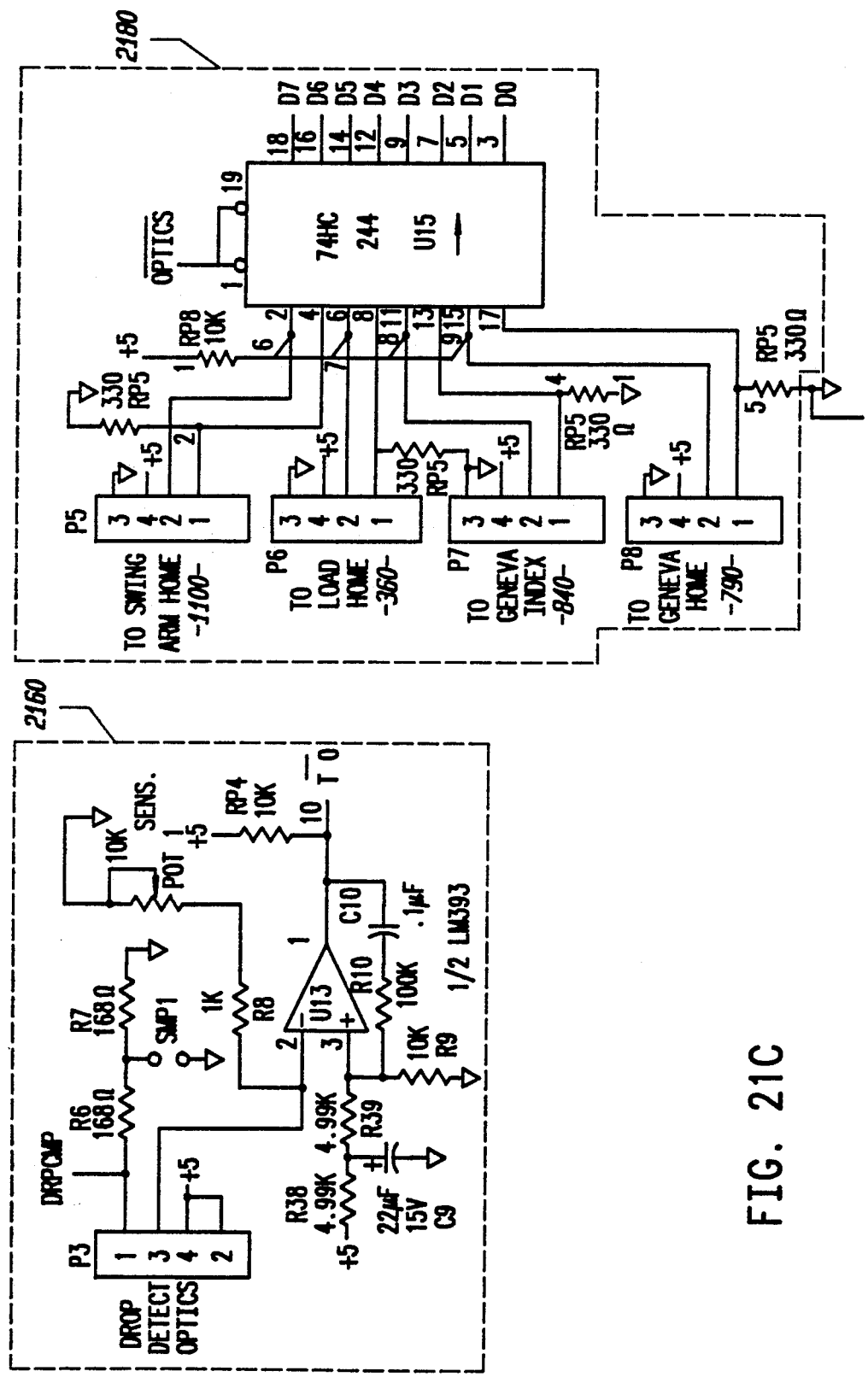
Figure 21D:
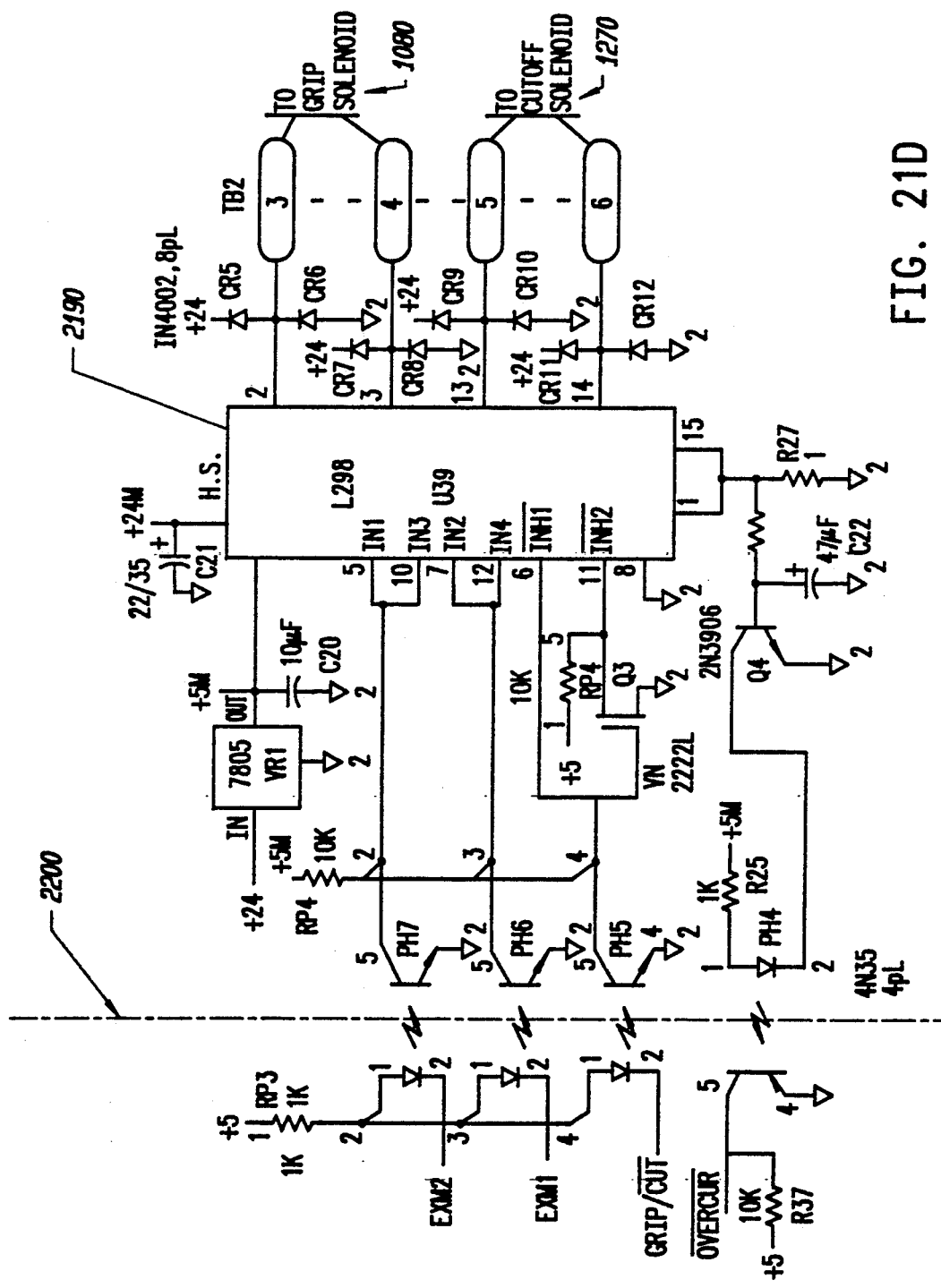
Figure 21E:
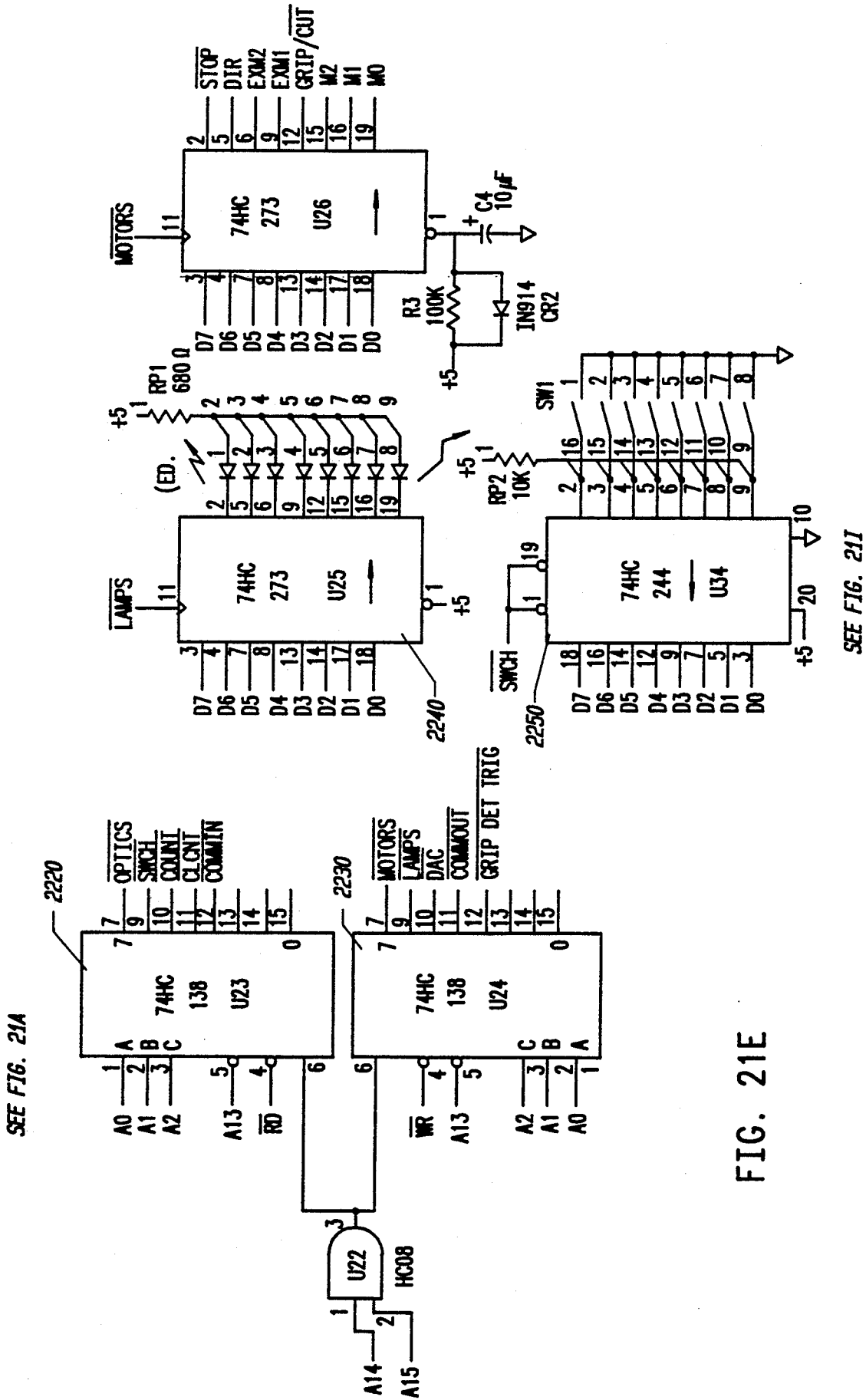
Figure 21F:
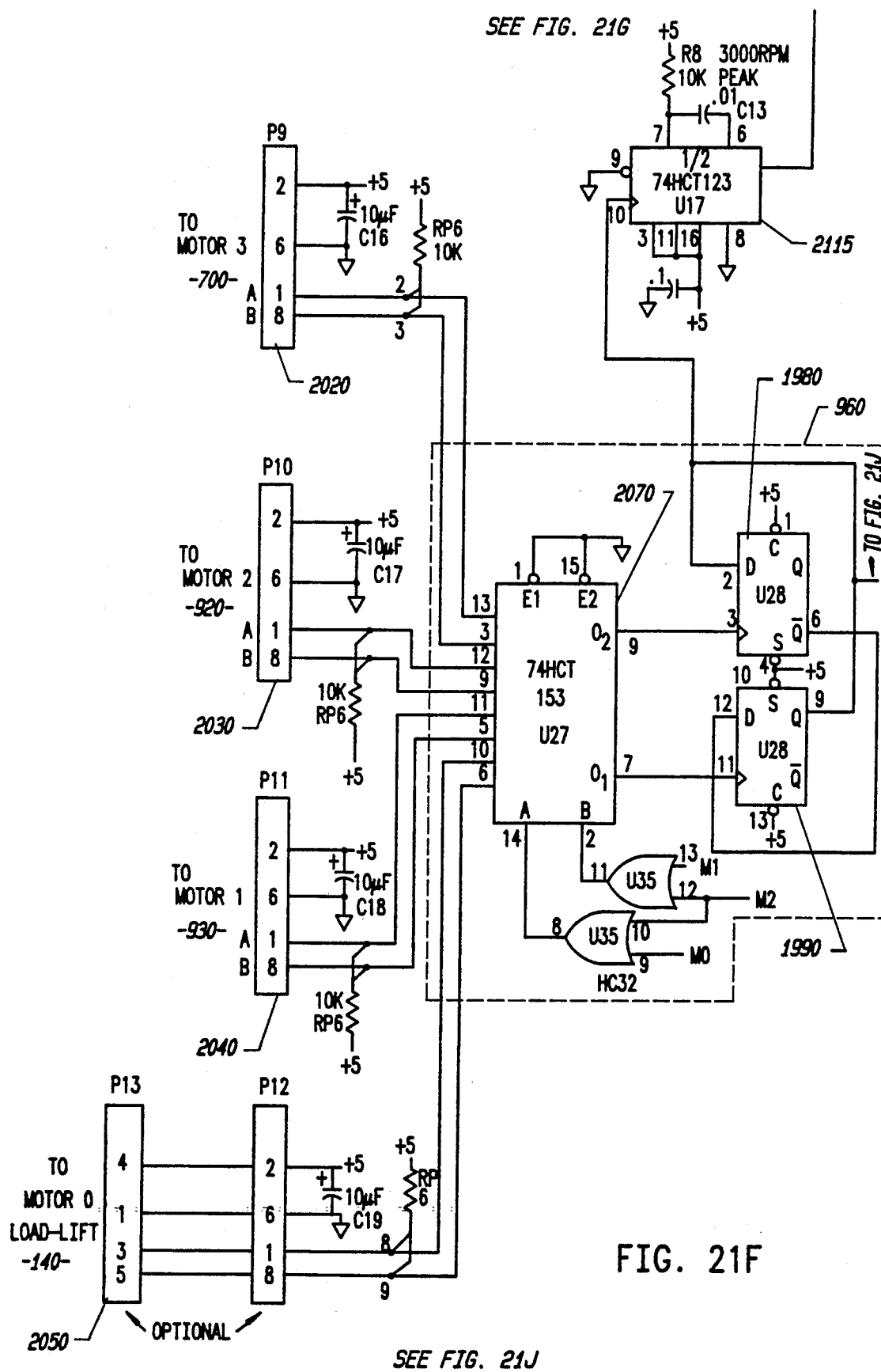
Figure 21G:
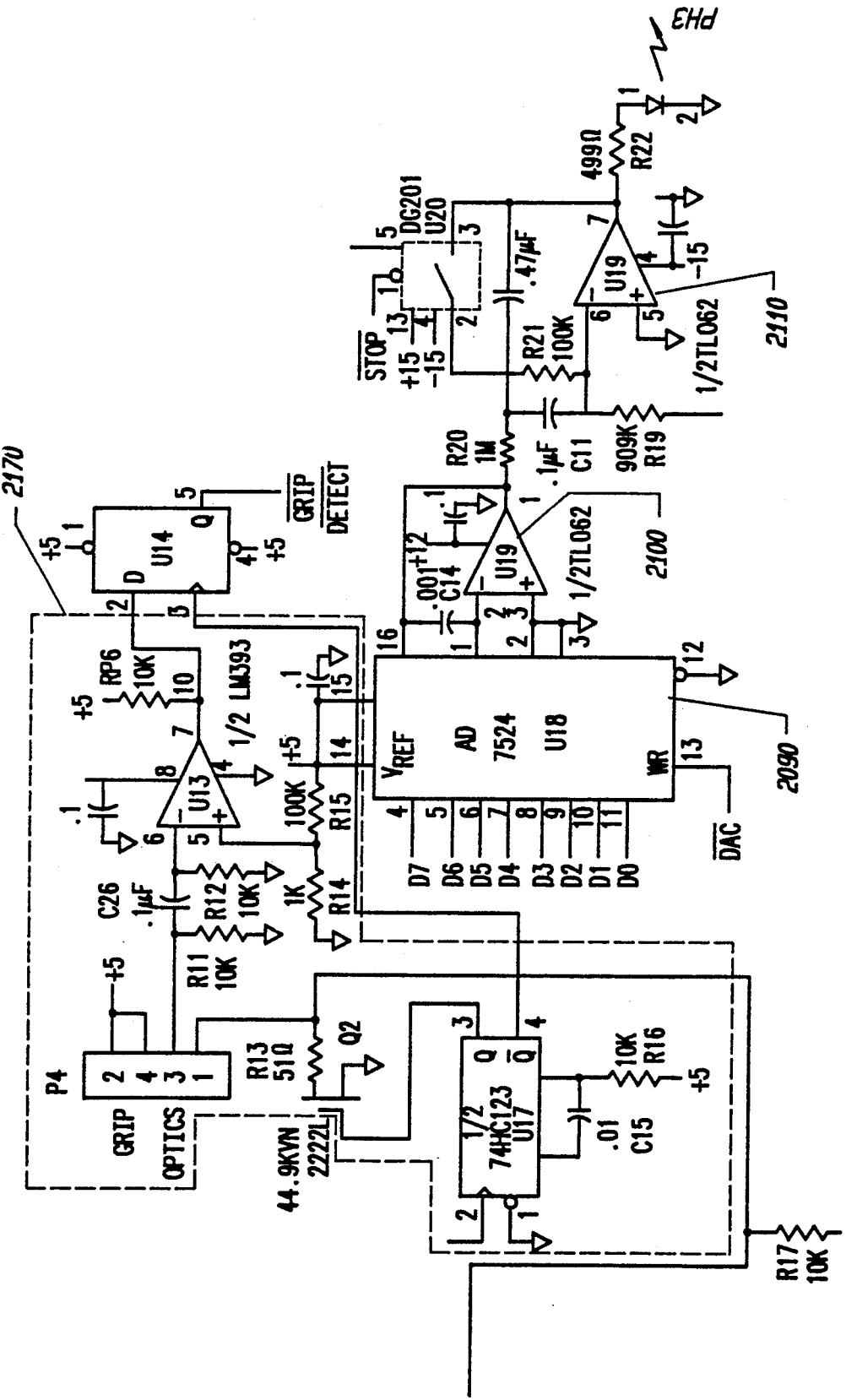
Figure 21H:
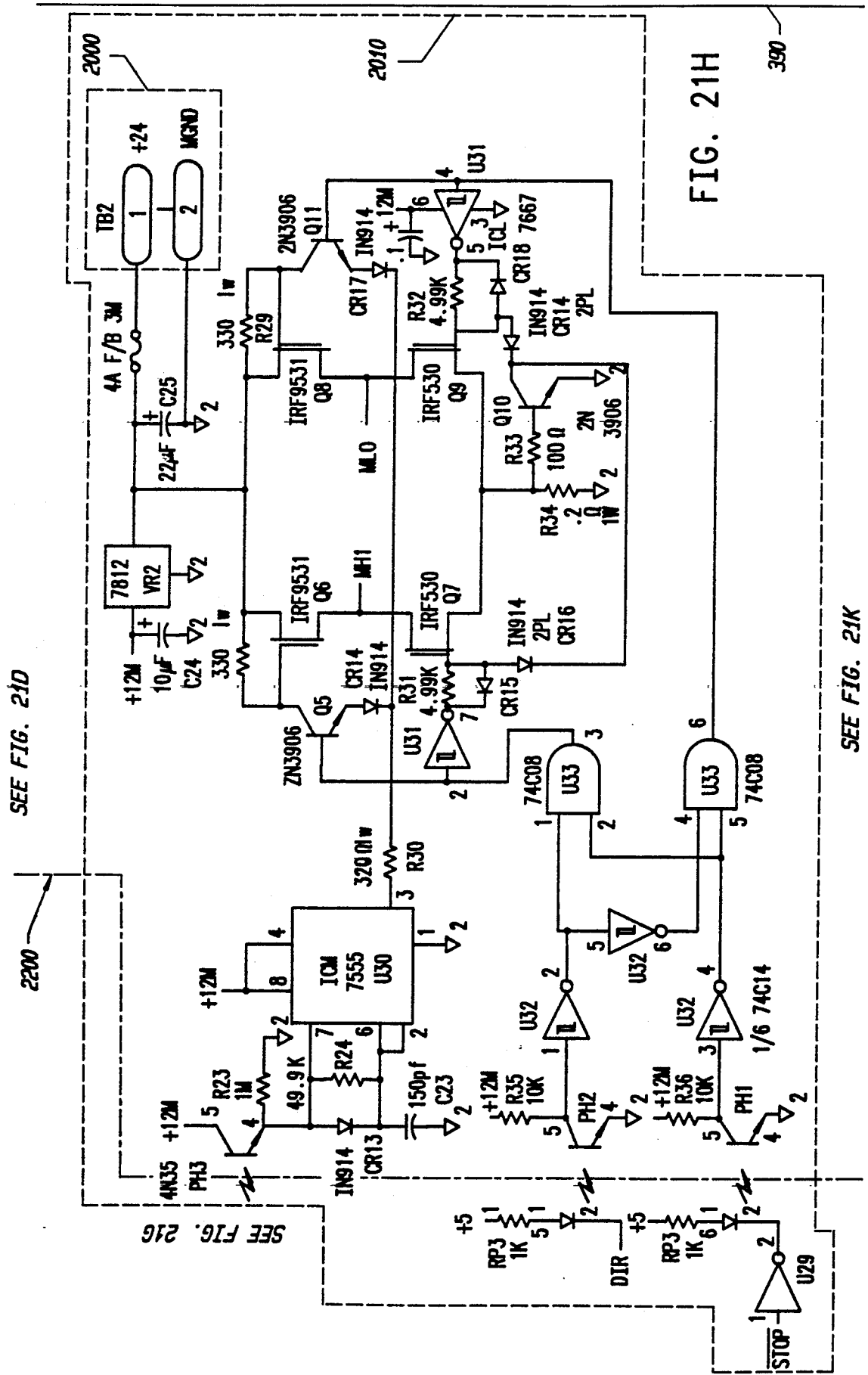
Figure 21I:
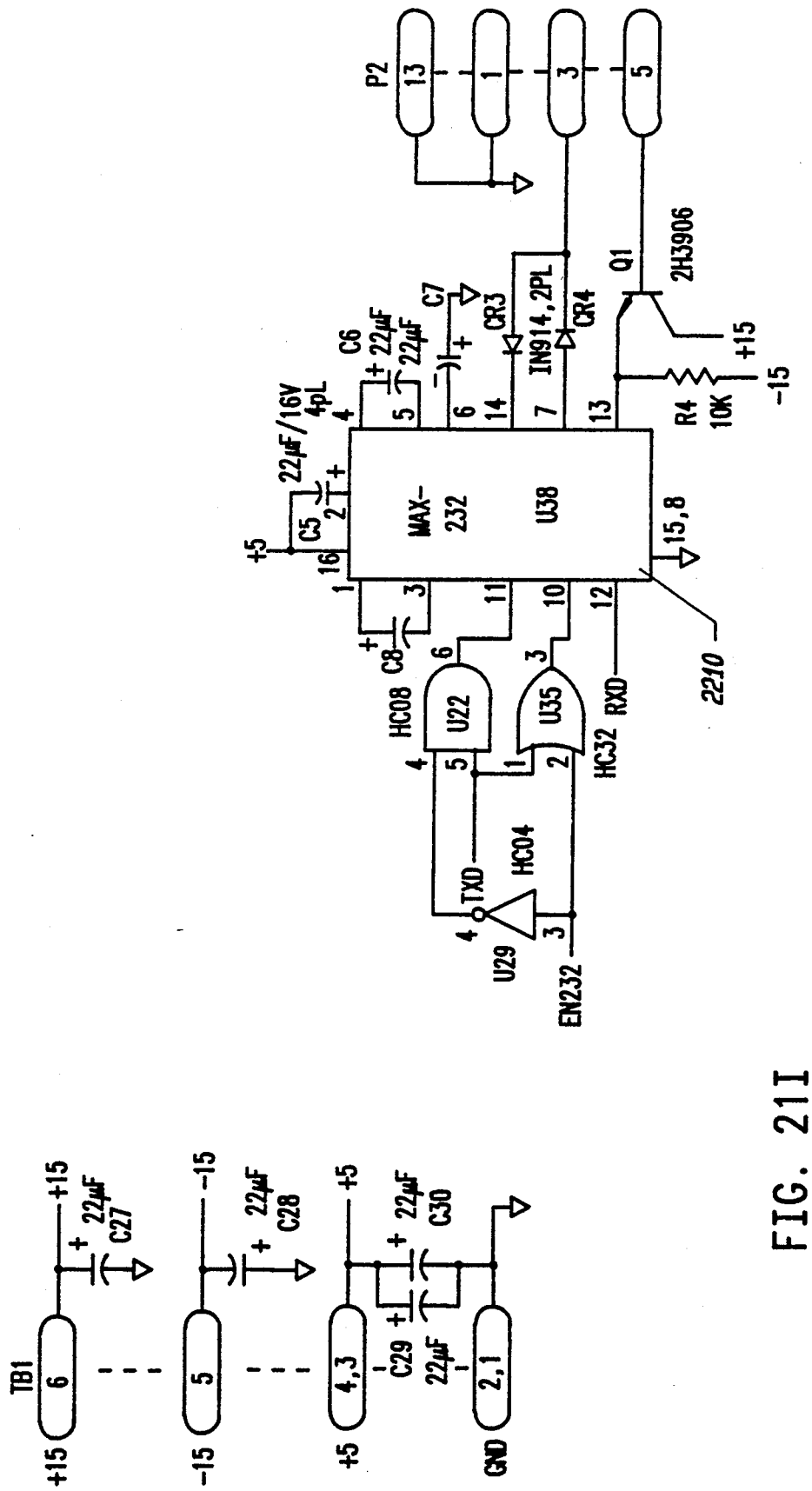
Figure 21J:
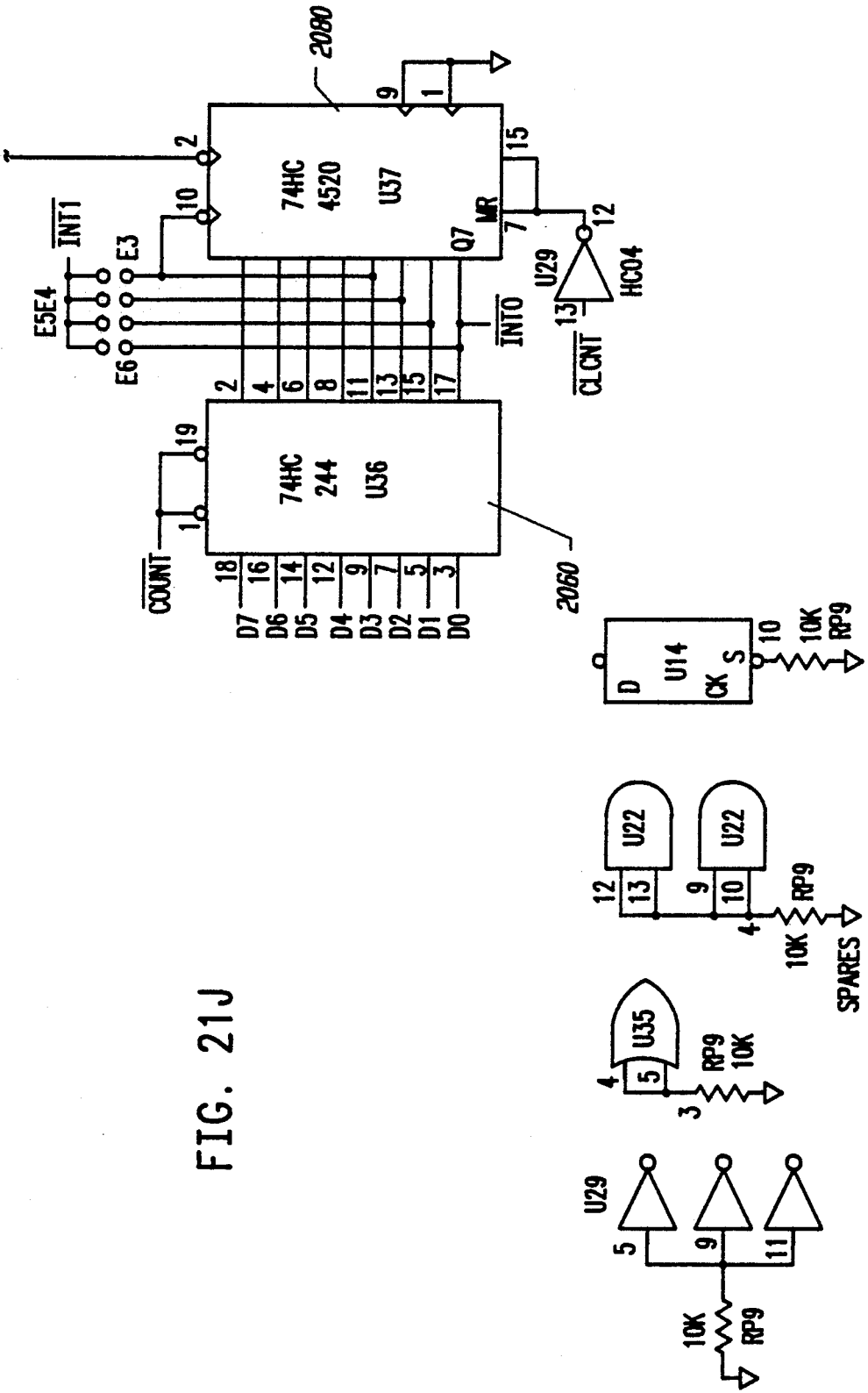
Figure 21K:
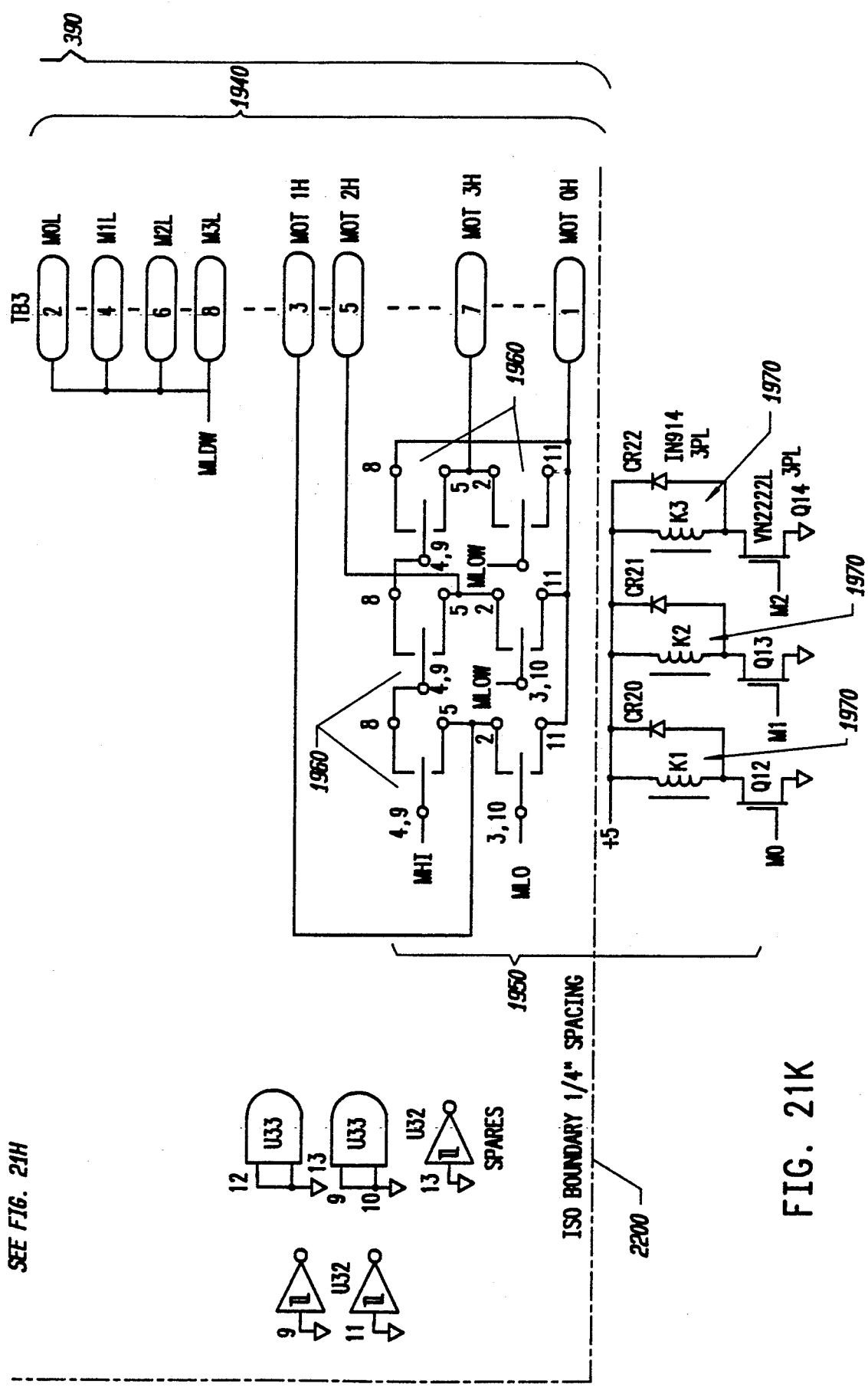
Figure 21L:
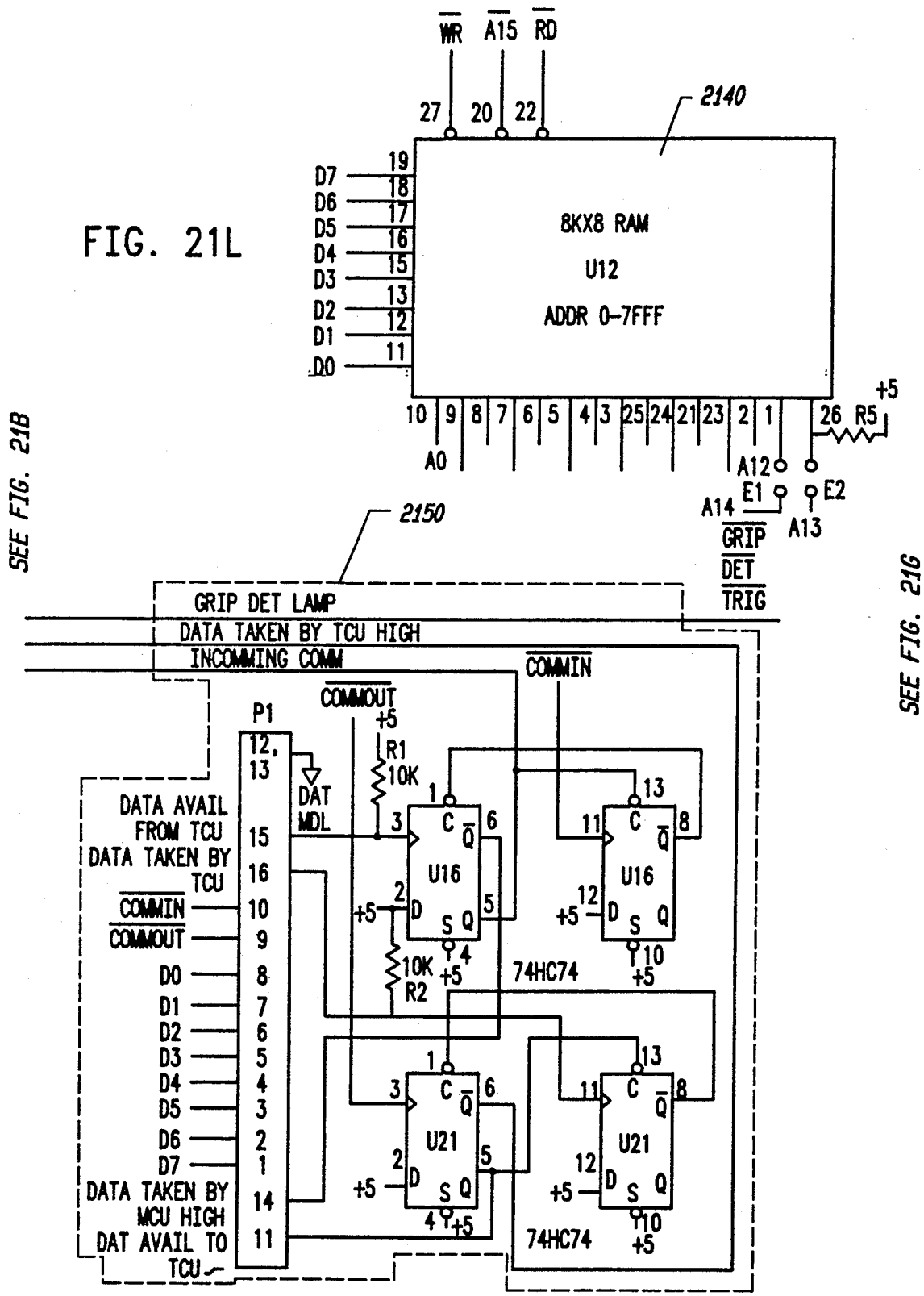

A 16-bit analog-to-digital converter 1790 (such as a Burr-Brown AD72IG) is provided, and is coupled to wires 1792, 1794, 1796 and 1798, as shown in FIGS. 18, 20 and 20A. The wiring to the PRT 500 is accomplished as in FIG. 20A, wherein a temperature-dependent variable resistor 1800 is used. A current is supplied through the resistor 1800, by means of wires 1794 and 1796, and the voltage drop across the resistor 1800 is measured by means of wires 1792 and 1798. This avoids inaccuracies which may result from measuring the voltage by utilizing wires 1794 and 1796, since these wires will have their own internal resistances, which will tend to throw off the voltage reading. Thus, four wires in all are utilized.

Circuitry 1810 acts as a current source, and a reference resistor 1820 is provided. A multiplexer 1830 measures the voltage over wires 1794 and 1796, and also measures the voltage across the reference resistor 1820, which is preferably a high-precision resistor, in the preferred embodiment having a value of 200 Ohms plus or minus 0.01%. The same amount of current is provided through the resistor 1800 and the resistor 1820, and, when the voltage is measured across the resistance 1820, the current therethrough may be determined by dividing the precisely known resistance of 200 Ohms by the measured voltage. The voltage measured across the resistor 1800 is then divided by this calculated current, to determine a precisely known value for the resistance 1800. This resistance value is provided by the multiplexer 1830 as an output to a gain block 1840, which amplifies the signal to the proper range for the A-D converter 1790. A sample and hold circuit 1850 is used for inputting the output of the gain block 1840 to the A-D converter 1790. Bus driver isolation chips 1850 are provided between the A-D converter 1790 and the main bus.

A distinct advantage of the circuitry shown in the upper left of FIG. 20 is that it requires only a single precision component. Often in conventional circuitry, a resistance bridge will be utilized for measuring resistances. However, this requires several high-precision components (such as four resistors), which are expensive. In addition, the circuitry of FIG. 20 provides better sensitivity than a conventional resistance bridge.

The switches 1862, 1864 and 1866 steer current from the current source 1810 to the PRT500 and the reference resistor 1820.

An advantage of the power output circuitry for the heating elements 462 and 464, as provided by the power source 1770, is that, with the present design, a highly monotonic and reliable power level is achieved. In addition, high precision is achieved due to the fact that the incoming signal is divided into numerous parts, and is digitally controlled.

At the lower left of FIG. 20 is shown sensor circuitry 1870 which may be used for detecting the windows 350, 352, 354, 356 and 358 (see FIGS. 11 and 12).

A switch register 1880 is provided, having manual switches 1890 which are programmed by means of the microprocessor 40. The switch register 1880 is used for manual testing and debugging of the temperature control unit 510. A lamp register 1900, having light-emitting diodes (LEDs) 1910 coupled thereto, is also provided, and like the switch register 1880, is used for manual testing and debugging of the TCU circuitry.

Additional optical interrupters are provided for, although these are not used in the above-described embodiment of the invention. An RS232 port 1930 is provided, and may be utilized for debugging the TCU 510 when the MCU 150 is not running. Thus, a microprocessor may be connected directly to the TCU 510 via the RS232 bus circuitry 1930.

FIG. 21 shows the motor control unit 150 circuitry. The outputs 1940 of this circuitry are shown at the right of FIG. 21, and are connected to the lift motor 140, the star wheel motor 700, the angle control motor 920, and the height control motor 930.

Relays 1950 utilizing six relay contacts 1960 are provided, with the relay contacts being double-pole, double-throw switches. Two relay contacts 1960 are activated by each of three solenoids 1970, and the solenoids 1970 are in turn driven over lines M0, M1 and M2 by a microprocessor (preferably an Intel 80C32) 1980 shown in FIG. 21. The microprocessor 1980 controls the relay circuitry 1950 so as to apply power to one motor while shorting out the other three motors. The shorted motors provide electromagnetically-induced resistance to any motion imposed by external forces.

It will be noted that the circuitry 960 is provided with the same input lines, M0, M1 and M2 that the relay circuitry 1950 is provided. Chips 1980 and 1990 acts as flip-flops for the circuitry 960.

Input voltage for the D.C. motors is provided at input 2000, and the motor driving circuitry 2010 acts as a chop-drive for the motors, providing the D.C. a signal in much the same way as the circuitry associated with the comparator 1700 divides up the input A.C. signal. It will be noted that the "MHI" and "MLO" lines of circuitry 2010 (standing for "motor high" and "motor low") are the same as the "MHI" and "MLO" portions shown in the relay circuitry 1950.

Connected to the circuitry 960 are encoders 2020, 2030, 2040 and 2050, which are in turn coupled to the star wheel motor 700, the angle control motor 920, the height control motor 930, and the lift motor 140, respectively. A bus buffer 2060 is also coupled to the circuitry 960. The output of the chip 2070 of circuitry 960 in effect debugs the encoder pulses to ensure that, for instance, a vibrating or wobbly motor does not send a signal as if it is rotating.

A counter 2080 is provided. When a given motor is to be utilized to move a mechanism (such as the lift mechanism 50) from one position to another, the microprocessor 1980 determines at what velocity the motor (such as lift motor 140) should turn to drive the motor to that position. The counter 2080 is set to 0, and as the motor 140 rotates, the detector circuitry of the apparatus 1558, shown in FIG. 18, provides a signal indicating the number of turns which the motor in question makes. Once the motor in question has made sufficient turns to top out the counter 2080 (at a count of 256), a "1" is provided to buffer 2060, which in turn provides this as output to the microprocessor 1980. When the microprocessor 40 detects that the motor in question has come near to the desired finishing position, then it begins to deliver commands for the motor to slow down, until the finished position is actually reached.

In order to accomplish this, the microprocessor 1980 sends a digital number representing the desired motor velocity to a digital-to-analog converter 2090, which converts the signal to an analog signal proportional to the desired velocity, and provides this signal as input to a differential amplifiers 2100 and 2110 which computes the difference between the desired velocity and the actual velocity, thus serving as a servo mechanism for the motor being driven. The microprocessor 1980 then accounts for the position of the motor by adjusting the signal which is input to the D-A converter 2090 accordingly.

The microprocessor 1980 has a program ROM 2120 and a data latch 2130 is connected to the ROM 2120. A RAM 2140 is also coupled to the microprocessor 1980.

Interprocessor communication circuitry 2150 shown in FIG. 21 acts in cooperation with interprocessor communications circuitry 1690 shown in FIG. 20 for communication between the motor control unit 150 and the temperature control unit 510.

Shown at the top of FIG. 21 is circuitry 2160 for detecting motion of the drop flag 340 shown in FIG. 2. Similarly, grip optics detection circuitry 2170 is coupled to the emitter 1560 and the detector 1565 shown in FIG. 6, and is utilized to determine whether a cartridge 550 is present, as described above.

Encoder circuitry 2180 is provided for converting interrupted signals of the optical detectors 360, 790, 840 and 1100 to a binary code (such as a 0 for an interrupted signal, and a 1 for an uninterrupted signal), and the output of the circuitry 2180 is provided to the microprocessor bus. The microprocessor 1980 is programmed to occasionally check for home position data on the bus.

A power driver chip 2190 is provided to supply current to solenoids 1080 and 1270 as shown in the top right of FIG. 21. Power demand information is received from the left side of the power driver chip 2190, and it will be seen from FIG. 21 that the power circuitry is in general isolated from the remainder of the motor control unit circuitry by an isolation boundary 2200.

An RS232 interface 2210 is provided, as are address decoding support chips 2200 and 2230.

A lamp register 2240 and a switch register 2250 are provided, as shown on the left side of FIG. 21, and, as with the lamp register and switch register 1880 shown in FIG. 20, are utilized to debug and test the circuitry (in this case, the circuitry of the motor control unit 150). Finally, coupled between the amplifiers 2100, 2010 and the circuitry 960 is a one-shot 2115.

It will be understood that the foregoing is a description of a particular embodiment incorporating features of the method and apparatus of the invention, and other implementations of the invention may be utilized.

*APPENDIX A*.

TCU.HEX  Tuesday, October 11, 1988 2:38 pm
File Created: Tuesday, October 11, 1988 2:37 pm :1007DB0074027800790412070A900B2DE0FAA3E05B
:1007EB004A6015900B2DE0FAA3E0FB8B05BA047B86
:1007FB00007A80120448B0051204A70400900B2D88
:100B0B00EAF0EBA3F002074EE47800790412070A32
:10081B007B007A00900B2DEAF0EBA3F002074EE47D
:10082B007800790412070A900B2DE0FAA3E0FB02B3
:10083B00074EE47800790412070A7B00900018BEBDA
:10084B00F07B0090018CEBF002074EE4780079040A
:10085B0012070A900E4EE0FB8B05900E4FE0FB1239
:10086B00025502074EE47800790412070A900E4EE7
:10087B00E0FB8B05900E4FE0FB120246600280ED11
:10088B007B507A0E12038101 7B007A00BB058A0460
:10089B007B4F7A0E12037B017A001205318A838B10
:1008AB0082E0FB7A0002074E74027800790412078B
:1008BB000A900E4DE0700280F812049B05008B9994
:1008CB007B00900E4DEBF002074E74027800790519
:1008DB0012070A7B001204FE04001204A705008B0A
:1008EB00058A0412049B04007A001205318A838B5B
:1008FB0082E0603712049B04008B057B6412023686
:10090B0060291204A70500B058A0474042FFBE4ED
:10091B003EFA12037B017A001205318A838B82E047
:10092B00FB7A009000021208B380AF02074E7402EC
:10093B007800790512070A7B01900257EBF09001C2
:10094B0000E0FB900258EBF09000001208 2AEB4AF3
:10095B0060047B2180027B2E900259EBF07B02908E
:10096B00025AEBF07B041204FE04001204A70500EC
:10097B008B058A0412049B04007A001207818B05F5
:10098B00BA047BFC7AFF1205311207961205318A15

```
:10099B00838B82E0606312049B04008B057B6412E3
:1009AB0001F960551204A705008B058A0412049BFC
:1009BB0004007A001207818B058A047BFC7AFF12F4
:1009CB000531120796120531BA838B82E0FBBB056A
:1009DB007B577A021207738B058A0412049B05005E
:1009EB007A0012053112078F12045074042FFBE4A6
:1009FB003EFA12037B010209767B008B057B577A4B
:100A0B00021207738B058A0412049B05007A0012ED
:100A1B000531120 78F12045002074EE47800790556
:100A2B0012070A7B001204FE040012049B04008BC5
:100A3B000590018CE0FB1201F960427B8D7A018BF2
:100A4B00058A0412049B04007A00120531BAB3BBF9
:100A5B0082E0FBBB057BF27A011207738B058A040C
:100A6B0012049B05007A0012053112078F120450F5
:100A7B0074042FFBE43EFA12037B0180AD7B008BE9
:100A8B00057BF27A011207738B058A0412049B050E
:100A9B00007A0012053112078F12045002074EE440
:100AAB007800790412070A7B0090025AEBF00207D8
:100ABB004EE47800790412070A7B019001F2EBF007
:100ACB00900100E0FB9001F3EBF09000 00120B2A7C
:100ADB00EB4A60047B2180027B2E9001F4EBF07BD0
:100AEB00029001F5EBF07B0A9001F6EBF07B0090A6
:100AFB0001F7EBF002074EE47800790D12070A7B41
:100B0B000012 04FE05007B041204FE04007B00901F
:100B1B000AB4EBF07B001204FE09007BF27A018B26
:100B2B00058A0474042FFBE43EFA12037B017A005E
:100B3B001205318A838B82E0FB1204FE06007003E0
:100B4B00020C0212049B06008B057B2012023660FE
:100B5B005912049B050060507B001204FE05007BBC
:100B6B00008B057BBC7A021207738B058A04900AF3
:100B7B00B4E0FB7A0078 0312027F00641205311295
:100B8B00078F1207738B058A0412049B0A007A00E5
:100B9B0012053112078F1204507B001204FE09005C
:100BAB007BB47A0A12037B01804A7B011204FE0597
:100BBB000012049B06008B057BBC7A021207738B19
:100BCB00058A04900AB4E0FB7A00780312027F00D6
:100BDB0064120531120 78F120773BB058A04740A8E
:100BEB002FFBE43EFA12037B017A00120531120748
:100BFB000F120450020B267B001204FE0800120415
:100C0B009B08008B05900AB4E0FB1201F9700302FC
:100C1B000F457B001204FE09007B008B057BB57A2B
:100C2B000A1207738B058A0412049B09007A0012BF
:100C3B00053112078F1204507BBC7A028B058A0494
:100C4B0012043B007A00780312027F00641205DD
:100C5B00318B058A0474092FFBE43EFA12037B01E6
:100C6B007A001205318A838B82E0FB1204FE0600A8
:100C7B007003020F3712049B06008B057B301202A8
:100C8B0029601212049B06008B057B391202366019
:100C9B00047B0180027B001204FE0A0012049B0AF3
:100CAB000601112049B06008B057BD0EB2DFB1211
:100CBB0004FE0C0012049B06008B057B66120236A9
:100CCB00601C12049B06008B057B61120229600ECF
:100CDB0012049B06008B057BE0EB2DFB0051204B9
:100CEB009B06001204FE070012049B0A00702012E0
:100CFB00049B07008B057B41120229600E12049B9B
:100D0B0007008B057B4612023670047B0080027B4A
:100D1B00011204FE0B0012049B0B00601F12049BBC
:100D2B000A00600712049B0C00800C12049B070046
:100D3B008B057BBFEB2DFB1204FE0C007BB57A0AF7
:1004DB008B058A0412049B08007A001205318A83F2
:100D5B008BB82E0FB1206450D72000DEB010DEB02D4
:100D6B000ECC0300000F3212049B0A00604D7B0275
:100D7B008B057BB57A0A1207738B058A0412049BC9
:100D8B0009007A001205311 2078F120450124049BCE
:100D9B000C007A00BB058A047B8C7A0A1207818BF4
:100DAB00058A0412049B0A007A00EB2BFBEA3AFA41
:100DBB0012053112079612045BB01F7B018B057B9D
:100DCB00B57A0A1207738B058A0412049B09007A01
:100DDB0000012053112078F1204500 20F34020F3428
:100DEB0012049B0A00606178BC7A0ABB058A0412C1
:100DFB00049B08007A00EB2BFBEA3AFA1205318AC6
:100E0B00838B82E0FAA3E0FBBB058A047B0A7A00D2
:100E1B001205428B058A0412049B0C007A00120502
:100E2B00318B058A047B8C7A0A12078188058A0425
:100E3B0012049B0A007A00EB2BFBEA3AFA120531FB
:100E4B001207961204588077120 49B06008B057BC1
:100E5B007B12046604A7B038B057BB57A0A120730
:100E6B00738B058A0412049B09007A001205311258
:100E7B00007BF1204507B007A00BB058A047BBC7AD7
:100E8B0000A1207818B058A0412049B0A007A00EB75
:100E9B002BFBEA3AFA12053112079612045BB01FFF
:100EAB007BFF8B057BB57A0A1207738B058A0412BD
:100EBB00049B09007A00120531120 78F120450802F
:100ECB006B12049B0B00605D7BBC7A0A8B058A04BD
:100EDB0012049B08007A00EB2BFBEA3AFA1205315D
:100EEB00BA838BB82E0FAA3E0FBBB058A047B0412D6
:100EFB0003FD8B058A0412049B0C007A001205314A
:100F0B008BB058A047B8C7A0A1207818B058A041263
:100F1B00049B0A007A00EB2BFBEA3AFA120531121A
:100F2B000079612045BB0028000020C4374082FFBB2
:100F3B00E43EFA12037B01020C0902074EE478002F
:100F4B000790612070A7B001204FE050090000012BE
:100F5B0000856EB70030210412049B050060030202C9
:100F6B0010D49000001208701204FE04008B057B55
:100F7B000112024660069000001208 3D12049B0409
:100F8B00008B057BBD7A011207738B058A047B8C92
:100F9B007A01 12037B017A001205311 2078F1204BA
:100FAB005090018BEE0FB1206450FC4000FEB0110B4
:100FBB000E021093030000010CF7B001204FE0500FD
:100FCB0012049B04008B057B0112024660097B0116
:100FDB00900018BEBF0806900000120083D0210D1BF
:100FEB0012049B0400BB05900100E0FB12024660BB
:100FFB00097B02900 18BEBF08006900000120083DFC
:10100B00210D112049B0400120645103B61106BBC
:10101B006410566710297010767400000107F7BF2F5
:10102B007A019000021208D590000001208 3D8056FC
:10103B0090000001208029000001208ABC7B01120FC
:10104B00FE05009000001208 3D803B7B577A029012
:10105B000000021208D5900000012083D80299000074
:10106B00120AAA9000001208 3D801B7B0390018B93
:10107B00E0F08012900000 01208307BE97A039000A0
:10108B00021207DBB0000803E9001BCE0FBBB057B1E
:10109B0064120 1C7601 2900000120083D7BEA7A03CC
:1010AB009000002120 7DBB01A12049B0400BB057B55
:1010BB00A120246600C900000120A2690000012E1
:1010CB00083D8002B000020F5712049B0500020 7A7
```

```
:1010DB004E74027800790512070A7B001204FE0495
:1010EB00007B2F7A0B12077A1204A70700900004DB
:1010FB00121C97EB4A703C7B1B7A0E900182EAF034
:10110B00EBA3F07B2B7A0E900184EAF0EBA3F07B40
:10111B0002900186EBF07B397A0E900187EAF0EBB7
:10112B00A3F07B809001B9EBF07B011204FE04009D
:10113B000216FE7B347A0B12077A1204A707009073
:10114B0000004121C97EB4A703C7B1D7A0E900182B7
:10115B00EAF0EBA3F07B2D7A0E900184EAF0EBA37F
:10116B00F07B029001B6EBF07B397A0E900187EAD7
:10117B00F0EBA3F07B40900189EBF07B011204FEB6
:1011BB0004000216FE7B3A7A0B12077A1204A707A9
:10119B00009000 04121C97EB4A703C7B1F7A0E9058
:1011AB000182EAF0EBA3F07B2F7A0E900184EAF03B
:1011BB00EBA3F07B02900186EBF07B397A0E9016A
:1011CB00B7EAF0EBA3F07B209001B9EBF07B011217
:1011DB0004FE04000216FE7B3F7A0B12077A120400
:1011EB00A70700900004121C97EB4A703C7B217AF6
:1011FB000E900182EAF0EBA3F07B317A0E90018422
:10120B00EAF0EBA3F07B02900186EBF07B397A0ED0
:10121B00900187EAF0EBA3F07B10900189EBF07B58
:10122B00011204FE04000216FE7B447A0B12077AAD
:10123B001204A70700900004121C97EB4A703C7B2A
:10124B00237A0E900182EAF0EBA3F07B337A0E90B7
:10125B000184EAF0EBA3F07B02900186EBF07B3983
:10126B007A0E900187EAF0EBA3F07B089001B9EBF3
:10127B00F07B011204FE04000216FE7B4A7A0B126D
:10128B00077A1204A70700900004121C97EB4A7010
:10129B003C7B257A0E900182EAF0EBA3F07B357A4A
:1012AB000E900184EAF0EBA3F07B02900186EBF049
:1012BB007B397A0E900187EAF0EBA3F07B04900167
:1012CB00B9EBF07B011204FE04000216FE7B4F7AC1
:1012DB000B12077A1204A70700900004121C97EB5D
:1012EB004A703C7B277A0E900182EAF0EBA3F07BED
:1012FB00137A0E900184EAF0EBA3F07B0290018647
:10130B00EBF07B397A0E900187EAF0EBA3F07B02CE
:10131B009001B9EBF07B011204FE04000216FE7BAB
:10132B00527A0B12077A1204A70700900004121CC2
:10133B0097EB4A703C7B297A0E900182EAF0EBA383
:10134B00F07B177A0E900184EAF0EBA3F07B02900E
:10135B000186EBF07B397A0E900187EAF0EBA3F074
:10136B007B019001B9EBF07B011204FE04000216555
:10137B00FE7B567A0B12077A1204A7070090000423
:10138B00121C97EB4A703C7B157A0E900182EAF0A7
:10139B00EBA3F07B157A0E900184EAF0EBA3F07BC4
:1013AB0001900186EBF07B3A7A0E900187EAF0EB25
:1013BB00A3F07B809001B9EBF07B011204FE04000B
:1013CB000216FE7B597A0B12077A1204A707009BC
:1013DB0000004121C97EB4A703C7BFC7A0D9001B247
:1013EB00EAF0EBA3F07BFC7A0D900184EAF0EBA31F
:1013FB00F07B02900186EBF07B3A7A0E900187EA44
:10140B00F0EBA3F07B809001B9EBF07B011204FEE3
:10141B0004000216FE7B5C7A0B12077A1204A707F4
:10142B00000900004121C97EB4A703C7BFE7A0D90E7
:10143B000001B2EAF0EBA3F07BFE7A0D900184EAF0D7
:10144B00EBA3F07B02900186EBF07B3A7A0E9001D6
:10145B0087EAF0EBA3F07B809001B9EBF07B011224
:10146B0004FE04000216FE7B607A0B12077A12044C
:10147B00A70700900004121C97EB4A703C7B007A84
:10148B000E900182EAF0EBA3F07B007A0E900184C0
:10149B00EAF0EBA3F07B02900186EBF07B3A7A0E3D
:1014AB00900187EAF0EBA3F07B80900189EBF07B56
:1014BB00011204FE04000216FE7B637A0B12077AFC
:1014CB001204A70700900004121C97EB4A703C7B98
:1014DB00517A0E900182EAF0EBA3F07B517A0E90D9
:1014EB000184EAF0EBA3F07B01900186EBF07B3AF1
:1014FB007A0E900187EAF0EBA3F07B40900189EB29
:10150B00F07B011204FE04000216FE7B677A0B12BD
:10151B00077A1204A70700900004121C97EB4A707D
:10152B003C7B537A0E900182EAF0EBA3F07B537A6B
:10153B000E900184EAF0EBA3F07B01900186EBF0B7
:10154B007B3A7A0E900187EAF0EBA3F07B40900197
:10155B0089EBF07B011204FE04000216FE7B6D7A10
:10156B000B12077A1204A70700900004121C97EBCA
:10157B004A703C7B557A0E900182EAF0EBA3F07B2C
:10158B00557A0E900184EAF0EBA3F07B01900186 73
:10159B00EBF07B3A7A0E900187EAF0EBA3F07B40FD
:1015AB00900189EBF07B011204FE04000216FE7B16
:1015BB00737A0B12077A1204A70700900004121C0F
:1015CB0097EB4A703C7B577A0E9001B2EAF0EBA3C3
:1015DB00F07B577A0E900184EAF0EBA3F07B01903D
:1015EB000186EBF07B3A7A0E900187EAF0EBA3F0E1
:1015FB007B40900189EBF07B011204FE04000216 84
:10160B00FE7B797A0B12077A1204A707009000046D
:10161B00121C97EB4A703C7B597A0E900182EAF0D0
:10162B00EBA3F07B597A0E900184EAF0EBA3F07BED
:10163B0001900186EBF07B3A7A0E900187EAF0EB92
:10164B00A3F07B40900189EBF07B011204FE0400BB
:10165B000216FE7B7F7A0B12077A1204A70700903
:10166B0000004121C97EB4A703B7B5B7A0E9001 8255
:10167B00EAF0EBA3F07B5B7A0E900184EAF0EBA32C
:10168B00F07B01900186EBF07B3A7A0E900187EAB2
:10169B00F0EBA3F07B40900189EBF07B011204FE91
:1016AB000004000804F7B857A0B12077A1204A70700B0
:1016BB00900004121C97EB4A70397B5D7A0E9001F7
:1016CB0082EAF0EBA3F07B5D7A0E900184EAF0EBFB
:1016DB00A3F07B01900186EBF07B3A7A0E900187A9
:1016EB00EAF0EBA3F07B40900189EBF07B011204 55
:1016FB00FE040012049B040002074EE478007904F8
:10170B0012070A7B00900E4FEBF0900E4EEBF09011
:10171B000E50EBF07BFF900E4DEBF07BFF8BCB7BFA
:10172B0064BBCA7B34BBCB7B528B9BD2AC02074E2E
:10173B000E47800790712070A900AB4E07003021AE2
:10174B0004F7BBB7A0B12077A7BBC7A02900004 12CB
:10175B001C97EB4A6003 02182E900AB4E0FB8B0532 32
:10176B007B031202467003021B21900AB6E0FBBB32
:10177B00057B011202467003021B21900AB7E0FBA9
:10178B00BB057B021202467003 021B217B207A0321
:10179B0009000021210DCEB6071900A90E0FAA3E06B
:1017AB00FBBB058A049001B2E0FAA3E0FB12045B3C
:1017BB00900186E0FB8B057B021202466 04A90018A
:1017CB00B7E0FAA3E0FB8A B3BBB2E0FBBB05900119
:1017DB0089E0FBEB5D 600C7B647A009000021207E2
:1017EB00DBB02590 0187E0FAA3E0FB BAB3BBB2E004
:1017FB00FB8B05900189E0FBEB4DFB8B0590018783
:10180B00E0FAA3E0FB120450800A7B0A7A009000F6
```

:10181B00021207DB800A7B0B7A009000021207DBB7
:10182B00021A4D7B8D7A0B12077A7BBC7A029000E1
:10183B0004121C97EB4A6003021947900AB4E0FBB1
:10184B008B057B02120246700302193A900AB6E02E
:10185B00FB8B057B011202467003021 93A7B207A3F
:10186B000390000212I0DCEB700302192E9001B61C
:10187B00E0FB8B057B0112024660 6D900187E0FA5D
:101 88B00A3E0FB8AB3BB82E0FB8B05900189E0FB55
:10189B00EBF4FBEB5DFB8B05900187E0FAA3E0FB20
:1018AB001204507B011204FE040012049B0400601E
:1018BB0035900184E0FAA3E0FB8A838B82E0FAA3E4
:1018CB00E0FB12050405009001 87E0FAA3E0FBBA18
:1018DB0083BB82E0FB8B05900189E0FBEB5DFB12B8
:1018EB0004FE040080C4801 69001B4E0FAA3E0FBA0
:1018FB008A838B82E0FAA3E0FB1205040500120435
:10190B00A7050012077A7B8F7A0B12077A7BC97AAD
:10191B000A900006121D317BC97A0A9000021 20947
:10192B0039800A7B0C7A009000021207DB800A7B5D
:10193B000D7A009000021207DB021A4D7B937A0B93
:10194B0012077A7BBC7A02900004121C97EB4A7048
:10195B0043900AB4E0FB8B057B01120246602 89092
:10196B000B2DE0FAA3E0FB12077A7B957A0B12079B
:10197B007A7BC97A0A9000061 21D317BC97A0A90CC
:10198B000002120939800A7B0E7A009000021207BE
:10199B00DB021A4D7B997A0B12077A7BBC7A0290B9
:1019AB0000004121C97EB4A7023900AB4E0FB8B05E2
:1019BB007B011202466008900000120B13800A7B1C
:1019CB000F7A009000021207DB021A4D7B9B7A0BF9
:1019DB0012077A7BBC7A02900004121C97EB4A60C8
:1019EB00157B9D7A0B12077A7B207A0390000412E9
:1019FB001C97EB4A700AC2AC900000121706B042BB
:101A0B007B9F7A0B12077A7BBC7A0290000412lC24
:101A1B0097EB4A7023900AB4E0FB8B057B01120213
:101A2B004660097B0090018AEBF0800A7B107A00FC
:101A3B009000021207DB800A7B307A0090002I2C2
:101A4B0007DB800A7B317A009000021207DB02076A
:101A5B004EE47800 7904120 70A7B007A40900DFC63
:101A6B00EAF0EBA3F07B007A00900DFEEAF0EBA31B
:101A7B00F07B007A00900E00EAF0EBA3F07B747A17
:101A8B00A4900E13EAF0EBA3F07B0C7AA8300E1740
:101A9B00EAF0EBA3F07B507AC3900E19EAF0EBA3BC
:101AAB00F07B507A00900E2BEAF0EBA3F07BD07A10
:101ABB0007900E2DEAF0EBA3F07B007A00900E2F2F
:101ACB00EAF0EBA3F07B647A00900E31EAF0EBA323
:101ADB00F07BD57A02900E33EAF0EBA3F07B007A21
:101AEB0000900E35EAF0EBA3F07B00900E39EBF093
:101AFB007B00900E3AEBF07B00900E3BEBF07B0003
:101B0B00900E4BEBF07B06900E4CEBF07B28900E7F
:101B1B003CEBF07B2890C000EBF07BFF900E12EBC0
:101B2B000F07BFF90C004EBF07BFF8B8D7BFF8B8BEF
:101B3B00ABB9BB057B0FEB5DFBBB057B60EB4DFB6B
:101B4B008B89D28ED2AB02074EE478007904120750
:101B5B000A7B06B88CABB97A00BB05BA047BF07A27
:101B6B0000012044 08B05BA047B027A001 2044B8B16
:101B7B0089D2BC D2A9D2BBD2AB02074EE4780079F8
:101B8B000412070A7B0190018AEBF09 00000120807
:101B9B00139000001 2083D9000001 20AAA900005A
:101BAB00120ABC900000121706900000121A5C90EB

:101BBB000000121B54D2AF90018AE06011900 0001C
:101BCB00120F4BEB600690000012173B80E90207EA
:011BDB004EBB
:102703004B705F310054696 35F310054645F3100B3
:102713004B705F320054696 35F320054645F320070
:102723005263005273700052 74004B700054696 31B
:102733000054640069307600693031623100693009
:102743003 0316 23200693031623300693032 62310004
:102753006 9303262320069 30326 2330073007200D2
:102763002575 0A00650 0257 50A00630 02100210014
:052773007175 6974009E
:0126B10061F7
:101BDC00C0E0C0D0C083C0829 00B2DE06005448073
:101BEC00F0B005EAF0A3EBF0D082D083D0D0D0E027
:011BFC0022 C6
:101BFD00C0E0C0D0C083C082309 908900E4D74FFF4
:101C0D00F0C299309828 900E50E0B4FF0B7A017B0A
:101C1D00001121BDCC298B01 604F0900E4EE0C0E05D
:101C2D0004F0300000 0082E59 9547FF0C298D082E4
:071C3D00D0B3D0D0D0E032CB
:102C0B00C0E0C0D0C0F0C083C082C00FC00EC00DEA
:102C1B00C00CC00BC00AC009C008C077C076D2D3A5
:102C2B00C2D4900E4CE0F576900E4BE0F577B400E5
:102C3B0005122CB48023B40105122D10801BB40295
:102C4B0005122D7B8013B40305122E1F800BB57656
:102C5B0008122E27757700B0020577E577900E4BCB
:102C6B00F0D076D077D008D009D00AD00BD00CD0CA
:102C7B000DD00EDD00FD082D083D0F0D0D0D0E03298
:101C4400C0D0C0E0C083C08275D018900E3AE04482
:101C540040F0900E51E06005146007801D900E5313
:101C64008003900E597C00EDF0A3A3EEF0A3A3EF44
:101C7400F0EC70D7900E51E004F0D082D083D0E025
:031C8400D0D0328B
:101C8700C0D075D018DF03DE011D0CD0D032323240
:1027D000C07FC0E0C0D0D2D3C2D4757F10E8B50CA2
:1027E00006E9B50D02802A4028D2D57A007B00C3C5
:1027F00012281C12282E400CE8B50C06E9B50D0273
:102800008 0025008C3ED99FDEC9BFC0BD57FE08069
:10281000047AFF7BFFD0D0D0E0D07F2230D508EB08
:1028200033FBEA33FA8006EA13FAEB13FB2230D5C6
:102830000EEF33FFEE33FEED33FDEC33FC800CEC9A
:1028400013FCED13FDEE13FEEF13FF22C0D0C0E02A
:10285000C0F0D2D3C2D47E007D007C0089F0EBA40E
:10286000FFAEF08BF0EBA43EFEE5F03DFD89F0EA16
:10287000A43EFEE5F03DFD50010C88F0EAA43DFCC
:102880 00E5F03CFCD0F0D0E0D0D022400530D5239C
:1028900080 0920D51ECBC5F0CAC5F0C3C2D59BC5E3
:1028A000F09AC5F05020F4C5F0F4C5F00470170597
:1028B000F08013C33BC5F03AC5F04006A2D5C2D59F
:072BC0008004A2D5D2D5224D
:1028C700C020C021C022C07EC07FC07CC07DC07A2E
:1028D700C07BC07BC079C0E0C0D0C0F0C083C082E0
:1028E700D2D3C2D4900E3BE0F520900E3BE0F5220B
:1028F70020170520 16028007E4C5F0E4022AD090CD
:102907000E17E0FAA3E0FB900E15E0F5F0A3E0C286
:10291700D5D312288B85F07AF57B92D5A203920244
:102927 00A2D59203E52023F5200900E38F0900E06ED
:10293700E0F5F0A3E0900E04C5F0F0C5F0A3F09029

```
:102947000E08E0F5F0A3E0900E06C5F0F0C5F0A381
:10295700F0900E0AE0F5F0A3E0900E08C5F0F0C58C
:10296700F0A3F0E57A900E0AF0E57BA3F0900DFE58
:10297700E07012A3E0700E900E0CF0A3F0757E00CD
:10298700757F008047AA7AAB7B900E0CE0F5F0A329
:10299700E0A20492D5A203122BBB9203AAF0FB307F
:1029A700D5047AFF7BFF900E0CEAF0A3EBF0900DB5
:1029B700FCE0F9A3E0F9122B4C900DFEE0F8A3E044
:1029C700F91227D08A7E9B7FA203920F900E00E028
:1029D700700DA3E0700975F000E4C20E022A819021
:1029E7000E04E0FAA3E0FBB57AF0E57BA20792D517
:1029F700B2D5A20412288B920DA8F0F920D51DAAF2
:102A0700F0FBD2D5C312281C4012A20D92D5B8F034
:102A1700E312288B85F078F57930D50685FF78851A
:102A2700FF79900E06E0FAA3E0FB900E08E0F5F0C0
:102A3700A3E0A20692D5B2D5A205122BBB920C303C
:102A4700D50575F0FF74FFA20D92D5A20CAA78AB3D
:102A57007912288B320E20D51CA8F0F9900E00E071
:102A6700F5F0A3E0AAF0FB12284CBC0008BD000556
:102A77008EF0EF800575F0FF74FFAA7AAB7BA20496
:102A870092D5A20E12288B920B20D519A8F0F99097
:102A97000DFCE0FAA3E0FB12284CBC0008BD0005C2
:102AA7008EF0EF800575F0FF74FFA20F92D5AA7E16
:102AB700AB7FA20B12288B400520D50B800B75F041
:102AC70000E4800575F0FF74FFC5F0900E10F0C5A7
:102AD700F0A3F0E5F0902B0B33900E12F0E5209009
:102AE7000E3BF0D0B2D0B3D0F0D0D0D0E0D079D0DB
:102AF70078D07BD07AD07DD07CD07FD07ED022D0CA
:042B070021D0202297
:102B0B00FFE9E4E0DDDAD7D5D3D1D0CECDCBCAC83F
:102B1B00C7C6C5C4C3C1C0BFBEBDBDBCBBBAB9BBB7
:102B2B00B7B6B6B5B4B3B2B2B1B0AFAFAEADADAC84
:102B3B00ABABAAA9A9A8A7A7A6A5A5A4A4A3A2A223
:102B4B00A1A1A09F9F9E9E9D9C9C9B9B9A9A9999AD
:102B5B0098979796969595949493939292919092B
:102B6B008F8F8E8E8D8D8C8C8B8B8A8A89898888A2
:102B7B008787868685858484838382828181B08012
:102B8B007F7F7E7E7D7D7C7C7B7B7A7A7979787B82
:102B9B00777777676757574747373727271717070F2
:102BAB006F6F6E6D6D6C6C6B6B6A6A696968686879
:102BBB00666665656464636362616160605F5E5EE7
:102BCB005D5D5C5B5B5A5A59585857565655545471
:102BDB005352525150504F4E4D4C4B4A49484810
:102BEB004746454443424241403F3E3C3B3A3938DD
:102BFB0037353433231F2E2C2A2825221F1B160055
:102CB400C023D2D3C2D4900E3CE0F523122C8B90C7
:102CC4000E41EAF0A3EBF0900E12E090C004F0C2C3
:102CD4001AD219C218E52390C000F0122C8BEA9086
:102CE4000E49F0A3EBF0C219D218E52390C000F00E
:102CF400122C8BEA900E47F0EBA3F0D21CC21BE51A
:102D04002390C000F0900E3CF0D02322C022C023B8
:102D1400D2D3C2D4900E3BE0F522900E3CE0F523D2
:102D2400122C8BEA900E45F0EBA3F0D21AC219C212
:102D340018E52390C000F0122C8BEA900E43F0EBC0
:102D4400A3F0C21CD21BD21AC219D218E52390C018
:102D540000F0C216900E49E0B40007A3E0B40002EC
:102D640080025002D216E523900E3CF0E522900E2C
:102D74003BF0D0023D02222C022D2D3C2D4900E3B27
:102DB400E0F522C216900E43E0FAA3E0FB900E4158
:102D9400E0F5F0A3E0C39BC5F09A500775F000740A
:102DA40000D216900E3DF0C5F0A3F0900E47E0FA65
:102DB400A3E0FB900E45E0F5F0A3E0C39BC5F09AB9
:102DC400500775F00007400D216900E3FF0C5F0A3C2
:102DD400F020162C900E3DE0F8A3E0F9900E19E0D7
:102DE400FAA3E0FB12284C900E3FE0F8A3E0F9129E
:102DF40027D0BA0007BB0004D21680044002800426
:102E04007AFF7BFFEA900E15F0EBA3F07401900EAD
:102E14003AF0900E3BE522F0D02222D2D3C2D41253
:102E240028C722C024D2D3C2D4900E16E0C32440B3
:102E340090C007F0900E39E0F524302712900E1B55
:102E4400E0F5F0A3E0C5F0900E2BF0C5F0A3F03050
:102E54002612900E1DE0F5F0A3E0C5F0900E2DF0C3
:102E6400C5F0A3F0302512900E1FE0F5F0A3E0C5E5
:102E7400F0900E2FF0C5F0A3F0302412900E21E054
:102E8400F5F0A3E0C5F0900E31F0C5F0A3F03023C7
:102E940012900E23E0F5F0A3E0C5F0900E33F0C5D8
:102EA400F0A3F03022129000E25E0F5F0A3E0C5F077
:102EB400900E35F0C5F0A3F03021129000E27E0F506
:102EC400F0A3E0C5F0900E13F0C5F0A3F03020128B
:102ED400900E29E0F5F0A3E0C5F0900E17F0C5F0D0
:102EE400A3F0900FEE0F9A3E0FA900E13E0F5F0E4
:102EF400900E15E0B5F00F900E14E0F5F0900E165C
:102F0400E0B5F002803A5038900E2BE0F5F0A3E0E3
:102F1400900DFDF0E5F0900DFCF0900E2DE0F5F035
:102F2400A3E0900DFFF0E5F0900DFEF0900E2FE081
:102F3400F5F0A3E0900E01F0E5F0900E00F0B0367D
:102F4400900E31E0F5F0A3E0900DFDF0E5F0900D6A
:102F5400FCF0900E33E0F5F0A3E0900DFFF0E5F007
:102F6400900DFEF0900E35E0F5F0A3E0900E01F028
:102F7400E5F0900E00F0900DFEE0B50909900DFF0C
:102F8400E0B50A028007E4900E0CF0A3F0E4900E82
:052F940039F0D02422F9
:102C8B00074807A01D5E0FD74FFC291D5E0FD30C050
:102C9B0003F090C007E0540870F890C001E0F4FA1C
:092CAB0090C000E0F4FBD291227C
:03000000020100FA
:1001000007S8130C2D3C2D412066B7E0D7FFC900085
:0401100000021B8747
:102682000020202020202020202020282828282040
:102692000202020202020202020202020202020038
:1026A2000208810101010101010101010101010A0
:1026B20010040404040404040404401010101090
:1026C200010104141414141410101010101010155A
:1026D200010101010101010101010110101010A0C
:1026E200010104242424242420202020202020222C
:1026F200020202020202020202021010101080
:0127020020B6
:101C9700074027800790412070A1204A704008AB3E1
:101CA7008B82E0FB8B051204A706008A838B82E0F8
:101CB700FB120246602B1204A704008A838B82E082
:101CC70070077B007A0002074E74042FFBE43EFA8C
:101CD700012037B0274062FFBE43EFA12037B02B099
:101CE700B81204A704008A838B82E0FBEB33E495E8
:101CF700E0FABB05BA041204A706008A838B82E028
:0D1D0700FBEB33E495E0FA12053902074EBC
:101D140007401780079041207A1204A10400120461
```

:101D2400A7050012037B0212045002074E740278C6
:101D340000790812070A740A2FFDE43EFC7B027A3C
:101D440000120531120504040074042FFBE43EFA6A
:101D540012077A740A2FFBE43EFA12077A7B147A8C
:101D64001D12077A1204A71000090000B121D8A128F
:101D7400005040600$7D001204A70800120450120492
:06D8400A7060002074E55
:101D8A0074027800798AA12070A7B007A0012050405
:101D9A00110074AA2FFBE43EFA12037B028A83B9A
:101DAA0082E0FB1204FE04008B057B2512025560BB
:101DBA003C12049B0400700B1204A71100020B74EBB
:101DCA001204A7AE0012077A12049B06008B0512B2
:101DDA0004A7AE00C003C002BD039000031207627D
:101DEA0074112FFBE43EFA12037B0280A51204A7AA
:101DFA00AA008AB38B82E0FBBB057B251202466050
:101E0A003674AA2FFBE43EFA12037B021204A7AE31
:101E1A000012077A7B25BB051204A7AE00C003C007
:101E2A0028D039000031207627A4112FFBE43EFA3D
:101E3A0012037B02021D9C7B001204FE13007B002E
:101E4A001204FE14001204A7AA008A838B82E0FB04
:101E5A008B057B2B12024670141204A7AA00BA83F0
:101E6A008B82E0FBBB057B20120246601874AA2F36
:101E7A00FBBE43EFA12037B028AB3BB82E0FB1204A4
:101E8A00FE1300802E1204A7AA008A838B82E0FB2D
:101E9A008B057B2D120246601874142FFBE43EFA60
:101EAA0012037B0174AA2FFBE43EFA12037B028021
:101EBA0002B002B0901204A7AA008A838BB2E0FB2B
:101ECA008B057B3012024660147B011204FE23004C
:101EDA0074AA2FFBE43EFA12037B02B0077B0012EE
:101EEA0004FE23001204A7AA008A838B82E0FB8BDC
:101EFA00057B2A12024660531204A7B000120356469
:101F0A0000028A83BB82E0FAA3E0FB1205040F0029
:101F1A001204AB0F007B007A0012201E26020120467
:101F2A00A70F0012055712050400F0012049B140094
:101F3A00EB600274FF04FB7A001204FE140074AA18
:101F4A002FFBE43EFA12037B02806F7B007A0012B9
:101F5A0005040F001204A7AA00BAB3BB82E0FB8B78
:101F6A00057B30120229606521204A7AA008A838BC9
:101F7A00B2E0FBBB057B39120236603E1204AB0FFE
:101F8A0007B0A7A001205428B058A0474AA2FFB89
:101F9A00E43EFA12037B02BAB3BB82E0FB7A00120B
:101FAA00078 18B058A047BD07AFF120531120796C6
:101FBA001205311205040F00B09A1204A7AA00BA9A
:101FCA00838B82E0FB8B057B2E1202467003022074
:101FDA008B74AA2FFBE43EFA1202E3028AB3BB82F5
:101FEA00E0FB8B057B2A12024660251204A7B000BB
:101FFA00120356002BAB3BB82E0FAA3E0FB1205E1
:10200A0004050074AA2FFBE43EFA12037B02806FD8
:10201A007B007A001205040500120A7AA008AB32D
:10202A008BB2E0FB8B057B3012022960521204A7D7
:10203A00AA00BAB3BB82E0FBB057B391202366009
:10204A003E1204AB05007B0A7A001205428B058A10
:10205A000474AA2FFBE43EFA12037B02BAB3BB826C
:10206A00E0FB7A001207818B058A047BD07AFF1283
:10207A000053112079612053112050405000809AB06F
:10208A00097BFF7AFF12050405001204A7AA008A39
:10209A00838B2E0FBBB057B6C120246601667B0108
:1020AA007A00120504070074AA2FFBE43EFA120311
:1020BA007B0280097B007A00120504070074AA2FAC
:1020CA00FBE43EFA12037B028AB38B82E0FB120452
:1020DA00FE040012064524EF0024C64521DC5821DF
:1020EA00B6323496424C66524BF6623496921DC3E
:1020FA006F21DC70214973234975211DC78000024A3
:10210A00FA1204A7B000120356000028A838B82E0F7
:10211A00FAA3E0FB1204FE240074242FFBE43EFA27
:10212A0012050410001205041F0012049B240060FE
:10213A000B741F2FFBE43EFA12037B0202225181 2CE
:10214A0004A7B00012035600028A838B82E0FAA326
:10215A00E0FB120504100070097BA47A0B1205042A
:10216A001D001204AB05007B007A001201E260092F
:10217A007B107A27120504050007B007A001 20504F9
:10218A000D00741D2FFBE43EFA12037B028AB38B37
:10219A0082E0601C1204AB0D001204A705001201B4
:1021AA00E2600D740D2FFBE43EFA12037B0280D22B
:1021BA00741D2FFBE43EFA1202E90212050410005
:1021CA001204AB0D00741D2FFBE43EFA12011D022E
:1021DA0025181204A104007B701202466022120420
:1021EA00A7B0001203560028AB3BB82E0FAA3E0AA
:1021FA00FBB8B058A047B007A0012050815008003FD4
:10220A001204A7070060181204A7B000120356000B0
:10221A00048A838B821204DA120501500802012C0
:10222A0004A7B00012035600028A83BB82E0FAA345
:10223A00E0FB8B058A047B007A00120508150074FE
:10224A00A92FFBE43EFA1205041D001205041F0023
:10225A007BB37A0B120504210012104007B6FE0
:10226A0012024660147B077A00120050409007B03F8
:10227A007A001205040B00080271204A104007B785F
:1022BA0012024660097BC47A0B12050421007B0FF7
:10229A007A0012050403007B047A001205040B0077
:1022AA001204A7210012077A1204B11700BD038CB9
:1022BA0002120796120781 8B058A041204A70B00E3
:1022CA001204401207961205318AB38B82E0FBBB37
:1022DA00057 41D2FFBE43EFA1202E902120450 12A1
:1022EA0004AB0B0074152FFBE43EFA1012F70B0F9
:1022FA001204AB05007B007A001201E26011120049D
:10230A0009B2300600A1204A70F001205040500129D
:10231A0004AB1F001204A710001205398B058A049D
:10232A001204A705001201E260127D30741D2FFB12
:10233A00E43EFA1202E90212045080D3022518126E
:10234A0004A70700601B1204A7B0001203560004 7D
:10235A008A838B821204DA120508190080004C12044F
:10236A00A7B000120356000280838BB2E0FAA3E028
:10237A00FB120504D0001204A104007B751204623B
:10238A0060141204A70D008B058A047B007A0012E0
:10239A00005081900080141204A70D00EAFC33E4951D
:1023AA000E08B058FBFA12050B19001204A104007B50
:1023BA007512025560181204B11900120788EE4FD5B
:1023CA00FCFBFA12026460067B017A00B0047B003F
:1023DA007A0012050401D006016 7B2D1204FE13000C
:1023EA001204B1190012054F12050815 00B01C125B
:1023FA004B1300EB60027401FB7A001205040DC2
:10240A000012048119001205081500074A92FFBE483
:10241A003EFA12050410012050F41F001204B1152C
:10242A000012078B7D00A7C007B007A00120595BDD0
:10243A00038B057B30EB2DFB8B05741D2FFBE43ED4
:10244A00FA1202E90212045D07D0A7C007B007A002B

```
:10245A0012078B74192FFBE43EFA12012670BD12B6
:10246A0004AB05007B007A001201E2601912049B9A
:10247A00230060121204AB0F001204A70D0012050C
:10248A003912050405001204AB1F001204A71D002F
:10249A001205399B058A041204A705001201E260AD
:1024AA00127D30741D2FFBE43EFA1202E902120477
:1024BA005080D380597B001204FE04007BD57A0B2E
:1024CA001205041D001205041F001204A71F008A2A
:1024DA00B38B82E0600D741F2FFBE43EFA12037BAC
:1024EA000280E7802974AA2FFBE43EFA120391020D4
:1024FA007BF87A0B1205041D001205041F007D04E7
:10250A007C00741F2FFBE43EFA12011480001204AF
:10251A00AB1F001204A71D00120539120504070098
:10252A008B058A041204A70F001201AC600B7B0012
:10253A007A001205040D008026121204AB0F001204 63
:10254A00A707001205398B058A0412049B1300EBB6
:10255A0060027401FB7A00120539120504000012998
:10256A00049B14007042740D2FFBE43EFA1202E938
:10257A00028B058A047B007A001202116602A120477
:10258A00A7AE0012077A7B208B051204A7AE00C003
:10259A0003C0028D039000031207627411 2FFBE43B
:1025AA003EFA1203 7B0280BE12049B13006020B12B8
:1025BA0004A7AE0012077A12049B15008B051204B9
:1025CA00A7AE00C003C0028D0390000312076274 15
:1025DA00112FFBE43EFA12037B0274072FFBE43E41
:1025EA00FA1202E9028B058A047B007A00120 21180
:1025FA0060391204A7AE0012077A741F2FFBE43E5B
:10260A00FA12037B028A838B82E0FB8B051204A7F2
:10261A00AE00C003C0028D0390000312076 2741 5A
:10262A002FFBE43EFA12037B0280AF12049B1400D4
:10263A006042740D2FFBE43EFA1202E9028B05BA0E
:10264A00047B007A00120211602A1204A7AE00 125B
:10265A0077A7B208B051204A7AE00C0028D47
:10266A003900003120762741 2FFBE43EFA12036F
:07267A007B02B0BE021D9CE3
:10277800286E756C6C20706F696E746572 2290030F4
:102788003132333435363738394142434445 4600CF
:102798003031323334353637383961626364 6566CF
:1027AB0000464C4F4154533F2077726F6E6720646
:1027BB006F726D617474657220696E 74 616C 6C 8C
:0827CB00656421003F3F3F 00 62
:03011400120 13D120531020155F2
:09011D0012013D120539020155E1
:090126000120163120578020 18D3B
:0E012F00120788120163BD0312041802018D5D
:10013D00D000D001C002C003C001C0008B828A83F1
:08014D00E0CCFAA3E0CDFB2297
:0E015500D082D083F5F0EAF0A3EBF0E5F022C3
:10016300D000D001C002C003C001C0008B82BA83CB
:10017300078027904E0F6A308D9FA8F828E83780295
:0A018300 7904E0C6F0A308D9F922C0
:10018D00D082D083F5F078027904E6F0A308D9FA8D
:03019D00E5F022 68
:1001A000EB33E495E0FAED33E495E0FCEC33EA6CF4
:1001B00013C0E0120539D0F0600C30F602AAF0EA64
:0701C00033B3E4FA33FB2224
:0F01C7007A007C001205396005B3E4FA33FB229D
:1001D600EB33E495E0FAED33E495E0FCEC33EA6CBE
:1001E60013C0E0120539D0E030E601FAE4CA235420
:0301F60001FB22E8
:0C01F9007A007C001205E39E4FA33FB2286
:10020500EB33E495E0FAED33E495E0FCEC33EA6C8E
:10021500 13C0E0120539D0E030E601FAE4CAF42350
:040225005401FB2263
:0D0229007A007C001205E39E4FAB333FB22A1
:10023600 7A007C001205390B6004E4FA33FBEB22EA
:0F0246007A007C001205390B6003E4FAFBEB220F
:0F0255007A007C0012053960 04E4FA04FBEB2206
:10026400 8E838F82E033E06A13C0E0120560D0E031
:0B02740030E601FAE4CA235401FB222B
:10027F00D083D082E493F5F0A3E493A3C082C0832C
:10028F00B8030AC004C005C00078048008C002C0CB
:10029F0003C00078 02A6F008F6120542D000B8039A
:0F02AF0005D005D00422B058A04D003D002228B
:1002BE00D083D08212034D800ED083D0821 2034D94
:1002CE00C3E499F9E49BF8C082C0838A838B82C014
:1002DE0082C0838028780 07901800478FF79FFD06E
:1002EE00D083D082E493A3C082C0838A838B82B 401BD
:1002FE005E029FBF022C082C083 B40213E0FAA30A
:10030E00E029FBEA38FAD083D082F0A3EBF04A2240
:10031E0075F004C00007802E0F608A3D5F0F929FDC7
:10032E00D000EC38FCEB38FBEA38FAD083D082757B
:10033E00F0047802E6F0A308D5F0F94C4B4A22E41B
:10034E0093F8A3E493F9A322D083D08212034D80B5
:10035E000ED083D08212034DC3E499F9E49BF8C00D
:10036E0082C0838AB38B82C082C0838 02A78079B0
:10037E0001 800478FF79FFD083D082E493A3C082FA
:10038E00C0838AB38B82B40107E029F0C399FB22D4
:10039E00C082C083B40219E0FAA3E029FBEA38FA5E
:1003AE00D083D082F0A3EBF0C399FBEA98FA4B22EC
:1003BE0075F004C00007802E0F608A3D5F0F929FD27
:1003CE00D000EC38FCEB38FBEA38FAD083D08275DB
:1003DE00F004C00007802E6F0A308D5F0F9D000C30F
:0F03EE0099FDEC98FCEB98FBEA98FA4B4C4D22EA
:1003FD00EB601124F05004E4FAFB22EDC333FDEC65
:0B040D0033FCDBF78C028D03EA4B226E
:10041800C00312079DD082E582601824E05006E4EC
:10042800FAFBFCFD2278047902C3E713F709D8FA2E
:08043800D582F2EA4B4C4D2283
:08044000EA5CFAEB5DFB4A22C5
:08044800EA4CFAEB4DFB4A22DD
:100450008A83BB82EDF0FB22BA838B82ECF0FAA3F5
:10046000EDF0FB4A22C003C00212079DD083D08268
:0E04700078047902E7F009A3D8FA4C4B4A222F
:10047E0078037901800087902800279047802D083AA
:10048E00D082E4932BF5F0A3E4933A802778037996
:10049E00018 01478057901800E7902800878047930
:1004AE0002800479047802D083D082E4932FF5F091
:1004BE00A3E4933EA3C082C083F5B3B5F08275F0DA
:0C04CE0000E0F642F008A3D9F8E5F022A7
:1004DA0075F00078047902E0F745F0F5F009A3D841
:1004EA00F62275F0007904 7802E6F045F0F5F00896 96
:0404FA00A3D9F6226A
:1004FE00780379018008790 28002790 47802D0832A
:10050E00D082E4932FF5F0A3E4933EA3C082C083B0
:10051E00F58385F08275F000E6F0A30842F0D9F875
```

:03052E00E5F022D3
:08053100EB2DFBEA3CFA4B2222
:09053900EDC39BFBEC9AFA4B22B6
:10054200EB8CF0A4CA8DF0A42AFAEB8DF0A4FBE5A3
:05055200F02AFA4B2223
:09055700E4C39BFBE49AFA4B2279
:10056000BE83BFB27804E0C0E0A3D8FAC378047940
:0B0570005D0E097F719D8F90207CA80
:10057B001206151205B9BC007905E6F71819B901A1
:0A058B00F9E58124F4F5810207CAA6
:10059500120615 1205B9BB007905E6F71819B9018B
:0A05A500F9E58124F4F5810207CA8C
:0A05AF00780512060BEA4B4C4D22B2
:1005B9008D0079 04B6000418D9FA227A208C0079C2
:1005C90008C3E633F61BD9FA8E83BF828B008D0122
:1005D3008AF07A04C3E697F01819A3DAF8AAF0406A
:1005E9001EBE83BF28B007904E0F6A318D9FABCCA
:1005F90000E62401F6187903E63400F618D9F9DA89
:02060900BC2211
:0A060B00C37904E496F618D9FA2228
:10061500D0F0D001E4C0E0C0E0C0E0C0EB38F40
:10062500827804E0C0E0A3D8FAC002C003C004C0C9
:100635005AD81E58124FCFC24FCFBC001C0F02252
:10064500D083D082E4337 0097 401937004A3A380CE
:100655 00B7402936B6005A3A3A3B0E8740193C09B
:06066500E0E493C0E02276
:10066B00900B2FAAB3AB8 29001B2120 6C6902703B0
:10067B00AA83AB8 29027 031206D1602CC002C00361
:1006BB00C082C083782 0 7904E493F6A308D9F9BB6
:1006930 0828A838C028D0312 06C6D083D082D00 34C
:1006AB00D002A3A3A3A380CF1 20 6DA 27 03 26B101CE
:1006BB00001206DA27D027030B2F22120 6D1700166
:1006CB0022E4F0A380F5EB658270 03EA658322D008
:1006DB0083D0827 8 0790 6E493F6A308D9F9C08215
:1006EB00C083D828CB31206D16013E493A3ADB2F9
:0F06FB00AC838F28E83F0A3AF82AE8380E42224
:10070A006019C000C001C083C082F854012402F9F4
:10071A001207A4D082D083D001D000EF2582FDEE4B
:10072A0035B3FCC3EF9F5B2FFEE98FEF583D0027C
:10073A00D003D0EF0FA3D0EF0A3ECF0A3EDF0C03A
:10074A0003C00222BEB38FB2E0F5F0A3E0C0E0C0EE
:10075A00F0A3E0FEA3E0FF22D001D000D0E0D0F069
:09076A00C000C001C0F0C0E02293
:07077300780179050207A4DB
:07077A00780279020207A4D6
:07078100780279040207A4CD
:07078800780479020207A4C6
:07078F00780179050207B7AC
:07079600780279040207B7A5
:07079D00780479020207B79E
:1007A400EFC398FFEE9400FE8F828E83E7F0A309D7
:0307B400D8FA224E
:1007B700C0E08F828E83E0F7A309D8FAAE83AF82B9
:0307C700D0E0225D
:1007CA0092F0EF2404FFEE3400FEA2F0ED4C4B4A07
:0107DA0022FC
:00000001FF

:100AAC00E4780079041209D47B00900007EBF07B0A
:100ABC0000090008EBF07B07A00900020EAF0EB4D
:100ACC00A3F07B007A00900022EAF0EBA3F07B000D
:100ADC007A00900024EAF0EBA3F07B637A0090009C
:100AEC0026EAF0EBA3F07B0090003FEBF07B12903A
:100AFC000045EBF07B00900046EBF07B019000474B
:100B0C00EBF0020A18E4780079041209D47DA07C79
:100B1C00477B047A00900000B1206DF7DEC7C467B51
:100B2C00047A0090000F1206DF7D687C487B047A03
:100B3C0000009000131206DF7DE07C937B047A00901A
:100B4C0000001711206DF7D107C467B047A0090001B98
:100B5C001206DF7B0090000AEBF0190009EBA2
:100B6C00F0020A18740178 0079041209D47B009001
:100B7C000007EBF012068E0400900008EBF07B01EE
:100B8C00900045EBF07B00900046EBF07B01900071
:100B9C0047EBF07B0090000AEBF0020A18E47800B7
:100BAC0079041209D4900000012 0B11900000120A63
:100BBC00AC9000001212889000001213079 00000F5
:100BCC00120C07900000123 69F900000123DCF903F
:100BDC00000001211C5900000123B1E900000124341
:100BEC009F7B477A001 20A4B7B467A00120A4B7B9A
:0B0BFC00457A00900006121C3B80D4DC
:100C0700E4780079041209D47B107A279003E9EA83
:100C1700F0EBA3F07B0090001FEBF07B0090C005BA
:100C2700EBF07B128B89D2A9D2AFD288D28A020A83
:100C370018740178 0079 0612 09D41 20 68E0600127C
:100C470090F0C59000CA8010CA8020CA8030000FE
:100C5700CBB1206A407 00120A597D007C007BB09A
:100C67 007A401201A9120A597D007C007BC07A0A4
:100C7700 1201A9120A597D007C007B007A4112 01FA
:100C8700A91202498D038C021206F704007B027A2F
:100C9700008B058A0474042FFBE43EFA12012680BB
:100CA700131206A407001202498D038C021206F7DD
:100CB7000040 0B000120 69A0400020A18740178 00E2
:100CC700790E1209D412 06 8E0E0012090F0CE400D9
:100CD7000D0F010D59020D9303 00000DCD7B0A1264
:100CE7006F104 007B011 206F105007BC81206F12C
:100CF7008007B011206F107007B501206F109007C
:100D07007BC81206F10A007B0112 06F10D007B6415
:100D17001206F10C00020DCD7BFF1206F104007BD9
:100D2700FF1206F10500 7BFF1206F108007BFF1298
:100D370006F107007B781206F109007B641206F1C1
:100D4700A007B1411206F10D007B0F1206F10C004E
:100D5700B0747BFF1206F10400 7BFF1206F1050089
:100D67007BFF1206F108007BFF1206F107007B46A6
:100D7700 1206F109007B641206F10A007B0A1206CB
:100D8700F10D007B1411206F10C00803A7B461206 27
:100D9700F104007B641206F105007B011206F108DD
:100DA7007B041206F107007B281206F109007B7D
:100DB700CB1206F10A007B0A1206F10D007B6412C5
:100DC7006F10C00800012068E04001206F10600E0
:100DD70012068E09001206F10B00120 68E0400BB14
:100DE7007F12068E05008B7E12068E06008B7D1203
:100DF70068E07008B7B1206 8E08008B7C12068EF0
:100E070009008B7A12068E0A008B7912 068E0B006B
:100E17008B7B12068E0C008B7612068E0D008B7760

```
:100E2700020A1874017800790412090D47BF88B053B
:100E37007B1F7A008A838B82E05DF0FB12068E04AB
:100E47000012090F0E5B000EC2010F14020F66039A
:100E570000000FE1900024E0FAA3E0FB8B058A0471
:100E670012069A060012064B7B0A7A008B058A0443
:100E770012069A080012064B7B008B057B1F7A002F
:100E87008A838B82E04DF0FB90001FE0FBBB0512FD
:100E9700069A0A0012064312068E0500700E7B00A2
:100EA7008B0512069A0C0012064380007B208B05DB
:100EB70012069A0C0012064302 0FE1900022E0FA94
:100EC700A3E0FBBB058A0412069A060012064B7BE9
:100ED7000A7A008B058A0412069A080012064B7BD1
:100EE700028B057B1F7A008A838B82E04DF0FB9093
:100EF70001FE0FB8B0512069A0A001206437B00CF
:100F07008B0512069A0C0012064302 0FE1900208F
:100F1700E0FAA3E0FB8B058A0412069A060012068A
:100F27004B7B0A7A008B058A0412069A080012 06B0
:100F37004B7B018B057B1F7A008A838B82E04DF008
:100F4700FB90001FE0FBBB0512069A0A001206436E
:100F57007B008B0512069A0C0012064302 0FE190E4
:100F67000026E0FAA3E0FB8B058A0412069A06002B
:100F770012064B7B647A008B058A0412069A0800D6
:100F870012064B7B048B057B1F7A008A838B82E0DA
:100F97004DF0FB90001FE0FB8B0512069A0A00122A
:100FA70006439000 45E0FB8B057B121203E3700EAE
:100FB700900045E0FB8B057B011203E3600E7B0A83
:100FC7008B0512069A0C0012064380007B0B8B05D2
:100FD70012069A0C0012064380000 20A18E47800F1
:100FE7007904120947B06B8BC7B06B8BAD28C0200
:100FF7000A1874017800790412090D47B009003E879
:10100700EBF07B0009003E7EBF01206A4050 0120A51
:1010170 05912068E0800900005120C389003EBEA6F
:10102700F0EBA3F012068E0C009003EFEBF0120624
:101037008E0B009003EEEBF07BEF8B057BE67A03DC
:101047008AB8BB82E05DF0FB7BF78B057BE67A0377
:101057008A838B82E05DF0FB7BFB8B057BE67A0363
:101067008A838B82E05DF0FB12068E0C0060127B9B
:1010770001B057BE67A038A838B82E04DF0FB804B
:10108700107BFE8B057BE67A038AB38B82E05DF01B
:10109700FB12069A09008B058A047B017A0012036A
:1010A700E7602C7BBF8B057B1F7A008A838B82E0EE
:1010B7005DF0FB90001FE0FB90C005EBF07BFD8B24
:1010C700057BE67A038A838B82E05DF0FBB02A7BCF
:1010D700 408B057B1F7A008A838B82E04DF0FB9063
:1010E70001FE0FB90C005EBF07B028B057BE67AE7
:1010F700038A838B82E04DF0FB12068E040090007A
:101107000 01120CC37BED7A03120A4B7B057AC012DE
:1011170 0A4B7BF07A03120A4B7BE97A03120A4BDC
:101127001206BE1400120A3D12068E0D009000 0A58
:10113700120E2A7B0190003FEBF0900000120FE4A3
:10114700020A18E47800790512090D490C004E0FB7C
:101157001206F10400C28BD2AA9003EEE0FB90C006
:101167 0007EBF07B80BB057B1F7A008AB38B82E0FD
:101177004DF0FB90001FE0FB90C005EBF0900000E6
:10118700 00120FE4020A18E4780079041209D47B00EC
:1011970 0090C007EBF07B7F8B057B1F7A008AB38BE0
:1011A70082E05DF0FB90001FE0FB90C005EBF09044
:1011B70000000121288900001213070 20A18E47840
```

```
:1011C70000079041209D47B0090C000EBF0020A18E2
:1011D7007404780079081209D41206A408001206CC
:1011E700FB04007B007A00020A1874017800790476
:1011F7001209D49003E6E0FBBB057B10EB5D7007CB
:101207007B007A00020A1812068E0400120 90F12D8
:101217004A001238011 22602125C03000012819064
:1012270003E9E0FAA3E0FB900020EAF0EBA3F080EB
:1012370049 9003E9E0FAA3E0FB900022EAF0EBA370
:10124700F080379003E9E0FAA3E0FB900024EAF08E
:10125700EBA3F0802590C007E0FB8B057B02EB5DDD
:10126700600E7B007A00900026EAF0EBA3F080087E
:101277007B267A001205530280007B017A00020A5E
:10128700018E4780079041209D47BD78B057B1F7A81
:10129700008A838B82E05DF0FB90001FE0FB90C02B
:1012A70005EBF0020A18E47800790412090D47B28C8
:1012B7008B057B1F7A008A838B82E04DF0FB9000C1
:1012C7001FE0FB90C005EBF0020A18E4780079 04F0
:1012D7001209D47BF78B057B1F7A008A838B82E008
:1012E7005DF0FB7B208B057B1F7A008A838B82E076
:1012F7004DF0FB90001FE0FB90C005EBF0020A18D1
:10130700E47800790412090D47BDF8B057B1F7A0010
:101317008A838B82E05DF0FB90001FE0FB90C005A5
:10132700EBF0020A18E4780079061209D47B00 90E2
:10133700C004EBF07B007A001206F7040012 069A4D
:101347000 04008B058A047B0A7A00120 38B60 0D74F4
:1013570 0042FFBE43EFA12055302 80E17B0 0030972D
:1013670001 0B7A00020A18E4780079041209D49074
:1013770003E6E0FB8B057B04EB5D60077B017A00EE
:10138700020A187B007A00020A18740278007904AE
:101397001209D4C28CC2A8C2AA12069A04008AB370
:1013A7008B82E0FB900 43EBF012069A06008A83DB
:1013B7008B82E0FB900044EBF07B138B0512069ABF
:1013C700004001206437B008B0512069A060 0120 6DC
:1013D700437B018B0512069A0800120643120 68EFC
:1013E7000A00900042EBF0020A1874027800790 4B0
:1013F7001209D412069A0400 8AB38B82 E0FB7A00D2
:10140700 01208CE000001 3001C3014381 43B147F1 44C
:10141700 0971 51B15A4162 116E7177D1 83B189 41 965
:101427 00 21 98B1A141 A98 1B1C1B8D1B8B1BBB1C8B
:101437002E021C3812069A0800120A4B12069A0846
:101447 000 900004121D10EA7 02BC0037 D001 203E8
:10145700F2D0037002B01E7D011203F27017120 68C
:101467009A040012055301 7B008B0512069A0600A9
:101477001206438 000021C3812069A04 0012 055314
:101487 00 017B008B0512069A0600120643021C38E0
:101497 0012 069A 08 00120A4B1206 9A08009 0000 4D6
:1014A700121DDB1208CE000003 001518148B15012E
:1014B70014BD14DF805B7B0212 0A3D12069A09 00F5
:1014C7 00120A4B12 069A0900120A4B12 069A09 00D1
:1014D70 09000007121391803 97B03120A3D12 069A76
:1014E7 00090 0120A4B12 069A09 00120A4B12 069AB1
:1014F7 00 090 09000071213918 017120 69A 04001230
:10150700 0553017B008B0512069A060012064380DD
:10151700 0 0021C3812069A 0 8 00120A4B120 69A 08 93
:1015 27000 09000 04122A18EA707012090F154400 7F
:10153700158A01 15460 215680 4 00 001 5A18 05B7B1A
:101547 00 02120A3D12069A0900120A4B12 069A095C
```

```
:1015570000120A4B12069A0900900007121391B095
:10156700397B04120A3D12069A0900120A4B120629
:101577009A0900120A4B12069A09009000071213E3
:1015870091B01712069A0400120553017B008B0500
:1015970012069A0600120643B000021C3812069AA9
:1015A70008001C20A4B12069A0B00900004122C0237
:1015B700EA7064C0037D001203F2D00370028057C3
:1015C700C0037D051203F2D00370227B05120A3DBA
:1015D70012069A0900120A4B12069A0900120A4BC0
:1015E70012069A090090007121391B02A7D0112B2
:1015F70003F270239000021206CD9000391206DF25
:1016070012069A0400120553017B008B0512069AF5
:10161700006001206438000021C3812069A080012C0
:101627000A4B12069A0800900004122C71EA600314
:101637000216E412090F164D00169400116500216F1
:101647007204000016E40216E47B02120A3D1206039
:101657009A0900120A4B12069A0900120A4B12063F
:101667009A0900900007121391B0727B04120A3DB9
:1016770012069A0900120A4B12069A0900120A4B1F
:1016870012069A0900900007121391B050E4FDFC9E
:101697000FBFA9000291206DFE4FDFCFBFA9000310B
:1016A7001206DF7B00900004EBF07B01900004EEBDE
:1016B700F07B09BB0512069A04001206437B008B08
:1016C7000051206DA06001206437B008B0512069A3E
:1016D700008001206439000001F0FE48000021C3835
:1016E7009000031206CD120A597D0007C537B077A90
:1016F70000120401602278B06120A3D12069A0900B5
:1017070012A4B12069A0900120A4B12069A09008E
:101717009000071213918058900004E0FB8B057BE4
:101727000021203E3604D900031206CD900000412BF
:101737001107EB4A6025C28CC2A87B01900004EB10
:101747007F07B08BB0512069A04001206437B018B77
:10175700005120690A0800120643B00C7B09BB05128E
:1017670000694001206437B008B0512069A0600B0
:1017770001206430021C3812069A0800120A4B120678
:101787009A0800900004122D7CEA600302183812B0
:1017970000090F17A90017F00117AC0217CE0400084
:1017A70001B3802183807B02120A3D12069A090012ED
:1017B7000000A4B12069A0900120A4B12069A09009060
:1017C70000007121391B06A7B04120A3D12069A09D8
:1017D700000120A4B12069A0900120A4B12069A09BE
:1017E70000090000712139180548E4FDFCFBFA90007B
:1017F7000291206DFE4FDFCFBFA90003112060F1226
:1018070069A0400120553017B008B0512069A06FF
:1018170001206437B008B0512069A080012064346
:101827007B01900041EBF0C289D2A89000001120F13
:101837000E4021C3890003112060CD120A597D407C13
:1018470009C7B007A001201406023120690400129E
:101857000553017B008B0512069A0600120A637B8F
:1018670001B80512069A0800120A637B01D90003160
:1018770001206CD120A597DD07C077B007A0012042C
:1018870016007A001206077B01900003EEBF0021C3B9000090D5
:10189700E0603E7B0B7A00BB05BA04900000AE0FB30
:1018A7007A00780312045700041207248A83BB8274
:1018B700120B6CD9000351206DF7B0A7A001204BBB0
:1018C70018B057B05ED8BF084E5F0FB90000AEBBF
:1018D700F07B01900003DEBF07B077A00120553018B6
:1018E7007B0C8B0512069A04001206437B008B05BE
```

```
:101BF70012069A0600120643021C3812069A0B00BE
:1019070012A4B12069A0800900004122E87EA70FA
:101917007012090F192B001971011192D02194F04A3
:101927000000019B8805B7B02120A3D12069A0900A3
:101937012A4B12069A0900120A4B12069A09005C
:10194700900007121391B0397B04120A3D12069A00
:101957000900120A4B12069A0900120A4B12069A3C
:1019670000090900007121391801712069A0400122BB
:10197700555530175B008B0512069A0600120643B069
:10198700000021C3812069A0800120A4B12069A081F
:101997000009000041232958EA707012090F19B40012
:1019A70019FA0119B60219D80400001A11805B7BD5
:1019B700002120A3D12069A0900120A4B12069A09EB
:1019C700000012A4B12069A0900900007121391B021
:1019D700397B04120A3D12069A0900120A4B120685
:1019E7009A0900120A4B12069A09009000071236F
:1019F70091801712069A0400120553017B008B058C
:101A070012069A0600120643B000021C3812069A34
:101A1700080012A4B12069A0800900004122F922F
:101A270012008CE000003001A951A381A7E1A3A1ABD
:101A37005C805B7B02120A3D12069A0900120A4B70
:101A470012069A0900120A4B12069A09009000071B
:101A57001213918397B03120A3D12069A0900126C
:101A67000A4B12069A0900120A4B12069A09009AD
:101A77000000071213918017170269A040012055301EA
:101A87007B008B05120069A06001206438000021C93
:101A970003812069A0800120A4B12069A0B0090009C
:101AA70041224E01208CE000003001B191ABC1B05
:101AB7000021ABE1AE0805B7B02120A3D12069A09DF
:101AC70000012A4B12069A0900120A4B12069A09CB
:101AD7000009000071213918B0397B03120A3D120600A
:101AE7009A0900120A4B12069A0900120A4B1206AB
:101AF7009A0900900007121391B01712069A0400A2
:101B0700120553017B008B0512069A06001206434A45
:101B1700800000021C3812069A0800120A4B12069A15
:101B27000800900004123306EA705C80370D012F3
:101B37000003F2D00370028024BC0037D021203F2D0B0
:101B470000370227B02120A3D12069A0900120A4B01
:101B570012069A0900120A4B12069A090090000070A
:101B67000121391801E7D011203F2701712069A0458
:101B7700000120553017B008B0512069A06001206188
:101B8700043B000021C389000074E0FB8B0590000089B
:101B9700E0FB1203F2600E7B02BB0512069A04002B
:101BA700120643800912069A0400120553010210B
:101BB700038021C3812069A0800120A4B12069A08B5
:101BC700000090000412348EA705BC0037D001203A3
:101BD700F2D00370028024EC0037D021203F2D003DD
:101BE70070227B02120A3D12069A0900120A4B1252
:101BF7000069A0900120A4B12069A09009000071206A
:101C0700013918017D011203F27001A7B008B05125C
:101C17000069A0400120643B78008B0512069A0600FB
:101C27001206438000800A08009000001251D78076
:101C370000002A1874027800790412094120690460
:101C470008008A838B82E0FBC0037D001203F2D0079
:101C570036003021CE970090000028E07F090002949
:101C670012006CD9000311206DF900028E070E712CF
:101C77000069A04008A838B82E0FBC0037D071203068
:101C8700E3D00379077D091203F2701D12069A084C
```

```
:101C970000120A4B12069A0800120A4B12069A08FB
:101CA700009000061213F180379000311206CD1212
:101CB7000A5990002D1206CD12043B6021C28C9068
:101CC700003FE0600D90000012114A7B0090003F3A
:101CD700EBF07B018B0512069A0800120643800081
:101CE70080247D011203F2701D12069A0800120A61
:101CF7004B12069A0800120A4B12069A0800900027
:091D0700061213F18000020A1813
:06507B0000BE00004A3AED
:101D100074027B0079041209D412069A04008A83A6
:101D20008B82E0FBC0037D001203F2D0036003024C
:101D30001DB390C007E0FBBB057B0AEB5DFBBB05B9
:101D40007B0A1203E360137B007A00900026EAF01E
:101D5000EBA3F07B017A00020A187B00B8B0512068CB
:101D60009A06001206437DE87C037B007A00090000F
:101D70002D1206DFE4FDFCFBFA9000291206DF12AB
:101D8000069A0400120553017B1F120A3D7B1F12A5
:101D90000A3D7B017A00120A4B7D007C007B487A69
:101DA00042120A597B03900009120FF97B007A0056
:101DB000020A187D011203F2701A7B0390000112CF
:101DC00011F1EB4A60077B017A00020A187B007A66
:0B1DD0000000020A187B017A00020A18CA

:101DD00074027B0079041209D412069A04008A83DB
:101DEB008B82E0FB7A001208CE00000A0024D91E79
:101DFB00101E691F1A1FC5202C210021D4229022EE
:101E0B00E923A8246B12069A0400120553017B00EB
:101E1B008B0512069A06001206437DE87C037B00B5
:101E2B007A00090002D1206DFE4FDFCFBFA900029EE
:101E3B001206DF7B00120A3D7B2F120A3D7B007AD4
:101E4B0000120A4B7D007C007BFA7A42120A597B06
:101E5B0002900009120FF97B007A00020A187B022C
:101E6B0090000011211F1EB4A70077B007A00020A15
:101E7B00189003EBE0FAA3E0FB8B058A049003F0C8
:101E8B00E0FAA3E0FB1207248B058A04900020E004
:101E9B00FAA3E0FB12038B70289003EBE0FAA3E0AC
:101EAB00FB8B058A049003F0E0FAA3E0FB12072CEE
:101EBB008B058A04900020E0FAA3E0FB1203556027
:101ECB00077B027A00020A189000001212AD1206CC
:101EDB009A0400120553017B2F120A3D7B2F120A25
:101EEB003D7B007A00120A4B7D007C007B037A431A
:101EFB00120A597B02900009120FF9900000121177F
:101F0B004B70090003FEBF07B007A00020A187BC3
:101F1B00290000011211F1EB4A70077B007A00026C
:101F2B000A1890000012128B9003EBE0FAA3E0FB72
:101F3B008B058A049003F0E0FAA3E0FB1207248BD5
:101F4B00058A04900020E0FAA3E0FB12038B7028B3
:101F5B009003EBE0FAA3E0FBBB058A049003F0E01F
:101F6B00FAA3E0FB12072C8B058A04900020E0FA01
:101F7B00A3E0FB12035560077B027A00020A1812DA
:101F8B00069A0400120553017B008B0512069A0674
:101F9B0000120643D7D207C037B007A00090002D12FB
:101FAB006DFE4FDFCFBFA9000291206DF9000002F
:101FBB00120FE47B007A00020A1890000012132C17
:101FCB00EB4A70077B037A00020A1812069A040088
:101FDB00120553017B008B0512069A06001206436D
:101FEB007DE87C037B007A00090002D1206DFE4FD78
:101FFB00FCFBFA9000291206DF7B2F120A3D7B2FB8
:10200B00120A3D7B017A00120A4BE4FDFCFBFA122B
:10201B000A597B02900009120FF97B007A00020A21

:10202B00187B029000011211F1EB4A70077B007ACA
:10203B00000020A189003EBE0FAA3E0FB8B058A047D
:10204B009003F0E0FAA3E0FB1207248B058A0490BF
:10205B000020E0FAA3E0FB12038B70289003EBE067
:10206B00FAA3E0FB8B058A049003F0E0FAA3E0FBF4
:10207B0012072C8B058A04900020E0FAA3E0FB12DB
:10208B000035560077B027A00020A189000001213B6
:10209B002CEB4A70077B037A00020A1812069A048B
:1020AB00001120553017B008B0512069A06001206DF
:1020BB00437DE87C037B007A00090002D1206DFE461
:1020CB00FDFCFBFA9000291206DF7B1F120A3D7BF9
:1020DB001F120A3D7B007A00120A4B7D007C007BAD
:1020EB00907A41120A597B01900009120FF97B007B
:1020FB007A00020A187B019000011211F1EB4A7071
:10210B0077B007A00020A189003EBE0FAA3E0FBCE
:10211B008B058A049003F0E0FAA3E0FB1207248BF3
:10212B00058A04900022E0FAA3E0FB12038B7028CF
:10213B009003EBE0FAA3E0FBBB058A049003F0E03D
:10214B00FAA3E0FB12072C8B058A04900022E0FA1D
:10215B00A3E0FB12035560077B027A00020A18907A
:10216B00000012132CEB4A70077B037A00020A184B
:10217B0012069A0400120553017B008B0512069A76
:10218B0006001206437DE87C037B007A00090002D4D
:10219B001206DFE4FDFCFBFA9000291206DF7B2F11
:1021AB00120A3D7B2F120A3D7B007A00120A4B7DEF
:1021BB0007C007B017A43120A597B02900009120C2
:1021CB00FF97B007A00020A187B029000011211B2
:1021DB00F1EB4A70077B007A00020A189003EBE0E0
:1021EB00FAA3E0FB8B058A049003F0E0FAA3E0FB73
:1021FB001207248B058A04900020E0FAA3E0FB125F
:10220B00038B70289003EBE0FAA3E0FBBB058A04A9
:10221B009003F0E0FAA3E0FB12072C8B058A0490E5
:10222B000020E0FAA3E0FB12035560077B027A0063
:10223B00020A189000001212CEB4A70077B037AEA
:10224B0000000020A189000001212AD12069A04001236
:10225B000053017B008B0512069A06001206437D7F
:10226B00207C037B007A00090002D1206DFE4FDFC3E
:10227B00FBFA9000291206DF900000120FE47B009E
:10228B007A00020A1812069A0400120553017B0009
:10229B008B0512069A06001206437DE87C037B0031
:1022AB007A00090002D1206DFE4FDFCFBFA9000296A
:1022BB001206DF7B00120A3D7B2F120A3D7B017A4F
:1022CB0000120A4B7D007C007BFA7A42120A597B82
:1022DB0002900009120FF97B007A00020A187B02A8
:1022EB0090000011211F1EB4A70077B007A00020A91
:1022FB00189000012128B9003EBE0FAA3E0FBBB1E
:10230B0058A049003F0E0FAA3E0FB1207248B0587
:10231B0008A04900020E0FAA3E0FB12038B70289054
:10232B0003EBE0FAA3E0FBBB058A049003F0E0FAE1
:10233B00A3E0FB12072C8B058A04900020E0FAA384
:10234B00E0FB12035560077B027A00020A1890002B
:10235B0000012132CEB4A60077B037A00020A181257
:10236B00069A0400120553017B2F120A3D7B2F1294
:10237B000A3D7B017A00120A4BE4FDFCFBFA120AC0
:10238B00597B02900009120FF9900000121114A7B41
:10239B0000090003FEBF07B007A00020A187B029062
:1023AB00000011211F1EB4A70077B007A00020A1848
:1023BB009003EBE0FAA3E0FB8B058A049003F0E0BB
:1023CB00FAA3E0FB1207248B058A04900020E0FAA5
```

```
:102B0800E0FAA3E0FB12035560077B047A00020A8F
:102B1800187B008B0512069A06001206437DE87C9B
:102B2800037B007A0090002D1206DFE4FDFCFBFA1F
:102B38009000291206DF12069A0400120553017B41
:102B48003F120A3D7B7F120A3D7B017A00120A4B35
:102B5800E4FDFCFBFA120A597B00900009120FF9F8
:102B68007B007A00020A187D021203F26003022B2E
:102B7800FB7B009000011211F1EB4A70077B007A91
:102B880000020A1890000012136EEB4A60077B02DD
:102B98007A00020A189003EBE0FAA3E0FB8B058A9F
:102BA800049003F0E0FAA3E0FB1207248B058A04E3
:102BB800900024E0FAA3E0FB12038B702B9003EB4B
:102BC800E0FAA3E0FB8B058A049003F0E0FAA3E0A7
:102BD800FB12072C8B05BA04900024E0FAA3E0FB83
:102BE80012035560077B047A00020A187B017A00F9
:0A2BF800020A187B017A00020A1895
:102C0200740278007904120904120069A04008A83A5
:102C12008B82E0FBC0037D001203F2D003703B7BBA
:102C2200008B0512069A06001206437DC07CD47BF7
:102C3200017A0090002D1206DFE4FDFCFBFA900001
:102C4200291206DF12069A0400120553019000001B1
:102C5200120FE47B007A00020A187D011203F2705F
:0F2C6200077B017A00020A187B017A00020A1828
:102C710074027B0079041209D412069A04008A8336
:102C81008B82E0FBC0037D001203F2D00370597BFD
:102C910000120A3D7B50120A3D7B007A00120A4B5A
:102CA1007DF67C287B4C7A41120A597B00900009001
:102CB100120FF97B00BB0512069A06001206437D5E
:102CC100E87C037B007A0090002D1206DFE4FDFC16
:102CD100FBFA3000291206DF12069A04001205532E
:102CE100017B007A00020A187D011203F2600302DF
:102CF1002D757B009000011211F1EB4A70077B00EA
:102D01007A00020A1890000012136EEB4A60077BEA
:102D1100027A00020A189003EBE0FAA3E0FB8B05AC
:102D21008A049003F0E0FAA3E0FB1207248B05BAE2
:102D31000049000240FAA3E0FB12038B70289003B7
:102D41000EBE0FAA3E0FB8B058A049003F0E0FAA321
:102D5100E0FB12072C8B05BA04900024E0FAA3E023
:102D6100FB12035560077B047A00020A187B017AB3
:0B2D710000020A187B017A00020A1819
:102D7C0074027B0079041209D412069A04008A832A
:102D8C008B82E0FBC0037D001203F2D00370597BF1
:102D9C000000120A3D7B50120A3D7B007A00120A4B4E
:102DAC007DF67C287B4C7A41120A597B00900009F5
:102DBC00120FF97B00BB0512069A06001206437D52
:102DCC00E87C037B007A0090002D1206DFE4FDFC0A
:102DDC00FBFA9000291206DF12069A040012055322
:102DEC00017B007A00020A187D011203F260030203
:102DFC002EB07B009000011211F1EB4A70077B00D2
:102E0C007A00020A1890000012136EEB4A60077BDE
:102E1C00027A00020A189003EBE0FAA3E0FB8B05A0
:102E2C008A049003F0E0FAA3E0FB1207248B05BAD6
:102E3C00049000240FAA3E0FB12038B70289003AB
:102E4C00EBE0FAA3E0FB8B058A049003F0E0FAA315
:102E5C00E0FB12072C8B05BA04900024E0FAA3E017
:102E6C00FB12035560077B047A00020A187B017A77
:0B2E7C0000020A187B017A00020A1B0D
:01508100002E
```

```
:102E87007402780079041209D412069A0400BA831E
:102E97008B82E0FBC0037D001203F2D00370597BE5
:102EA7000001203A3D7B50120A3D7B007A00120A4B42
:102EB7007DF67C287B4C7A41120A597B003000009E9
:102EC700120FF97B00BB0512069A06001206437D46
:102ED700E87C037B007A0090002D1206DFE4FDCFE
:102EE700FBFA9000291206DF12069A0400120553166
:102EF700017B007A00020A187D011203F2600302C7
:102F07002FBB7B009000011211F1EB4A70077B00B9
:102F17007A00020A1890000012136EEB4A60077BD2
:102F2700027A00020A189003EBE0FAA3E0FB8B0594
:102F37008A049003F0E0FAA3E0FB1207248B058ACA
:102F47000049000240FAA3E0FB12038B7028903F
:102F5700EBE0FAA3E0FB8B058A049003F0E0FAA309
:102F6700E0FB12072C8B05BA04900024E0FAA3E00B
:102F7700FB12035560077B047A00020A187B017A6B
:0B2FB70000020A187B017A00020A1B01
:102F92007402780079041209D412069A04008A8312
:102FA2008B82E0FB7A00120BCE00000500328E2FE1
:102FB200BD301630D9318A323532877B008B05120D
:102FC20069A06001206437DEB7C037B007A009095
:102FD200002D1206DFE4FDCFBFA9000291206DF49
:102FE20012069A0400120553017B1F120A3D7B1F31
:102FF200120A3D7B007A00120A4B7D007C007B9016
:103002007A41120A597B01900009120FF97B007A6A
:1030120000020A187B01900001121F1EB4A7007BD
:103022007B007A00020A189003EBE0FAA3E0FB8B24
:1030320005BA049003F0E0FAA3E0FB1207248B0553
:103042008A04900022E0FAA3E0FB12038B7028901E
:1030520003EBE0FAA3E0FB8B058A049003F0E0FAAD
:10306200A3E0FB12072C8B05BA04900022E0FAA34E
:10307200E0FB12035560077B027A00020A187B000C
:103082008B0512069A06001206437DEB7C037B003C
:103092007A0090002D1206DFE4FDCFBFA90002975
:1030A2001206DF12069A0400120553017B00120A6F
:1030B20003D7B2F120A3D7B007A00120A4B7D007C79
:1030C200007BFA7A42120A597B02900009120FF928
:1030D2007B007A00020A187B029000011211F1EBC8
:1030E2004A70077B007A00020A189003EBE0FAA309
:1030F200E0FB8B058A049003F0E0FAA3E0FB1207E1
:10310200248B058A04900020E0FAA3E0FB12038BD3
:103112007028903EBE0FAA3E0FB8B058A0490038E
:10312200F0E0FAA3E0FB12072C8B058A04900002042
:10313200E0FAA3E0FB12035560077B027A00020A61
:10314200189000001212AD12069A04001205530E3
:103152007B2F120A3D7B2F120A3D7B007A00120A56
:103162004B7D007C007B017A43120A597B0290005E
:1031720009120FF990000012114A7B0090003FEBFB
:10318200F07B007A00020A187B029000011211F112
:1031920009EB4A70077B007A00020A189000001212B4
:1031A200889003EBE0FAA3E0FB8B058A049003F01E
:1031B200E0FAA3E0FB1207248B058A04900020E0CA
:1031C200FAA3E0FB12038B7028903EBE0FAA3E072
:1031D200FBB058A049003F0E0FAA3E0FB12072CB4
:1031E2008B058A04900020E0FAA3E0FB12035560ED
:1031F200077B027A00020A18120690A0400120553BB
:10320200017B008B0512069A06001206437D0207C84
:10321200037B007A0090002D1206DFE4FDCFBFA2E
```

```
:1023DB00A3E0FB12038B70289003EBE0FAA3E0FB66
:1023EB008B05BA049003F0E0FAA3E0FB12072C8B19
:1023FB00058A04900020E0FAA3E0FB120355600766
:10240B007B027A00020A1B12069A04001205530185
:10241B007B008B0512069A06001206437DE87C03AF
:10242B007B007A0090002D1206DFE4FDFCFBFA9096
:10243B0000291206DF7B1F120A3D7B1F120A3D7B10
:10244B00017A00120A4BE4FDFCFBFA120A597B01DC
:10245B00900009120FF97B007A00020A187B019099
:10246B0000011211F1EB4A70077B007A00020A1B87
:10247B009003EBE0FAA3E0FB8B058A049003F0E0FA
:1024BB00FAA3E0FB1207248B058A04900022E0FAE2
:10249B00A3E0FB12038B70289003EBE0FAA3E0FBA5
:1024AB008B058A049003F0E0FAA3E0FB12072C8B58
:1024BB00058A04900022E0FAA3E0FB1203556007A3
:1024CB007B027A00020A1B7B017A00020A1B7B0150
:0524DB007A00020A185E
:1024E0007402780079041209D412069A04008AB3CF
:1024F0008B82E0FB7A001208CE000007002A11252B
:102500000F2568262726F827CC288828E129A0123D
:1025100069A0400120553017B008B0512069A06E9
:102520000001206437DE87C037B007A0090002D12A8
:102530000006DFE4FDFCFBFA9000291206DF7B0012A7
:102540000A3D7B2F120A3D7B017A00120A4B7D0067
:102550007C007BFA7A42120A597B02900009120F22
:1025600097B007A00020A187B029000011211F137
:10257000EB4A70077B007A00020A189000001213E1
:10258000079003EBE0FAA3E0FB8B058A049003F0C
:10259000E0FAA3E0FB1207248B058A04900020E0F8
:1025A000FAA3E0FB12038B70289003EBE0FAA3E0A0
:1025B000FB8B058A049003F0E0FAA3E0FB12072CE2
:1025C0008B058A04900020E0FAA3E0FB1203556018
:1025D00077B027A00020A1890000012132CEB4AC3
:1025E00070077B037A00020A1812069A04001205BB
:1025F00053017B2F120A3D7B2F120A3D7B017A008B
:10260000120A4BE4FDFCFBFA120A597B02900009006
:10261000120FF990000012114A7B0090003FEBF07E
:102620007B007A00020A187B029000011211F1EB84
:102630004A70077B007A00020A189003EBE0FAA3C5
:10264000E0FB8B058A049003F0E0FAA3E0FB12079D
:10265000248B058A04900020E0FAA3E0FB12038B90
:1026600070289003EBE0FAA3E0FB8B058A04900348B
:10267000F0E0FAA3E0FB12072C8B058A04900020FF
:10268000E0FAA3E0FB12035560077B027A00020A1E
:102690001890000012132CEB4A70077B037A00029B
:1026A000A187B008B0512069A06001206437DE885
:1026B0007C037B007A0090002D1206DFE4FDFCFB1A
:1026C000FA9000291206DF12069A0400120553013F
:1026D0007B1F120A3D7B1F120A3D7B017A00120A02
:1026E0004BE4FDFCFBFA120A597B01900009120F22
:1026F000F97B007A00020A187B019000011211F1A7
:10270000EB4A70077B007A00020A189003EBE0FAAC
:10271000A3E0FB8B058A049003F0E0FAA3E0FB1230
:102720007248B058A04900022E0FAA3E0FB120341
:102730008B70289003EBE0FAA3E0FB8B058A0490F2
:1027400003F0E0FAA3E0FB12072C8B058A049004B
:1027500022E0FAA3E0FB12035560077B027A000235
:102760000A1890000012132CEB4A70077B037A00C2
```

```
:102770000020A187B008B0512069A06001206437D9A
:1027800E87C037B007A0090002D1206DFE4FDFC5C
:10279000FBFA9000291206DF12069A040012055374
:1027A000017B2F120A3D7B2F120A3D7B007A00121B
:1027B0000A4B7D007C007B037A43120A597B02900E
:1027C000000009120FF97B007A00020A187B029000C0
:1027D0000011211F1EB4A70077B007A00020A1908F
:1027E00003EBE0FAA3E0FB8B058A049003F0E0FA28
:1027F000A3E0FB1207248B058A04900020E0FAA3D3
:10280000E0FB12038B70289003EBE0FAA3E0FB8B54
:10281000058A049003F0E0FAA3E0FB12072C8B0575
:102820008A04900020E0FAA3E0FB12035560077BC6
:10283000027A00020A1890000012132CEB4A70076B
:102840007B037A00020A189000001212AD7B008B05
:102850000512069A06001206437D207C037B007A4F
:102860000090002D1206DFE4FDFCFBFA9000291217
:1028700006DF12069A040012055301900000120FA1
:10288000E47B007A00020A187B008B0512069A0688
:1028900001206437DE87C037B007A0090002D1235
:1028A00006DFE4FDFCFBFA9000291206DF12069A0F
:1028B000400120553017B00120A3D7B2F120A3DD2
:1028C0007B017A00120A4B7D007C007BFA7A42126F
:1028D000A597B02900009120FF97B007A00020A64
:1028E000187B029000011211F1EB4A70077B007A0D
:1028F00000020A189000001212889003EBE0FAA37D
:10290000E0FB8B058A049003F0E0FAA3E0FB1207DA
:10291000248B05BA04900020E0FAA3E0FB12038BCD
:1029200070289003EBE0FAA3E0FB8B058A04900388
:10293000F0E0FAA3E0FB12072C8B058A0490002003C
:10294000E0FAA3E0FB12035560077B027A00020A5B
:102950001890000012132CEB4A60077B037A0002EB
:10296000A1812069A0400120553017B2F120A3D21
:102970007B2F120A3D7B017A00120A4BE4FDFCFB1F
:10298000FA120A597B02900009120FF99000001206
:10299000114A7B0090003FEBF07B007A00020A189E
:1029A0007B029000011211F1EB4A70077B007A0064
:1029B00020A189003EBE0FAA3E0FB8B058A04906F
:1029C00003F0E0FAA3E0FB1207248B058A049000D1
:1029D00020E0FAA3E0FB12038B70289003EBE0FAEF
:1029E000A3E0FBB8B058A049003F0E0FAA3E0FB125E
:1029F00072C8B058A04900020E0FAA3E0FB120369
:102A000055600077B027A00020A187B017A00020AED
:082A1000187B017A00020A188C
:102A18007402780079041209D412069A04008A8391
:102A28008B82E0FBC0037D001203F2D000370597B58
:102A38008B0512069A06001206437DE87C037B8C
:102A480007A0090002D1206DFE4FDFCFBFA9000EE
:102A580029120DF12069A0400120553017B0012A0
:102A68000A3D7B50120A3D7B007A00120A4B7D9A80
:102A78007C997B2F7A41120A597B00900009120F2A
:102A88000F97B007A00020A18C0037D011203F2D0014
:102A98000036003022B6F7B009000011211F1EB4AD7
:102AA00070077B007A00020A18900012136EEB80
:102AB0004A60077B027A00020A189003EBE0FAA347
:102AC800E0FB8B058A049003F0E0FAA3E0FB120711
:102AD800248B058A04900024E0FAA3E0FB12038B00
:102AE80070289003EBE0FAA3E0FB8B058A049003BF
:102AF800F0E0FAA3E0FB12072C8B05BA0490002460F
```

```
:10322200090002912060DF900000120FE47B007A0062
:103232000 20A1890000012132CEB4A70077B037AE3
:10324200000 20A189000001212D212069A0400120A
:103252000553017B008B0512069A06001206437D78
:10326200207C037B007A0090002D1206DFE4FDFC37
:10327200FBFA9000291206DF900000120FE47B0097
:103282007A00020A187B017A00020A187B017A008E
:03329200020A1815
:1032950007402780079041209D412069A04008A830C
:1032A5000BBB2E0FBC0037D001203F2D00370567BD6
:1032B500008B0512069A06001206437DE87C037B07
:1032C500007A0090002D1206DFE4FDFCFBFA900069
:1032D500291206DF12069A0400120553017B3F12DC
:1032E5000A3D7B7F120A3D7B017A00120A4BE4FD01
:1032F500FCFBFA120A597B009000009120FF97B00BA
:103305007A00020A18C0037D011203F2D00360039C
:103315000233A37B0090000011211F1EB4A70077B89
:1033250000 7A00020A1890000012136EEB4A60073B
:103335007B027A00020A189003EBE0FAA3E0FB8B0C
:103345000058A049003F0E0FAA3E0FB1207248B053D
:103355008A04900024E0FAA3E0FB12038B70289006
:103365000 3EBE0FAA3E0FB8B05BA049003F0E0FA97
:1033750 0A3E0FB12072C8B058A04900024E0FAA336
:10338500E0FB12035560077B047A00020A18120657
:103395009A0400120553017B007A00020A187D02B7
:1033A5001203F2702590C006E0FB7A00120 63B8BF3
:1033B50005 8A047B807A00120 63360077B007A0059
:1033C500020A187B017A00020A187B017A00020AB8
:0133D50018DF
:1033D60007402780079041209D412069A04008A83CA
:1033E6008B82E0FBC0037D001203F2D00370597B91
:1033F6001F120A3D7B1F120A3D7B007A00120A4B00
:1034060 07D007C007B487A42120A597B03900009B2
:10341600120FF97B008B0512069A06001206437DF1
:10342600E87C037B007A0090002D1206DFE4FDFCA9
:10343600FBFA9000291206DF12069A0400120553C1
:1034460001 7B007A00020A187D011203F2702B7BC1
:10345600039000011211F1EB4A70077B007A00021B
:103466000A1890000012136EEB4A60077B027A007E
:10347600020A187B017A00020A187B017A00020A06
:013486000182D
:1034870007402780079041209D412069A04008AB318
:103497008B82E0FB7A001208CE00000400369B34D5
:1034A70 0B03506357435E2367E7B008B0512069AF9
:1034B700060012 06437DE87C037B007A0090002D0E
:1034C7001206DFE4FDFCFBFA9000291206DF120664
:1034D7009A0400120553017B2F120A3D7B2F120A13
:1034E7003D7B017A00120A4BE4FDFCFBFA120A59F4
:1034F7007B029000091 20FF97B007A00020A187B01
:10350700029000011211F1EB4A605B7B007A00909B
:10351700020EAF0EBA3F07B008B0512069A060069
:103527001206437DE87C037B007A0090002D12068B
:103537000DFE4FDFCFBFA9000291206DF12069A046D
:1035470000120553017B1F120A3D7B1F120A3D7BA8
:1035570017A00120A4BE4FDFCFBFA120A597B01BF
:103567009000091 20FF97B00 7A00020A187B01907C
:103577000 00011211F1EB4A605B7B007A00900229B
:1035B700EAF0EBA3F07B008B0512069A0600120601
:1035970 0437DE87C037B007A0090002D1206DFE470
:1035A700FDFCFBFA9000291206DF12069A040012AE
:1035B7000 0553017B3F120A3D7B3F120A3D7B017A8F
:1035C7000 00120A4BE4FDFCFBFA120A597B009003B
:1035D700091 20FF97B007A00020A187B009000019C
:1035E7001211F1EB4A70030236777B007A0009000E4
:1035F70024EAF0EBA3F090C007E0FB8B057B0AEB16
:10360700050DFBBB057B0A1203E360137B007A009056
:1036170000026EAF0EBA3F07B017A00020A187B0090
:103627008 B0512069A06001206437DE87C037B0091
:103637007A0090002D1206DFE4FDFCFBFA900029CA
:10364700120 6DF12069A0400120553017B1F120AA5
:103657003D7B1F120A3D7B017A00120A4B7D007CDD
:1036670007B4B7A42120A597B03900009120FF92E
:1036770 07B007A00020A187B03900001121F1EB1C
:1036870 04A60077B017A00020A187B007A00020A67
:08369700187B017A00020A18F9
:10369F00E47B0079041209D47BC7BBCA7BFEBBCBED
:1036AF007B348BC87B528B98C298C299D2AC90C096
:1036BF0006E0FBEBF4FBBB057B07EB5DFB90004813
:1036CF00EBF0D2907B0090004BEBF07B0090004929
:1036DF00EBF07B0090004AEBF07B009000B4EBF036
:1036EF007B019000B6EBF07B0090004CEBF07B0081
:1036FF0090004DEBF07B0090004FEBF0020A18E4C6
:10370F007B0079041209D47B0090004CEBF07B0118
:10371F0090004DEBF07B0090004FEBF0020A187415
:10372F000017B0079041209D49000B6E0700280F895
:10373F00C29012 06BE400 8B997B0090 00B6EBF0BE
:10374F00020A1874027800790A1209D47B007A00F1
:10375F0012 06F706007B007A001206F708007B02BC
:10376F008B0512069A0C00120A44BB058A04740703
:10377F002FFBE43EFA12055302120724120A6012BD
:10378F000064 3900048E0FB8B057B30EB2DFB8B0550
:10379F0012 069A0C00120A44BB058A0474072FFB39
:1037AF00E43EFA12055302120724120A601206436E
:1037BF0012 069A0A00120A4B12069A0E00BB058AFD
:1037CF000 04120 69A08001207249000041246921 25F
:1037DF00069A0090 00021246D2B0B058A047406DC
:1037EF002FFBE43EFA1201147B007A001206F70455
:1037FF00 00012069A0A009000021246D2B0B058A0424
:10380F0012069A0400120355604512069A0C008B9B
:10381F00058A0412069A0400120A528B058A047B49
:10382F0002 7A00120724120A671207248A38B82F6
:10383F00E0FB7A008B058A0474082FFBE43EFA1232
:10384F00011474042FFBE43EFA12055302B0A212F6
:10385F0069A08001207798B058A047BF7A0012FB
:10386F00006331206F7080012069A0C008B058A041D
:10387F0012069A06001 20724120A4B12069A0A0021
:10388F000900003124416E7B027A008B058A04740693
:10389F002FFBE43EFA1201147B038B0512069A0CE0
:1038AF000001 20A44BB058A0412069A07001207495
:1038BF00120A601 20643020A1874027800790412B1
:1038CF009D47B827A00120A4B12069A06009000E6
:1038DF00041237 5290000012370E7B0090004EEB0F
:1038EF000 F0020A18E4780079041209D490004DE030
:1038FF0060 569000B6E060507B827A008B058A049B
:10390F009000 04CE0FB7A0012 07248A838B82E0FB45
:10391F009000 01123 72E7B827A008B058A047B4C34
```

:10392F007A00120553017A001207248A838B82E0F2
:10393F00FBBB057B031203E3600E7B0090004DEBC6
:10394F00F07B0190004FEBF0020A187402780079B7
:10395F00041209D412069A04008AB3BBB2E0FB7A40
:10396F00008B058A047BD07AFF1207248B058A040B
:10397F00900048E0FB7A001203E7607812069A0481
:10398F00008B058A047B017A001207249000021233
:10399F0045DBEB60577B00BB0512069A0400120A7C
:1039AF0044120A4B12069A07009000021246D212D6
:1039BF000A67120A52BB058A047BFE7AFF120724CC
:1039CF00120A67120724120A6012064378069000040
:1039DF000112372E12069A04008B058A047B017A96
:1039EF0000120724900002123D1180087B159000F1
:1039FF000112372E020A187401780079041209D4C3
:103A0F0012068E040012090F3A27023A3F033A7446
:103A1F00063A7D1500003A9F7B0090004BEBF07B40
:103A2F0001900049EBF07B0090004FEBF0023AE180
:103A3F00900049E0602D7B0190004AEBF07B0090F5
:103A4F000049EBF07B00BB057B507A00120A44BB0B
:103A5F00058A0430004BE0FB7A00120724120A60DB
:103A6F00120643B06D7B0090004FEBF080647B4E1D
:103A7F007A001204BB018057B051203C660097B1C
:103A8F000090004FEBF0800690000012370E80423E
:103A9F00900049E0603A12068E04008057B507A45
:103AAF0000120A44BB058A047B4B7A00120553010E
:103ABF007A00120724120A6012064390004BE0FBB3
:103ACF008B057B321203E360077B0090004BEBF01A
:103ADF008000020A18E4780079041209D49000B427
:103AEF00E060299000B5E0FB9000011123A067B00E0
:103AFF009000B4EBF030004AE060117B507A009098
:103B0F000000212395A7B0090004AEBF0020A18E4C7
:103B1F00780079041209D490000012AE4300000062
:063B2F00123BF3020A182F
:103B3500740278007904129D412069A04008B05E0
:103B45008A047B027A00120724900002124F59041
:103B55000000112B70020A18E4780079041209D4E6
:103B65009000001211BD7B07120A3D7B477A0012E7
:103B75000A4B7B467A00120A4B7B457A009000778
:103B8500121391020A1BE4780079041209D47B1201
:103B9500900045EBF0020A187401780079041209C7
:103BA500D490003DE0604B900006E0FB7A00120AE0
:103BB5004B9000351206CD120A599000391206CDE8
:103BC500120A599000E0FB7A00120A4B7B2A7A09
:103BD50000120A4B7B327A01120A4B7BB77A0090AE
:103BE5000001212472B700900003DEBF0023D0412C2
:103BF500068E040012090F3C0C003C37113C96124E
:103C05003C621300003CC09000021206CD120A5916
:103C15007B027A00120A4B7B297A00120A4B7B46FB
:103C25007A01120A4B7BB77A0090000C12472B02DF
:103C35003D049000021206CD120A597B057A001246
:103C45000A4B7B297A00120A4B7B527A01120A4BE6
:103C55007BB77A0090000C12472B023D049000028E
:103C65001206CD120A599000042E0FB7A00120A4B67
:103C75007B067A00120A4B7B297A00120A4B7B5E7F
:103CB5007A01120A4B7BB77A0090000E12472B80FF
:103C95006E9000021206CD120A597B077A00120AAD
:103CA5004B7B297A00120A4B7B6E7A01120A4B7BF9
:103CB500B77A0090000C12472B8044120068E040040
:103CC5008B057B011203C660361206BE04008B053B
:103CD5007B0F1203D360289000021206CD120A59F9
:103CE5007B037A00120A4B7B297A00120A4B7B7AF6
:103CF5007A01120A4B7BB77A0090000C12472B7B96
:103D0500B77A009000021238C8020A187402780007
:103D1500790412094120469A04008A838B82E0FB87
:103D25007A00120BCE220006003D843D3E3D4B3D03
:103D3500053335D5B3D5D3D5F3D7712069A040090063
:103D450002123B358039900000123B5D80319000B6
:103D550000012388B802980278025120069A04008B50
:103D65000058A047B027A00120724900002124374C2C
:103D75000800D900045E0FB90000112389D80000204
:023D85000A181A
:10508200253163202532642025656420256C642040
:10509200253164002531632025326420256C6400AB
:1050A20025316320253264025666420253163207C
:1050B20025326420253264202566642025316320(A
:1050C20025326420256C640253163202532642A05A
:0450D20025656400E5
:103DB700E4780079041209D47B003094010B020A0D
:103D970018E4780079041209D47B003093010B02F0
:103DA700A187401780079041209D41206BE0400E7
:103DB70090C003EBF0020A18E4780079041209D4E2
:103DC70090C003E0FB020A18E4780079051209D41
:103DD7007B009000ECEBF07B009000EFEBF07B00BA
:103DE7009000ECEBF07B009000F0EBF07B00900094
:103DF700F1EBF07B009000EBEBF07B009000EEEB3B
:103E0700F07B009000EDEBF07B217A009000E9EA6F
:103E1700F0EBA3F07B007A00090012FEAF0EBA3F020
:103E270090000012123DBF1206F104007B3C8B8D7B96
:103E3700B08B8BC28FD2ABD28E020A18E47800798E
:103E4700041209D47B009000EFEBF07B019000ECAB
:103E5700EBF07B009000F0EBF07B009000F1EBF0D3
:103E67007B007A0090012FEAF0EBA3F0020A1874A6
:103E7700027800790A1209D47B007A001206F70645
:103E87000007B007A001206F70B007B02BB051206FA
:103E97009A0C00120A448B058A0474072FFBE43E30
:103EA700FA12055302120724120A6012064312067A
:103EB7009A0A00120A4B12069A0E008B058A041200
:103EC70006980012072490000412469212069AD6
:103ED7000A009000021246D28B058A0474062FFB53
:103EE700E43EFA1201147B007A001206F70400126E
:103EF7006009A009000021246D28B058A0412061F
:103F070009A0400120355604512069A0C00BB058A25
:103F1700041206A040012A528B058A047B017A5E
:103F270000012072404120A671207248A838B82E0FB9B
:103F37007A008B058A0474082FFBE43EFA120114F9
:103F470074042FFBE43EFA1205530280A212069A6C
:103F5700080012077798B058A047BFF7A0012063363
:103F67001206F70800120069A0C008B058A0412063F
:103F77009A0600120724120A4B12069A0A009000AA
:103F87000003124413F1E7B027A00BB058A0474062FFBFA
:103F9700E43EFA12011147B038B0512069A0C0012F9
:103FA7000A448B058A0412069A0700120724120A8C
:103FB70060120643020A187402780079041209D4C1
:103FC7007B117A01120A4B12069A0600900004121E
:103FD7003E76900000123E437B009000F2EBF00229
:103FE7000A18E4780079081209D47B231206F10431

:103FF700007B001206F1050074042FFBE43EFA90E3
:104007000002123FBE7B019000F1EBF0020A18E4B8
:10401700780079041209D49000ECE0605990000010
:10402700123DB7EB60507B117A018B05BA04900063
:104037000EFE0FB7A001207248A838B82E0FB90073
:104047000112 3DA97B117A018B05BA047BEF7A0067
:10405700120553017A001207248A838B82E0FB8BB7
:104067000057B031203E3600E7B009000ECEBF07B13
:10407700019000F0EBF0020A18740278007904123C
:10408700009D412069A04008AB3BB82E0FB7D2412EE
:104097000003F2703912069A04008B058A047B027AB0
:1040A700001207243000021244AA90013IEBF0128B
:1040B700069A04008B058A047B057A001207249070
:1040C7000002124585900002120 6DF8000020A18DE
:1040D7007402780079041209D412069A0400900039
:1040E700021245D8EB4A60537B008B0512069A04EF
:1040F70000120A44120A4B12069A070090000021295
:104107004 6D2120A67120A528B058A047BFE7AFF8F
:10411700120724120A67120724120A6012064 37B49
:1041270006900001123DA97B003000F1EBF012060A
:104137009A0400900002 12408080 0B7B15900001CD
:10414700123DA9020A18740178007904120 9D412E1
:10415700068E040012 090F416E0 241B60341BC0618
:10416700041C515000041EE7B009000EEEBF07B01AE
:10417700 9000EBEBF07B009000F0EBF00242309008
:104187 00 00EBE0602D7B019000EDEBF07B009000F1
:10419700EBEBF07B008B057BF37A00120A448B056F
:1041A7008A049000EEE0FB7A00120724120A6012DC
:1041B70006430242307B009000F0EBF0B06B7BF20D
:1041C7007A001204BB018B057B051203C660107BC6
:1041D700009000F0EBF07B009000F1EBF080069090
:1041E7000000123E4380429000EBE0603A12068ED8
:1041F700040 0 8B057BF37A00120A448B05BA047B43
:10420700EE7A00120553017A00120724120A60128F
:1042170006439000EEE0FB8B057B321203E3600759
:104227007B009000EEEBF08000020A18E47800793A
:1042370 0041209D490012FE0FAA3E0FBBB05BA044E
:1042 4700 7B647A00120374020A18E4780079041276
:104257009D4900000123D9BEB60259000000123DB4
:104267 00BF90000112414D9000EDE0601 7BF37AA1
:10427700009000021240D77B009000EDEBF0B03CED
:104287009000F0E070069000F1E0 603090000012BE
:104297004233EB60277BF27A001204BB018B057B6C
:1042A700051203C660107B009000F0EBF07B0090D6
:1042B70000 0F1EBF08006900000123E43020A1874EA
:1042C70002780079041209D49000E9E0FAA3E0FB30
:1042D7008B05BA047B217A001203E7600D12069A88
:1042E7 00040 03000E9EAF0EBA3F0020A18E4780072
:1042F7007 9131209D49000ECE0603024371900037
:104307 00F0E070669000F1E070609000E9E0FAA3D9
:1043170 0E0FBEA7049C0037D211203F2D00370026B
:10432700803C7D221203F27035900000E0FAA3E092
:10433700FB120A4B7B227A00120A4B7B867A01120B
:104347000A4B740A2FFBE43EFA9000 0812472B74BD
:1043570 042FFBE43EFA900002123FBEB0007B214F
:104367007A009000E9EAF0EBA3F0020A18740278E9
:1043770000079041209D412069A040090000212452B
:1043 8700 040900000EAF0EBA3F07B227A009000E96E

:10439700EAF0EBA3F0020A18E4780079041209D4D2
:1043A700 9000 00124251900000124016900000 12 37
:1043B700042F49000ECE070279000F0E0702190004C
:1043C700F1E0701B90012FE0FAA3E0FB8B058A0454
:1043D7007B647A00120374600 69000 00123FE902C2
:0243E7000A18B2
:0850D60002531632 02533 64003D
:1043E90007401780079041209D412 068E04008B0531
:1043F9007B0 9120370600F12068E04008B057B3750
:104409 00EB2DFB020A181206BE04008B057B30EB9C
:104419002DFB020A18740017 800 79041209D41206D6
:104429008E04008B057B047C001205D590 0 00112D7
:1044390043E9 8B0 5120 69A050012 064312068E04FB
:104449 00008B057B0FEB5DFB900 0 0 11243E9 8B05A7
:104459 0012 069A0500120A44 8B058A047B017A0 028
:1044 69001207241 20A601206 43020A18740178001E
:1044 7900079 041209D412 068E0 4008B057B391203C4
:1044 8900070 600F12068E04 008B057BC9EB2DFB02B1
:10 4499000A1812068 E04 008B057BD0EB2DFB020A4D
:1044A90018740278 0 07 9041209D412069A040 08A51
:1044B90083 8B82E0FB9 0 0 001124 475 8B057B047CA1
:1044 C900001205F012 0A3D12069A05 00 8B 0 58A0 4AE
:1044D9 007B017A00120724 8A 838B82E0FB9 0 0 0 011A
:1044E9 001244 751 20A 60EB 2DFB0 2 0A1874 027 80 57
:1044F 90 0 07 9041209D412 0 69A 0 4 0 08A8 38B82E0FB9C
:1045 0 9 0 0 9 0 0 0 011244 75 BB 0 57B0AEDBBF 0A4FB1218
:1045 1 9 0 0 0A3D12 0 69A 0 5 0 0 8B 058A04 7B 017A001 26E
:10452900007 24 BA 83 8B82E0FB 90 0 0011244 75 120AEA
:1045390060 EB2DFB 020A 1874027 80 07 9 041209D481
:104549 0012 06 9A 04 0 09 0 0 0 0 212 44F 57A 0 0 8B0 58A3B
:10455 9 0 0 047B647A 0 0 1207 35 120A4B12 0 69A 0 6 0 08 8
:1045 69 0 0 8B0 58A0 47B027A 0 0 1207249 0 0 0 021244 0B
:1045 79 0 0F 5120A67 7A 0 0 12 07 24 020A18 740 278 00F1
:1045 89 0 0 0 079 041 2 09D412 0 69A 0 4 0 0 9 0 0 0 02124 54 0D7
:1045 99 0 0 8B 058A0 47B 0A 7A 001 207 35 12 0A4B12 0 628
:10 45A9 0 0 9A0 60 0 8B 0 58A0 47B047A 0 0 1207 24BA8 301
:1045B9 0 0 8B 82E 0FB 9 0 0 0 0 11244 75 12 0A67 7A 0 0 1 29F
:1045 C9 0 0 0724EAFC3 3E 49 5E 08B 0 5FBFA 0 20A18742B
:1045D90002 78 00 7 9 0A12 09D47B 007A0 01 206F 7 0 4DE
:1045 E9 0 0 0 07B 007A 001 2 06F 7 0 8 0 01206 9A 0A 0 0 90 6A
:1045F9 0 0 0 0 0 021 246D28B 0 58A0 47BFE7AFF 12 07 2 439
:104 60 9 0 08B 058A0 41 2 0 69A 0B0 01 2 0355 60 34 12 06B 3
:104619 009A 0A 0 08B 0 58A0 41 2 06 9A 0B0 01 207 248A4E
:10 4629 0 0 8 38BB 2E0FB7A 0 0 8B 058A0 4740 4 2FFBE 4F8
:104 63 9 0 0 3EFA12 0 11474 0 82FFBE43EFA12 0 55 3 02E4
:1046490080A812069A0A0 08B058A0412069A 0800A5
:10 465 9 0 01 2 07 249 0 0 0 021244AA 7A 0 0 1 206F 7 0 60 0F3
:1046 69 0 0 12 0 69A 0 4 0 0 8B 0 58A0 412 06 9A 0 6 0 0 12 07 9C
:104 67 9 0 024 8B 0 58A0 47BFF 7A 0 0 12 0 6 33EB4A 6 0 0 219
:094 6 8 9 0 074FF 04 FB 7A 0 0 0 2 0A1B18
:030 0 0 0 0 0 0 2 0 10 0FA
:03 0 0 0 3 0 0 0 2 5 2CADC
:0 3 0 0 0B0 0 0 25 1D8C7
:03 0 013 0 0 02513 661
:03 0 01B0 0 0 25 3 8 4 0 9
:0 3 0 0 2 3 0 0 0 2 5 355 3 0
:10 0 1 0 0 0 0 7 5 813 0C2D 3C2D 41 2 0 9 35 7E0 3 7FE 6 9 0 0 0D 8
:0 40 11 0 0 0 0 0 0 0 2 0BA9 35

```
:10469200740278007906120904120069A06001206EC
:1046A200F7040074082FFBE43EFA1205530280AB3D2
:1046B2008B82E0FB8B0574062FFBE43EFA12055356
:1046C200021206436002B0DB12069A0400020A18F4
:1046D200740278007906120904120069A06001206AC
:1046E200F7040012069A04008A838B82E0600D743C
:1046F200042FFBE43EFA1205530280E712069E04E1
:0C4702000012069A060012072C020A188A
:10470E0074017800790412090412094040012067A
:10471E003A05001205530212064320A1874027813
:10472E000079081209D4740A2FFDE43EFC7B027A4C
:10473E0001207241206F7040074042FFBE43EFA5D
:10474E00120A4B740A2FFBE43EFA120A4B7B0E7AC6
:10475E0047120A4B12069A10009000081247841254
:10476E0006F706007D0012069A080012064312068E
:06477E009A0600020A1871
:104784007402780079AA1209D47B007A001206F721
:10479400110074AA2FFBE43EFA120553028A838B9C
:1047A40082E0FB1206F104008B057B251203F26004
:1047B4003C12068E0400700812069A1100020A18B0
:1047C40012069AAE00120A4B1206BE0600BB0512D0
:1047D400069AAE00C003C0028D03900003120A2C97
:1047E40074112FFBE43EFA1205530280A512069AB7
:1047F400AA008A838B82E0FB8B057B251203E3608E
:104804003674AA2FFBE43EFA12055302120069AAE3E
:10481400000120A4B7B258B0512069AAE00C003C01A
:1048240002BD03900003120A2C74112FFBE43EFA4C
:104834001205530202479678001206F113007B0017
:104844001206F1140012069AAA008A838B82E0FBF6
:104854008B057B2B1203E3701412069AAA008A8339
:104864008B82E0FB8B057B201203E3601874AA2F74
:10487400FBE43EFA120553028A838B82E0FB1206A4
:10488400F11300802E12069AAA008AB3B8B2E0FB21
:1048940008B057B2D1203E3601874142FFBE43EFA9E
:1048A4001205530174AA2FFBE43EFA120553028049
:1048B40002800280901206 9AAA008A838B82E0FB0F
:1048C4008B057B301203E360147B011206F1230095
:1048D40074AA2FFBE43EFA1205530280077B0012F0
:1048E4006F1230012069AAA008A838B82E0FBBBCE
:1048F400057B2A1203E3605312069AB000012052EB8
:10490400000028A838B82E0FAA3E0FB1206F70F0011
:1049140012069E0F007B007A0012038B60201206A1
:104924009A0F001207791206F70F0012068E140070
:10493400EB600274FF04FB7A001206F1140074AAFF
:104944002FFBE43EFA12055302806F7B007A0012BB
:104954006F70F0012069AAA008A838B82E0FBB8B6B
:10496400057B301203C6605212069AAA008AB3B12
:1049740082E0FB8B057B391203D3603E312069E0F47
:1049B400007B0A7A001207358B05BA0474AA2FFB70
:10499400E43EFA120553028A838B82E0FB7A00120A
:1049A4000A528B05BA047BD07AFF120724120A6705
:1049B40012072412 06F70F00809A12069AAA008A9B
:1049C40083 9BB2E0FB8B057B2E1203E37003024A88
:1049D4008574AA2FFBE43EFA1204BB028A838B82FD
:1049E400E0FBBB057B2A1203E3602512069AB000D4
:1049F40012052E00028A838B82E0FAA3E0FB1206E2
:104A0400F7050074AA2FFBE43EFA12055302B06FE7
:104A14007B007A001206F7050012069AAA008A8320
```

```
:104A24008B82E0FB8B057B301203C6605212069A20
:104A3400AA008A838B82E0FB8B057B391203D36047
:104A44003E12069E0500780A7A001207358B058A02
:104A540000474AA2FFBE43EFA120553028A838B8264
:104A6400E0FB7A00120A528B058A047BD07AFF128B
:104A74000724120A671207241206F70500809A8099
:104A8400097BFF7AFF1206F7050012069AAA008A2C
:104A94000838BB2E0FBBB057B6C1203E360167B0146
:104AA4007A001206F7070074AA2FFBE43EFA1205F7
:104AB400530280097B007A001206F7070074AA2FBC
:104AC400FBE43EFA120553028A838B82E0FB120652
:104AD400F10400120904FEE9004EC0454BD6584B65
:104AE400005634D43644EC0654EB9664D43694BD66C
:104AF4006F4BD6704B43734D43754BD67800004EC5
:104B0400F412069AB00012052E00028A838B82E00A
:104B1400FAA3E0FB1206F1240074242FFBE43EFA0E
:104B24001206F71D001206F71F0012068E240060FD
:104B3400B741F2FFBE43EFA12055302024F1212AC
:104B4400069AB00012052E00028A838B82E0FAA333
:104B5400E0FB1206F71D0070097B8E7A011206F73E
:104B64001D0012069E0507B007A0012038B60096B
:104B74007B107A271206F7050078007A001206F7ED
:104B84000D00741D2FFBE43EFA120553028A838B39
:104B940082E0601C12069E0D0012069A05001203A4
:104BA4008B600D740D2FFBE43EFA1205530280D284
:104BB400741D2FFBE43EFA1204C1021206F71F0013
:104BC40012069E0D00741D2FFBE43EFA12011D0215
:104BD4004F1212069404007B701203E36022120643
:104BE4009AB00012052E00028A838B82E0FAA3E0B9
:104BF400FBBB058A047B007A001206FB1500B03FBC
:104C040012069A07006018 12069AB00012052E00C8
:104C1400048A838BB21206CD1206FB1500802012B3
:104C2400069AB00012052E00028A838B82E0FAA352
:104C3400E0FB8B058A047B007A001206FB150074E6
:104C4400A92FFBE43EFA1206F71D001206F71F0017
:104C54007B9D7A011206F7210012069404007B6FF3
:104C6400 12 03E360147B077A001206F709007B0342
:104C74007A001206F70B00802712069404007B7852
:104C84001203E360097BAE7A011206F721007B0F61
:104C94007A001206F709007B047A001206F70B006B
:104CA40012069A2100120A4B1206A417008D038CD7
:104CB4000021 20A67120A528B05BA0412069A0B0022
:104CC400120633120A671207248A838B82E0FB8B55
:104CD400005741D2FFBE43EFA1204C102120643 12AE
:104CE400069E0B0074152FFBE43EFA12013870B0D7
:104CF40012069E0500 7B007A0012038B60111206D7
:104D04008E2300600A12069A0F001206F705001 29D
:104D1400069E1F0012069A1D0012072C8B058A049A
:104D240012069A0500120 38B60127D30741D2FFB4E
:104D3400E43EFA1204C102120643B0D3024F121257
:104D44 00069A07006018 12069AB00012052E00495
:104D54008A838BB21206CD1206FB1900B04C120640
:104D64009AB00012052E00028A838B82E0FAA3E037
:104D7400FB1206F70D0012069404007B751203E380
:104D8400601412069A0D008B058A047B007A0012C7
:104D940006FB190080141206 9A0D00EAFC33E49510
:104DA400E0BB05FBFA1206FB1900120694040 07B43
:104DB400 00751203F260181206A41900120A59E4FDD0
:104DC400FCFBFA12042060067B017A0080047B005D
```

```
:104DD4007A001206F70D0060167B2D1206F11300FF
:104DE4001206A419001208141206FB1500B01C12E6
:104DF400068E1300EB60027401FB7A001206F70DB5
:104E0400001206A419001206FB150074A92FFBE476
:104E14003EFA1206F71D001206F71F001206A4152B
:104E240000120A597D0A7C007B007A001207FA8D71
:104E3400038B057B30EB2DFB8B05741D2FFBE43EB0
:104E4400FA1204C1021206437D0A7C007B007A003B
:104E5400120A5974192FFBE43EFA12012F70BD1285
:104E6400069E05007B007A0012038B60191206BEE1
:104E740023006012120 69E0F0012069A0D001207FC
:104E84002C1206F7050012069E1F0012069A1D003A
:104E940012072C8B058A0412069A050012038B60F4
:104EA400127D30741D2FFBE43EFA1204C1021206 77
:104EB4004380380597B001206F104007BBF7A0142
:104EC4001206F71D001206F71F0012069A1F00BA29
:104ED400838B82E0600D741F2FFBE43EFA120553AE
:104EE4000280E7802974AA2FFBE43EFA12055902D6
:104EF4007BE27A011206F71D001206F71F007D04FB
:104F04007C00741F2FFBE43EFA120114B0001206B9
:104F14009E1F0012069A1D00120 72C1206F70700A6
:104F24008B058A0412069A0F001203 55600B7B004E
:104F34007A001206F70D00802612069E0F0012 0654
:104F44009A070012072C8B058A041206BE1300EBB5
:104F540060027401FB7A0012072C1206F70D00128E
:104F64006BE14007042740D2FFBE43EFA1204C145
:104F7400028B058A047B007A001203AE602A1206B3
:104F84009AAE00120A4B7B208B0512069AAE00C023
:104F940003C0028D03900003120A2C74112FFBE44A
:104FA4003EFA1205530 2B0BE1206BE1300602B12C5
:104FB400069AAE00120A4B12068E15008B051206D5
:104FC4009AAE00C003C002BD03900003120A2C7431
:104FD400112FFBE43EFA1205530274072FFBE43E43
:104FE400FA1204C1028B05BA047B007A001203AE14
:104FF4006060 3912069AAE00120A4B741F2FFBE43E6E
:10500400FA12055302BAB3BBB2E0FB8B0512069AFF
:105014 00AE00C003C0028D03900003120A2C74116 9
:105024002FFBE43EFA12055302B0AF1206BE1400E1
:1050340060 6042740D2FFBE43EFA1204C1028B058A10
:105044 0047B007A001203AE602A12069AAE0012A4
:105054 000A4B7B208B0512069AAEE00C003C0028D5A
:10506400039 00003120A2C74112FFBE43EFA12057C
:07507400 0530280BE024796C3
:1050DE00296E756C6C20706F596E74657229003065
:1050EE003132333435363738394142434445460040
:1050FE00303132333435363738396162636465 6640
:10510E0000464 6C4F4154533F2077726F6E67206B6
:10511E006F726D6174746572206 96E7374616C6CFC
:08512E00656421003F3F3F00D2
:09011400120146120 72402015EEB
:09011D00120146120 72C02015EDA
:09012600120146120 74A02015EB3
:09012F00120 16C1207E0020196B6
:0E013800120A5912 016C8D0312060B02019679
:10014600D0000D001C002C003C001C0008BB28A83EB
:08015600E0CCFAA3E0CDFB228E
:0E015E00D0D082D083F5F0EAF0A3EBF0E5F022BA
:10016C00D000D001C002C003C001C0008BB28A83C2
:10017C0078027904E0F6A308D9FA8FB28E8378028C

:0A018C007904E0C6F0A308D9F922B7
:10019600D082D083F5F07B027904E6F0A308D9FA84
:0301A600E5F0225F
:1001A900E4C0E0C0E0C0E0C0E01202A0EB7003FAD6
:1001B9008079EA6076C3947F92F3EBC3947F82F3EC
:1001C90092F3EA2BC3947FFA82F350047A00805B9E
:1001D900E581FD24FCFC24FCFBC002C0F08C007905
:1001E90004C308E613F6D9FA7A18EB24FCFB790463
:1001F900C308E613F6D9FA5006F5F092F0A6F0EC2A
:10020900024FCF87904C308E613F6D9FA30E710BB11
:10021900008D01758204C3E637F61813D582F8DA1C
:10022900C9D0F0D0020ABB001202EEE5B124F8F55C
:10023900081D0E0D005D004D003A2F292F1020333B9
:10024900EBA2E7D2E7FBEA3392F0C3947F5007E4CD
:10025900FAFBFCFD803CF924E0500F7A80E4F8FCBA
:10026900FD20F02E1A1B1C1D8028E4CDCCCBCA74AE
:100279001F99F9600F7802758204C3E613F608D551
:1002890082F9D9F130F00B78057904C3E496F618B0
:07029900D9FAEA4B4C4D229B
:1002A000EBA2E7D2E7FBEA33FA92F0D000D001C02C
:1002B0003C004C005E4C0E0C002C001C000C0F03B
:1002C000120A6ED0F0EBA2E7D2E7FBEA33FA92F122
:1002D00092F2A2F05002B2F2D082D083D001C003D9
:0E02E000C004C005E4C0E0C083C082AB0122B0
:1002EE0088827904E6700518D9FAFA22A8821818BD
:1002FE0018E630E71CA882E6C3335007700518E6EF
:1003000008A2E0790318E63400F6D9F9EA3400FAC7
:10031E0022BA01037A00221AA8827904C3E633F6C0
:05032E0018D9FA80C798
:10033300EA7006FAFBFCFDC322F9A2F113FAEB9271
:06034300E7FBE9A2F12234
:10034900EB33E495E0FAED33E495E0FCEC33EA6C49
:1003590013C0E012072CD0F0600C30F602AAF0EAC4
:0703690033B3E4FA33FB2279
:0F03700007A007C0012072C6005B3E4FA33FB22FD
:10037F00EB33E495E0FAED33E495E0FCEC33EA6C13
:10038F0013C0E012072CD0E030E601FAE4CA235480
:03039F0001FB223D
:1003A200EB33E495E0FAED33E495E0FCEC33EA6CF0
:1003B20013C0E012072CD0E030E601FAE4CAF423BD
:0403C2005401FB22C5
:0D03C6007A007C0012072CE4FAB333FB220E
:1003D3007A007C0012072C0B6004E4FA33FBEB2257
:0F03E3007A007C0012072C0B6003E4FAFBEB227C
:0F03F2007A007C0012072C6004E4FA04FBEB2273
:100401008EB38FB2E033E06A13C0E01207C5D0F01B
:0F041100600C30F602AAF0EA33B3E4FA33FB22B0
:100420008EB38F82E033E06A13C0E01207C5D0E00C
:0B04300030E601FAE4CA235401FB226D
:10043B008E838F82E033E06A13C0E01207C5D0E0F1
:0C044B0030E601FAE4CAF235401FB225D
:100457000D083D082E493F5F0A3E493A3C082C08352
:100467000BB030AC004C005C00078040800BC002C0F1
:100477003C00078026F00BF6120735D000BB803CB
:0F04870005D005D00422BB058A04D003D00222B1
:100496000D083D082120525800ED083D08212052506
:1004A600C3E499F9E498FBC082C083BA8BBBB2C03A
:1004B60082C083802B78007901800478FF79FFD094
:1004C60083D082E493A3C082C0838A838B82B401E3
```

:1004D60005E029FBF022C082C083B40213E0FAA330
:1004E600E029FBEA38FAD083D082F0A3EBF04A2267
:1004F60075F004C0007802E0F608A3D5F0F929FDEE
:10050600D000EC38FCEB38FBEA38FAD083D08275A1
:10051600F0047802E6F0A308D5F0F94C4B4A22E441
:1005260093F8A3E493F9A322D083D0821205258001
:100536000ED083D082120525C3E439F9E498F8C059
:100546008 2C0838A838BB2C082C083B02A780079A6
:1005560001800478FF79FFD083D082E493A3C08220
:100566000C0838A838BB2B40107E029F0C399FB22FA
:10057600C082C083B40219E0FAA3E029FBEA38FA84
:10058600D083D082F0A3EBF0C399FBEA98FA4B2212
:1005960075F004C0007802E0F608A3D5F0F929FD4D
:1005A600D000EC38FCEB38FBEA38FAD083D0827501
:1005B600F004C0007802E6F0A308D5F0F9D000C335
:0F05C60099FDEC98FCEB98FBEA98FA4B4C4D2210
:1005D500EB601124F05004E4FAFB22ECC313FCEDAC
:0B05E50013FDDBF78C02BD03EA4B22B4
:1005F000EB601124F05004E4FAFB22EDC333FDEC70
:0B06000033FCDBF78C02BD03EA4B2279
:10060B00C003120A6ED082E582601824E05006E423
:10061B00FAFBFCFD2278047902C3E713F709D8FA39
:08062B00D582F2EA4B4C4D228E
:08063300EA5CFAEB5DFB4A22D0
:08063B00EAF4FAEBF4FB4A2299
:100643008A838BB2EDF0FB228A83BBB2ECF0FAA300
:10065300EDF0FB4A22C003C002120A6ED083D0829F
:0E06630078047902E7F009A3D8FA4C4B4A223A
:100671007803790180087902800279047802D083B5
:100681000D082E4932BF5F0A3E4933AB02778037 9A1
:1006910001801478057901800E7902800878047947
:1006A10002B00479047802D083D082E4932FF5F09C
:1006B100A3E4933EA3C082C083F58385F08275F0E5
:0C06C10000E0F642F008A3D9F8E5F022B2
:1006CD0075F00078047902E0F745F0F5F009A3D84C
:1006DD00F62275F00079047802E6F045F0F5F008A1
:0406ED00A3D9F62275
:1006F1007803790180087902800279047902D08335
:10070100D082E4932FF5F0A3E4933EA3C082C0838B
:10071100F58385F08275F000E6F0A30842F0D9F880
:03072100E5F022DE
:08072400EB2DFBEA3CFA4B222D
:09072C00EDC39BFBEC3AFA4B2291
:10073500EBBCF0A4CABDF0A42AFAEBBDF0A4FBE5AE
:05074500F02AFA4B222E
:10074A007900EA30E707790178031207BCEC30E751
:10075A000086301017B051207BCC001120782D001A3
:0F076A00B9010578051207BC8C028D03EA4B22FA
:09077900E4C39BFBE49AFA4B2255
:107 08200BB0004BA000122780079007410C0E0C3F3
:10079200ED33FDEC33FCE933F9E833F8C3E99BF5BB
:1007A200F0E39A400BF8A3F0ED2401FDEC3400FCCE
:0A07B200D0E014C0E070D8D0E022BF
:0307BC00E4C396F618E496F62257
:1007C5008EB3BF827B04E0C0E0A3D8FAC37B0479D9
:0B07D50005D0E097F719D8F9020A9B45
:1007E00012087A12081E8C007905E6F71819B9016B
:0A07F000F9E58124F4F581020A9B6B

:1007FA0012087A12081E8B007905E6F71819B90152
:0A080A00F9E58124F4F581020A9B50
:0A081400780512 0B70EA4B4C4D22E3
:10081E008D0079 04B6000418D9FA227A208C00795A
:10082E0008C3E633F618D9FA8E838F82 8B008D01BA
:10083E008AF07A04C3E697F01819A3DAF8AAF04002
:10084E001E8E838F82BB007904E0F6A318D9FA8C62
:10085E0000E62401F6187903E63400F618D9F9DA21
:020B6E00BC22AA

:0A087000C37904E496F618D9FA22C1
:10087A00D0F0D001E4C0E0C0E0C0E08E838FD9
:10088A00827804E0C0E0A3D8FAC002C003C004C062
:10089A0005ADB1E58124FCFC24FCFBC001C0F022EB
:1008AA00D083D082C3E493A3CD9DFDE493A3CC9CD3
:1008BA00FC93A3CB9B7049E493A3CA9A7043EDFBC4
:1008CA00ECFA8011D083D082C3E493A3CB9BFBE4E0
:1008DA0093A3CA9AFA20E729C3E493A3B9E493A3B8
:1008EA009A20E712A3A3EB2B5002058325B2F582F7
:1008FA00E5833A2AF583740193C0E0E493C0E022C9
:05090A00A3A3A380F18E

:10090F00D083D082E493700974 01937004A3A3B001
:10091F000B7402936B6005A3A3A380E8740193C0CB
:06092F00E0E493C0E022A9

:10093500900132AA83AB8290007120990905082F1
:10094500AA83ABB29050B212099B602CC002C0031F
:10095500C082C08378027904E493F6A308D9F98BA1
:10096500828AB38C02BD03120990D83D082D003B2
:10097500D002A3A3A3A380CF209A45082507B0069
:10098500001209A4513650B201322212099B7001CE
:1009950022E4F0A380F5EB65827003EA65B322D03B
:1009A500B3D08278027906E493F6A308D9F9C08248
:1009B500C0B38D828C8312099B6013E493A3AD825F
:0F09C500AC838F828E 83F0A3AF82AEB380E42257
:1009D4006019C000C001C083C082F854012402F928
:1009E400120A75D082D083D001D000EF25B2FDEEAB
:1009F4003583FCC3EF99F582FFEE98FEF583D002B0
:100A0400D003D0E0F0A3D0E0F0A3ECF0A3EDF0C06D
:100A140003C002228E838F82E0F5F0A3E0C0E0C021
:100A2400F0A3E0FEA3E0FF22D001D000D0E0D0F09C
:090A3400C000C001C0F0C0E022C6
:070A3D0078017903020A753C
:070A440078017905020A7533
:070A4B0078027902020A752E
:070A520078027904020A7525
:070A590078047902020A751E
:070A600078017905020A8804
:070A670078027904020A88FD
:070A6E0078047902020A88F6
:100A7500EFC398FFEE9400FE8F828E83F7F0A30903
:030A8500D8FA227A
:100A8800C0E08F828E83E0F7A309D8FAAE83AF82E5
:030A9800D0E02289
:100A9B0092F0EF2404FFEE3400FEA2F0ED4C4B4A33
:010AAB002228
:1051D800C0E0C0D0C0F0C083C0B2C020C00DC00CE9
:1051E800C00BC00AD2D3C2D49000287401F090003A
:1051F80047E0702B900029E0FAA3E0FBA3E0FCA3B2
:10520800E02401FDEC3400FCEB3400FBEA34009 0B0

:105218000029F0A3EBF0A3ECF0A3EDF00252B59057
:1052280003E6E0F520D57F29857D7FD57E23857C23
:105238007E857B7F857B7D9003EDE06014F5F090A3
:105248000C007E055F0B5F0099003E9E4F0A3F08059
:105258002ED57A5385787AD5794D85777985767A7A
:105268008576789003E8E0F5F09003EAE0B5F0275A
:105278009003E7E0F5F090C005E0B5F01AD202908F
:105288000C007E4F090001FE0547FF090C005F0D212
:1052980004C28CC2AAB0109003EAE09003EBF09060
:1052A800C005E09003E7F09003E6E520F0D00AD0CF
:1052B8000BD00CD00DD020D082D083D0F0D0D0D05D
:0252C800E032D2
:1053B400C0E0C0D0C0F0C0B3C082D2D3C2D49001E8
:105394002FE0F5F0A3E02401C5F0340090012FF0D4
:1053A400A3E5F0F0758D3C758BB0D082D0B3D0F03E
:0553B400D0D0D0E03272
:1051360C0E0C0D0C0F0C0B3C0B2C00FC00EC00D9A
:105146000C00CC00BC00AC009C008C020D2D3C2D44C
:105156009003E6E0F5209003E9E0FEA3E0FF2001DE

:105166000AC39401FFEE94000251772401FFEE3446
:1051760000FE9003E9F0A3EFF020033B9003EBE084
:1051B600B50E2BA3E0B50F2630000DD2039003EF2A
:1051960E090C007F00251B490C007E4F090001F01
:1051A600E0547FF090C005F0D204C28CC2AA9003EE
:1051B500E6E520F0D020D008D009D00AD00BD00CDC
:1051C600D00DD00ED00FD082D083D0F0D0D0D0E08A
:0251D600322283
:1052CA00C0E0C0D0C083C082C00DC00CC00BC00AF1
:1052DA00D2D3C2D490003EE060607400F0900040E7
:1052EA00E004F0B4020B90C00674FDF0C28C0253C5
:1052FA004402532CB4022B90002B7400F090002929
:10530A00E0FAA3E0FBA3E0FCA3E0FD900031EAF0A1
:10531A00A3EBF0A3ECF0A3EDF090002BE070DB0221
:10532A005344900041E060127400F07A049000291E
:10533A00F0A3DAFC90C00674FEF0D00AD00BD00CB1
:0B534A00D00DD082D083D0D0D0E03254
:10535500C0E0C0D0C0B3C0B230980EE5999000B5FA
:10536500F09000B47401F0C29830990AD290900080
:0F537500B67401F0C299D082D083D0D0D0E0328C

We claim:

1. An apparatus for automatically carrying out a melt indexing test relating to a substance, comprising:
   a plurality of cartridges, where each cartridge includes a bore for receiving a quantity of the substance to be tested and further includes a plug disposed at a first end of the bore, with each plug having an orifice;
   a piston adapted for placement within said each said bore of said cartridges, each said piston for resting adjacent said quantity of the substance;
   a heater having a receptacle for receiving a cartridge and for heating the cartridge and the substance within the cartridge, for melting the substance, thus forming a resin;
   means for holding said plurality of cartridges;
   means for grasping each cartridge and transferring the cartridge to the receptacle;
   means for applying a force to said piston for tamping the substance when the substance is in a solid state and for driving said resin through said orifice as an extrudate; and
   processor means having a memory for storing a predetermined sequence of commands relating to the melt index test, for automatically controlling said holding means, said grasping and transferring means, and said force applying means.

2. An apparatus for automatically carrying out a melt indexing test relating to at least one substance, comprising:
   a plurality of cartridges, where each cartridge includes a bore for receiving a quantity of the substance to be tested and further includes a plug disposed at a lower end, with each plug having an orifice;
   a piston adapted for placement within said each said bore of said cartridges, each said piston for resting adjacent said quantity of the substance;
   a heater having a receptacle for receiving a cartridge and for heating the cartridge and the substance within the cartridge, for melting the substance, thus forming a resin;
   means for holding said plurality of cartridges;
   means for grasping each cartridge and transferring the cartridge to the receptacle;
   a lift mechanism with a variable height positioned above said receptacle and having a first platform having a first bore therethrough;
   first means for raising and lowering said lift mechanism;
   a weight carried on said first platform;
   a tamping rod carried beneath said weight and slidiably extending through said first bore, said tamping rod and said receptacle being positioned such that, upon lowering of said lift mechanism, said tamping rod contacts said piston for applying force due to said weight upon said substance, for tamping the substance when the substance is in a solid state and for driving said resin through said orifice as an extrudate;
   means for cutting off said extrudate passing through said orifice; and
   processor means having a memory for storing a predetermined sequence of commands relating to the melt index test, for automatically controlling said holding means, said grasping and transferring means, said first raising and lowering means and said cutting means.

3. The apparatus of claim 2, further including means, coupled to said processor, for carrying out said predetermined sequence of commands once for each of said plurality of cartridges.

4. The apparatus of claim 2, further including means, coupled to said processor, for detecting positions of said holding means for said plurality of cartridges.

5. The apparatus of claim 2, further comprising:
   a threaded rod positioned adjacent said lift mechanism;
   first means for rotating said threaded rod;
   means attached to said lift mechanism threadedly engaging said threaded rod, such that rotation of said threaded rod in a first direction raises said lift mechanism and rotation of said threaded rod in a second direction lowers said lift mechanism; and a weight tray attached to said tamping rod and supporting said weight;

wherein said lift mechanism includes a second platform mounted above said first platform, such that when said lift mechanism is lowered for driving said resin through said orifice, said second platform may contact said weight such that a driving force from said first raising and lowering means is transmitted through said weight, said tamping rod and the piston to said resin.

6. The apparatus of claim 5, further comprising:

a flag having a plurality of windows and carried by said weight tray, said windows being aligned with one another in a direction substantially parallel to a length of each said cartridge when said cartridge is positioned within said receptacle;

a first sensor coupled to said processor means and carried by said lift mechanism for detecting when one of said windows is adjacent said first sensor, said windows being positioned such that different positions of said weight tray correspond to different ones of said windows being adjacent said first sensor, for determining an amount of time taken for a force due to said weight to move a predetermined distance in driving said resin through said orifice.

7. A method for automatically carrying out a melt indexing test relating to a substance, including the steps of:

(1) positioning each of a plurality of cartridges in a carousel, each said cartridge including a bore for receiving a quantity of the substance to be tested and further including a plug having an orifice disposed at a first end of the cartridge and a piston disposed at a second end of the cartridge;

(2) loading a first said cartridge with a quantity of the substance;

(3) positioning the piston on he substance carried within the bore of the first cartridge;

(4) repeating steps 2 and 3 for each of the plurality of cartridges in addition to the first cartridge;

(5) positioning the first cartridge at a heater with an automatically controlled grasping and transferring means;

(6) compressing the substance by applying a first force to the piston;

(7) leaving the fist cartridge at the heater for a length of time to allow the substance to melt;

(8) applying a second force to the piston to extrude a portion of the substance through the orifice;

(9) determining a melt index of the substance based upon the extrusion through the orifice;

(10) removing the first cartridge from the heater with said grasping and transferring means;

(11) replacing the first cartridge in the carousel; and

(12) repeating each of steps 5 through 11 for each cartridge in addition to the first cartridge, wherein steps 5 through 12 are automatically controlled by a processor storing a predetermined sequence of commands for carrying out the individual steps.

8. The method of claim 7, wherein the stecond force is applied in step 8 by a force applying means coupled to a position detector, where the force applying means changes position relative to the position detector as the substance is extruded through the orifice, and wherein step 9 includes the step of determining an amount of time taken for the force applying means to travel a predetermined distance relative to the position detector.

9. The method of claim 7, wherein step 9 includes the step of determining an amount of time taken for a predetermined amount of the substance to be extruded through the orifice.

10. The method of claim 7, wherein step 8 includes the step of continuing to apply the second force until substantially all of the substance has been extruded through the orifice.

11. The method of claim 7, wherein the cartridge is substantially vertical when positioned at the heater, and wherein the second force is applied by placing a predetermined weight atop the piston.

* * * * *